US008758767B2

(12) United States Patent
DiLorenzo et al.

(10) Patent No.: US 8,758,767 B2
(45) Date of Patent: Jun. 24, 2014

(54) ANTIGENS TARGETED BY PREVALENT PATHOGENNIC T CELLS IN TYPE 1 DIABETES AND USES THEREOF

(75) Inventors: Teresa P. DiLorenzo, Bayside, NY (US); Anne M. Evans, Chapel Hill, NC (US); Donald F. Hunt, Charlottesville, VA (US); Scott M. Lieberman, Philadelphia, PA (US); Stanley G. Nathenson, Pelham Manor, NY (US); Pere Santamaria, Calgary (CA); Jeffrey Shabanowitz, Charlottesville, VA (US)

(73) Assignees: Albert Einstein College of Medicine of Yeshiva University, Bronx, NY (US); University of Virginia Patent Foundation, Charlottesville, VA (US); University Technologies International Inc., Alberta (CA)

( * ) Notice: Subject to any disclaimer, the term of this patent is extended or adjusted under 35 U.S.C. 154(b) by 1927 days.

(21) Appl. No.: 10/557,273

(22) PCT Filed: May 20, 2004

(86) PCT No.: PCT/US2004/015752
§ 371 (c)(1),
(2), (4) Date: Jan. 16, 2007

(87) PCT Pub. No.: WO2005/033267
PCT Pub. Date: Apr. 14, 2005

(65) Prior Publication Data
US 2008/0153112 A1 Jun. 26, 2008

Related U.S. Application Data

(60) Provisional application No. 60/471,868, filed on May 20, 2003.

(51) Int. Cl.
*A61K 39/00* (2006.01)
*A61K 39/385* (2006.01)
(52) U.S. Cl.
USPC .................................. 424/192.1; 424/193.1
(58) Field of Classification Search
None
See application file for complete search history.

(56) References Cited

U.S. PATENT DOCUMENTS

| 6,623,947 | B2 | 9/2003 | Chen |
| 6,627,425 | B1 | 9/2003 | Chen |
| 2005/0014241 | A1 | 1/2005 | Chen |
| 2007/0203059 | A1 | 8/2007 | Hutton et al. |
| 2009/0137485 | A1 | 5/2009 | DiLorenzo et al. |
| 2010/0009923 | A1 | 1/2010 | DiLorenzo et al. |

FOREIGN PATENT DOCUMENTS

WO    WO 01/92497    * 11/2001

OTHER PUBLICATIONS

HLA Nomenclature@hla.alleles.org (2010).*
Tsurui and Takahashi. J. Pharmacol. Sci. 2007;105:299-316.*
Amrani A. et al., "Progression of autoimmune diabetes driven by avidity maturation of a T-cell population"; Nature, 2000, vol. 406, pp. 739-742.
Anderson B. et al., "Prevalent CD8+ T cell response against one peptide/MHC complex in autoimmune diabetes"; PNAS, 1999, vol. 96, pp. 9311-9316.
Arden S.D. et al., "Molecular Cloning of a Pancreatic Islet-Specific Glucose-6-Phosphatase Catalytic Subunit-Related Protein"; Diabetes, 1999, vol. 48, pp. 531-542.
Baekkeskov S. et al., "Identification of the 64K autoantigen in insulin-dependent diabetes as the GABA-synthesizing enzyme glutamic acid decarboxylase"; Nature, 1990, vol. 347, No. 6289, pp. 151-156.
DiLorenzo T.P. et al., "Major histocompatibility complex class I-restricted T cells are required for all but the end stages of diabetes development in nonobese diabetic mice and use a prevalent T cell receptor α chain gene rearrangement"; PNAS, 1998, vol. 95, pp. 12538-12543.
DiLorenzo T.P. et al., "During the Early Prediabetic Period in NOD Mice, the Pathogenic CD8+ T-Cell Population Comprises Multiple Antigenic Specificities"; Clinical Immunology, 2002, vol. 105, No. 3, pp. 332-341.
Liblau R.S. et al., "Autoreactive CD8 T Cells in Organ-Specific Autoimmunity: Emerging Targets for Therapeutic Intervention"; Immunity, 2002, vol. 17, pp. 1-6.

(Continued)

*Primary Examiner* — Gerald R Ewoldt
(74) *Attorney, Agent, or Firm* — Amster, Rothstein & Ebenstein LLP

(57) ABSTRACT

The present invention is based on the identification of a predominant ligand of CD8+ T cells that are responsible for type 1 diabetes. That ligand is islet-specific glucose-6-phosphatase catalytic subunit-related protein (IGRP). Several CD8+ T cell-binding peptides from IGRP are identified, including the peptide comprising amino acids 206-214 of the IGRP sequence, which has high avidity to the most prevalent T cell receptor of pathogenic CD8+ T cells in autoimmune diabetes. The invention thus provides oligopeptide and polypeptide compositions comprising YLKTN(A/I/L/V)FL (SEQ ID NO:3), FLWSVFWLI (SEQ ID NO:4), (T/A)YY (G/T)FLNFM (SEQ ID NO:5), LR(L/V)(F/L)(G/N)IDLL (SEQ ID NO:6), KWCANPDWI (SEQ ID NO:7), and SFCK-SASIP (SEQ ID NO:8). Also provided are oligopeptide compositions 8-10 amino acids in length and completely homologous with a mammalian IGRP, where the oligopeptide is capable of binding a human MHC class I molecule. Additionally, various methods of treating a mammal using the above compositions are provided, where the mammal is at risk for or has type 1 diabetes. Also provided are methods of preventing a CD8+ T cell that is cytotoxic to pancreatic islet β-cells from destroying a mammalian β-cell, where the methods also use the above compositions. Further provided are methods for determining whether a mammal is at risk for or has type 1 diabetes, where the methods use the above compositions.

3 Claims, 10 Drawing Sheets

(56) References Cited

OTHER PUBLICATIONS

Lieberman S.M. and DiLorenzo T.P., "A comprehensive guide to antibody and T-cell response in type 1 diabetes"; Tissue Antigens, 2003, vol. 62, No. 5, pp. 359-377.

Lieberman S.M. et al., "Identification of the β cell antigen targeted by a prevalent population of pathogenic CD8+ T cells in autoimmune diabetes"; PNAS, 2003, vol. 100, No. 14, pp. 8384-8388.

Martin S.E. et al., "Subfemtomole MS and MS/MS Peptide Sequence Analysis Using Nano-HPLC Micro-ESI Fourier Transform Ion Cyclotron Resonance Mass Spectrometry"; Analytical Chemistry, 2000, vol. 72, No. 18, pp. 4266-4274.

Nagata M. et al., "Evidence for the Role of CD8+ Cytotoxic T Cells in the Destruction of Pancreatic β-cells in Nonobese Diabetic Mice"; The Journal of Immunology, 1994, vol. 152, No. 4, pp. 1952-2073.

Palmer J.P. et al., "Insulin antibodies in insulin-dependent diabetics before insulin treatment"; Science, 1983, vol. 222, pp. 1337-1339.

Pociot F. and McDermott M.F., "Genetics of type 1 diabetes mellitus"; Genes and Immunology, 2002, vol. 3, pp. 235-249.

Rabin D.U. et al., "Cloning and Expression of IDDM-Specific Human Autoantigens"; Diabetes, 1992, vol. 41, No. 2, pp. 183-186.

Santamaria P. et al., "Beta-Cell-Cytotoxic CD8+ T Cells from Nonobese Diabetic Mice Use Highly Homologous T Cell Receptor α-Chain CDR3 Sequences"; The Journal of Immunology, 1995, vol. 154, No. 5, pp. 2494-2503.

Serreze D.V. et al., "Autoreactive Diabetic T-Cells in NOD Mice Can Efficiently Expand From a Greatly Reduced Precursor Pool"; Diabetes, 2001, vol. 50, pp. 1992-2000.

Trudeau J.D. et al., "Prediction of spontaneous autoimmune diabetes in NOD mice by quantification of autoreactive T cells in peripheral blood"; The Journal of Clinical Investigation, 2003, vol. 111, No. 2, pp. 217-223.

Wong S.F. et al., "Analysis of structure and function relationships of an autoantigenic peptide of insulin bound to H-2Kd that stimulates CD8 T cells in insulin-dependent diabetes mellitus"; PNAS, 2002, vol. 99, No. 8, pp. 5551-5556.

Wong S.F. et al., "Identification of an MHC class I-restricted autoantigen in type 1 diabetes by screening an organ-specific cDNA library"; Nature Medicine, 1999, vol. 5, No. 9, pp. 1026-1031.

Verdaguer J. et al., "Acceleration of Spontaneous Diabetes in TCR-β-Transgenic Nonobese Diabetic Mice by β-Cell Cytotoxic CD8+ T Cells Expressing Identical Endogenous TCR-α Chains"; The Journal of Immunology, 1996, vol. 157, No. 10, pp. 4726-4735.

Verdaguer J. et al., "Spontaneous Autoimmune Diabetes in Monoclonal T Cell Nonobese Diabetic Mice"; The Journal of Experimental Medicine, 1997, vol. 186, No. 10, pp. 1663-1676.

Martin C.C. et al., entitled "Cloning and Characterization of the Human and Rat Islet-specific Glucose-6-phosphatase Catalytic Subunit-related Protein (IGRP) Genes," The Journal of Biological Chemistry, 2001, vol. 276, No. 27, pp. 25197-25207.

\* cited by examiner

SEQUENCE LISTING

<160> NUMBER OF SEQ ID NOS: 99

<210> SEQ ID NO 1
<211> LENGTH: 355
<212> TYPE: PRT
<213> ORGANISM: Mus musculus

<400> SEQUENCE: 1

| | | | | | | | | | | | | | | |
|---|---|---|---|---|---|---|---|---|---|---|---|---|---|---|
| Met | Asp | Phe | Leu | His | Arg | Ser | Gly | Val | Leu | Ile | Ile | His | His | Leu | Gln |
| 1 | | | | 5 | | | | | 10 | | | | | 15 | |
| Glu | Asp | Tyr | Arg | Thr | Tyr | Tyr | Gly | Phe | Leu | Asn | Phe | Met | Ser | Asn | Val |
| | | | 20 | | | | | 25 | | | | | 30 | | |
| Gly | Asp | Pro | Arg | Asn | Ile | Phe | Ser | Ile | Tyr | Phe | Pro | Leu | Trp | Phe | Gln |
| | | 35 | | | | | 40 | | | | | 45 | | | |
| Leu | Asn | Gln | Asn | Val | Gly | Thr | Lys | Met | Ile | Trp | Val | Ala | Val | Ile | Gly |
| | 50 | | | | | 55 | | | | | 60 | | | | |
| Asp | Trp | Phe | Asn | Leu | Ile | Phe | Lys | Trp | Ile | Leu | Phe | Gly | His | Arg | Pro |
| 65 | | | | | 70 | | | | | 75 | | | | | 80 |
| Tyr | Trp | Trp | Ile | Gln | Glu | Thr | Glu | Ile | Tyr | Pro | Asn | His | Ser | Ser | Pro |
| | | | | 85 | | | | | 90 | | | | | 95 | |
| Cys | Leu | Glu | Gln | Phe | Pro | Thr | Thr | Cys | Glu | Thr | Gly | Pro | Gly | Ser | Pro |
| | | | | 100 | | | | | 105 | | | | | 110 | |
| Ser | Gly | His | Ala | Met | Gly | Ser | Ser | Cys | Val | Trp | Tyr | Val | Met | Val | Thr |
| | | | 115 | | | | | 120 | | | | | 125 | | |
| Ala | Ala | Leu | Ser | Tyr | Thr | Ile | Ser | Arg | Met | Glu | Glu | Ser | Ser | Val | Thr |
| | | 130 | | | | | 135 | | | | | 140 | | | |
| Leu | His | Arg | Leu | Thr | Trp | Ser | Phe | Leu | Trp | Ser | Val | Phe | Trp | Leu | Ile |
| 145 | | | | | 150 | | | | | 155 | | | | | 160 |
| Gln | Ile | Ser | Val | Cys | Ile | Ser | Arg | Val | Phe | Ile | Ala | Thr | His | Phe | Pro |
| | | | | 165 | | | | | 170 | | | | | 175 | |
| His | Gln | Val | Ile | Leu | Gly | Val | Ile | Gly | Gly | Met | Leu | Val | Ala | Glu | Ala |
| | | | 180 | | | | | 185 | | | | | 190 | | |
| Phe | Glu | His | Thr | Pro | Gly | Val | His | Met | Ala | Ser | Leu | Ser | Val | Tyr | Leu |
| | | | 195 | | | | | 200 | | | | | 205 | | |
| Lys | Thr | Asn | Val | Phe | Leu | Phe | Leu | Phe | Ala | Leu | Gly | Phe | Tyr | Leu | Leu |
| | | | 210 | | | | | 215 | | | | | 220 | | |
| Leu | Arg | Leu | Phe | Gly | Ile | Asp | Leu | Leu | Trp | Ser | Val | Pro | Ile | Ala | Lys |
| 225 | | | | | 230 | | | | | 235 | | | | | 240 |
| Lys | Trp | Cys | Ala | Asn | Pro | Asp | Trp | Ile | His | Ile | Asp | Ser | Thr | Pro | Phe |
| | | | | 245 | | | | | 250 | | | | | 255 | |
| Ala | Gly | Leu | Val | Arg | Asn | Leu | Gly | Val | Leu | Phe | Gly | Leu | Gly | Phe | Ala |
| | | | 260 | | | | | 265 | | | | | 270 | | |
| Ile | Asn | Ser | Glu | Met | Phe | Leu | Arg | Ser | Cys | Gln | Gly | Glu | Asn | Gly | Thr |
| | | 275 | | | | | 280 | | | | | 285 | | | |
| Lys | Pro | Ser | Phe | Arg | Leu | Leu | Cys | Ala | Leu | Thr | Ser | Leu | Thr | Thr | Met |
| | 290 | | | | | 295 | | | | | 300 | | | | |
| Gln | Leu | Tyr | Arg | Phe | Ile | Lys | Ile | Pro | Thr | His | Ala | Glu | Pro | Leu | Phe |
| 305 | | | | | 310 | | | | | 315 | | | | | 320 |
| Tyr | Leu | Leu | Ser | Phe | Cys | Lys | Ser | Ala | Ser | Ile | Pro | Leu | Met | Val | Val |
| | | | | 325 | | | | | 330 | | | | | 335 | |
| Ala | Leu | Ile | Pro | Tyr | Cys | Val | His | Met | Leu | Met | Arg | Pro | Gly | Asp | Lys |
| | | | 340 | | | | | 345 | | | | | 350 | | |
| Lys | Thr | Lys | | | | | | | | | | | | | |
| | | 355 | | | | | | | | | | | | | |

<210> SEQ ID NO 2
<211> LENGTH: 355
<212> TYPE: PRT
<213> ORGANISM: Homo sapiens

<400> SEQUENCE: 2

```
Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
            20                  25                  30

Gly Asp Pro Arg Asn Ile Phe Phe Ile Tyr Phe Pro Leu Cys Phe Gln
        35                  40                  45

Phe Asn Gln Thr Val Gly Thr Lys Met Ile Trp Val Ala Val Ile Gly
    50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125

Ala Ala Leu Ser His Thr Val Cys Gly Met Asp Lys Phe Ser Ile Thr
130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Ile Gln Thr Ala Ser Leu Gly Thr Tyr Leu
        195                 200                 205

Lys Thr Asn Leu Phe Leu Phe Leu Phe Ala Val Gly Phe Tyr Leu Leu
210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Leu Ser Cys Arg Gly Gly Asn Asn Tyr
        275                 280                 285

Thr Leu Ser Phe Arg Leu Leu Cys Ala Leu Thr Ser Leu Thr Ile Leu
290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gln Ser Gly Lys
            340                 345                 350

Lys Ser Gln
        355
```

<210> SEQ ID NO 3
<211> LENGTH: 8
<212> TYPE: PRT
<213> ORGANISM: Artificial
<220> FEATURE:
<223> OTHER INFORMATION: peptide
<220> FEATURE:
<221> NAME/KEY: PEPTIDE
<222> LOCATION: (6)..(6)
<223> OTHER INFORMATION: where Xaa is A, I, L or V

```
<400> SEQUENCE: 3

Tyr Leu Lys Thr Asn Xaa Phe Leu
1               5

<210> SEQ ID NO 4
<211> LENGTH: 9
<212> TYPE: PRT
<213> ORGANISM: Artificial
<220> FEATURE:
<223> OTHER INFORMATION: peptide

<400> SEQUENCE: 4

Phe Leu Trp Ser Val Phe Trp Leu Ile
1               5

<210> SEQ ID NO 5
<211> LENGTH: 9
<212> TYPE: PRT
<213> ORGANISM: Artificial
<220> FEATURE:
<223> OTHER INFORMATION: peptide
<220> FEATURE:
<221> NAME/KEY: PEPTIDE
<222> LOCATION: (1)..(1)
<223> OTHER INFORMATION: where Xaa is T or A
<220> FEATURE:
<221> NAME/KEY: PEPTIDE
<222> LOCATION: (4)..(4)
<223> OTHER INFORMATION: where Xaa is G or T

<400> SEQUENCE: 5

Xaa Tyr Tyr Xaa Phe Leu Asn Phe Met
1               5

<210> SEQ ID NO 6
<211> LENGTH: 9
<212> TYPE: PRT
<213> ORGANISM: Artificial
<220> FEATURE:
<223> OTHER INFORMATION: peptide
<220> FEATURE:
<221> NAME/KEY: PEPTIDE
<222> LOCATION: (3)..(3)
<223> OTHER INFORMATION: where Xaa at 3 is L or V
<220> FEATURE:
<221> NAME/KEY: PEPTIDE
<222> LOCATION: (4)..(4)
<223> OTHER INFORMATION: where Xaa at 4 is F or L
<220> FEATURE:
<221> NAME/KEY: PEPTIDE
<222> LOCATION: (5)..(5)
<223> OTHER INFORMATION: where Xaa at 5 is G or N

<400> SEQUENCE: 6

Leu Arg Xaa Xaa Xaa Ile Asp Leu Leu
1               5

<210> SEQ ID NO 7
<211> LENGTH: 9
<212> TYPE: PRT
<213> ORGANISM: Artificial
<220> FEATURE:
<223> OTHER INFORMATION: peptide

<400> SEQUENCE: 7

Lys Trp Cys Ala Asn Pro Asp Trp Ile
1               5

<210> SEQ ID NO 8
```

```
<211> LENGTH: 9
<212> TYPE: PRT
<213> ORGANISM: Artificial
<220> FEATURE:
<223> OTHER INFORMATION: peptide

<400> SEQUENCE: 8

Ser Phe Cys Lys Ser Ala Ser Ile Pro
1               5

<210> SEQ ID NO 9
<211> LENGTH: 9
<212> TYPE: PRT
<213> ORGANISM: Artificial
<220> FEATURE:
<223> OTHER INFORMATION: peptide

<400> SEQUENCE: 9

Thr Tyr Tyr Gly Phe Leu Asn Phe Met
1               5

<210> SEQ ID NO 10
<211> LENGTH: 9
<212> TYPE: PRT
<213> ORGANISM: Artificial
<220> FEATURE:
<223> OTHER INFORMATION: peptide

<400> SEQUENCE: 10

Leu Arg Leu Phe Gly Ile Asp Leu Leu
1               5

<210> SEQ ID NO 11
<211> LENGTH: 9
<212> TYPE: PRT
<213> ORGANISM: Artificial
<220> FEATURE:
<223> OTHER INFORMATION: peptide

<400> SEQUENCE: 11

Lys Tyr Asn Lys Ala Asn Val Phe Leu
1               5

<210> SEQ ID NO 12
<211> LENGTH: 9
<212> TYPE: PRT
<213> ORGANISM: Artificial
<220> FEATURE:
<223> OTHER INFORMATION: peptide

<400> SEQUENCE: 12

Lys Tyr Asn Lys Ala Asn Ala Phe Leu
1               5

<210> SEQ ID NO 13
<211> LENGTH: 9
<212> TYPE: PRT
<213> ORGANISM: Artificial
<220> FEATURE:
<223> OTHER INFORMATION: peptide

<400> SEQUENCE: 13

Leu Tyr Leu Val Cys Gly Glu Arg Gly
1               5

<210> SEQ ID NO 14
<211> LENGTH: 9
<212> TYPE: PRT
```

```
<213> ORGANISM: Artificial
<220> FEATURE:
<223> OTHER INFORMATION: peptide

<400> SEQUENCE: 14

Leu Tyr Leu Val Cys Gly Glu Arg Ile
1               5

<210> SEQ ID NO 15
<211> LENGTH: 9
<212> TYPE: PRT
<213> ORGANISM: Artificial
<220> FEATURE:
<223> OTHER INFORMATION: peptide

<400> SEQUENCE: 15

Lys Tyr Gln Ala Val Thr Thr Thr Leu
1               5

<210> SEQ ID NO 16
<211> LENGTH: 9
<212> TYPE: PRT
<213> ORGANISM: Artificial
<220> FEATURE:
<223> OTHER INFORMATION: peptide

<400> SEQUENCE: 16

Lys Tyr Cys Leu Ile Thr Ile Phe Leu
1               5

<210> SEQ ID NO 17
<211> LENGTH: 9
<212> TYPE: PRT
<213> ORGANISM: Artificial
<220> FEATURE:
<223> OTHER INFORMATION: peptide
<220> FEATURE:
<221> NAME/KEY: PEPTIDE
<222> LOCATION: (3)..(3)
<223> OTHER INFORMATION: X is I or L
<220> FEATURE:
<221> NAME/KEY: PEPTIDE
<222> LOCATION: (9)..(9)
<223> OTHER INFORMATION: X is I or L

<400> SEQUENCE: 17

Val Tyr Xaa Lys Thr Asn Val Phe Xaa
1               5

<210> SEQ ID NO 18
<211> LENGTH: 9
<212> TYPE: PRT
<213> ORGANISM: Artificial
<220> FEATURE:
<223> OTHER INFORMATION: peptide
<220> FEATURE:
<221> NAME/KEY: PEPTIDE
<222> LOCATION: (1)..(1)
<223> OTHER INFORMATION: X is I or L
<220> FEATURE:
<221> NAME/KEY: PEPTIDE
<222> LOCATION: (8)..(9)
<223> OTHER INFORMATION: X is I or L

<400> SEQUENCE: 18

Xaa Tyr Gln Lys Ala Phe Asp Xaa Xaa
1               5

<210> SEQ ID NO 19
<211> LENGTH: 9
```

```
<212> TYPE: PRT
<213> ORGANISM: Artificial
<220> FEATURE:
<223> OTHER INFORMATION: peptide

<400> SEQUENCE: 19

Val Tyr Leu Lys Thr Asn Val Phe Leu
1               5

<210> SEQ ID NO 20
<211> LENGTH: 9
<212> TYPE: PRT
<213> ORGANISM: Artificial
<220> FEATURE:
<223> OTHER INFORMATION: peptide

<400> SEQUENCE: 20

Ile Tyr Gln Lys Ala Phe Asp Leu Ile
1               5

<210> SEQ ID NO 21
<211> LENGTH: 8
<212> TYPE: PRT
<213> ORGANISM: Artificial
<220> FEATURE:
<223> OTHER INFORMATION: peptide

<400> SEQUENCE: 21

Tyr Asn Ile Ala Asn Trp Phe Leu
1               5

<210> SEQ ID NO 22
<211> LENGTH: 9
<212> TYPE: PRT
<213> ORGANISM: Artificial
<220> FEATURE:
<223> OTHER INFORMATION: peptide

<400> SEQUENCE: 22

Thr Tyr Leu Lys Thr Asn Leu Phe Leu
1               5

<210> SEQ ID NO 23
<211> LENGTH: 9
<212> TYPE: PRT
<213> ORGANISM: Artificial
<220> FEATURE:
<223> OTHER INFORMATION: peptide

<400> SEQUENCE: 23

Ala Tyr Tyr Thr Phe Leu Asn Phe Met
1               5

<210> SEQ ID NO 24
<211> LENGTH: 9
<212> TYPE: PRT
<213> ORGANISM: Artificial
<220> FEATURE:
<223> OTHER INFORMATION: peptide

<400> SEQUENCE: 24

Leu Arg Val Leu Asn Ile Asp Leu Leu
1               5

<210> SEQ ID NO 25
<211> LENGTH: 9
<212> TYPE: PRT
<213> ORGANISM: Artificial
```

```
<220> FEATURE:
<223> OTHER INFORMATION: peptide

<400> SEQUENCE: 25

Asp Phe Leu His Arg Ser Gly Val Leu
1               5

<210> SEQ ID NO 26
<211> LENGTH: 9
<212> TYPE: PRT
<213> ORGANISM: Artificial
<220> FEATURE:
<223> OTHER INFORMATION: peptide

<400> SEQUENCE: 26

Phe Leu His Arg Ser Gly Val Leu Ile
1               5

<210> SEQ ID NO 27
<211> LENGTH: 9
<212> TYPE: PRT
<213> ORGANISM: Artificial
<220> FEATURE:
<223> OTHER INFORMATION: peptide

<400> SEQUENCE: 27

Ser Gly Val Leu Ile Ile His His Leu
1               5

<210> SEQ ID NO 28
<211> LENGTH: 9
<212> TYPE: PRT
<213> ORGANISM: Artificial
<220> FEATURE:
<223> OTHER INFORMATION: peptide

<400> SEQUENCE: 28

Asp Tyr Arg Thr Tyr Tyr Gly Phe Leu
1               5

<210> SEQ ID NO 29
<211> LENGTH: 9
<212> TYPE: PRT
<213> ORGANISM: Artificial
<220> FEATURE:
<223> OTHER INFORMATION: peptide

<400> SEQUENCE: 29

Thr Tyr Tyr Gly Phe Leu Asn Phe Met
1               5

<210> SEQ ID NO 30
<211> LENGTH: 9
<212> TYPE: PRT
<213> ORGANISM: Artificial
<220> FEATURE:
<223> OTHER INFORMATION: peptide

<400> SEQUENCE: 30

Gly Phe Leu Asn Phe Met Ser Asn Val
1               5

<210> SEQ ID NO 31
<211> LENGTH: 9
<212> TYPE: PRT
<213> ORGANISM: Artificial
<220> FEATURE:
<223> OTHER INFORMATION: peptide
```

```
<400> SEQUENCE: 31

Ser Asn Val Gly Asp Pro Arg Asn Ile
1               5

<210> SEQ ID NO 32
<211> LENGTH: 9
<212> TYPE: PRT
<213> ORGANISM: Artificial
<220> FEATURE:
<223> OTHER INFORMATION: peptide

<400> SEQUENCE: 32

Gly Asp Pro Arg Asn Ile Phe Ser Ile
1               5

<210> SEQ ID NO 33
<211> LENGTH: 9
<212> TYPE: PRT
<213> ORGANISM: Artificial
<220> FEATURE:
<223> OTHER INFORMATION: peptide

<400> SEQUENCE: 33

Ile Tyr Phe Pro Leu Trp Phe Gln Leu
1               5

<210> SEQ ID NO 34
<211> LENGTH: 9
<212> TYPE: PRT
<213> ORGANISM: Artificial
<220> FEATURE:
<223> OTHER INFORMATION: peptide

<400> SEQUENCE: 34

Leu Trp Phe Gln Leu Asn Gln Asn Val
1               5

<210> SEQ ID NO 35
<211> LENGTH: 9
<212> TYPE: PRT
<213> ORGANISM: Artificial
<220> FEATURE:
<223> OTHER INFORMATION: peptide

<400> SEQUENCE: 35

Gln Leu Asn Gln Asn Val Gly Thr Lys
1               5

<210> SEQ ID NO 36
<211> LENGTH: 9
<212> TYPE: PRT
<213> ORGANISM: Artificial
<220> FEATURE:
<223> OTHER INFORMATION: peptide

<400> SEQUENCE: 36

Leu Asn Gln Asn Val Gly Thr Lys Met
1               5

<210> SEQ ID NO 37
<211> LENGTH: 9
<212> TYPE: PRT
<213> ORGANISM: Artificial
<220> FEATURE:
<223> OTHER INFORMATION: peptide

<400> SEQUENCE: 37
```

Asn Gln Asn Val Gly Thr Lys Met Ile
1               5

<210> SEQ ID NO 38
<211> LENGTH: 9
<212> TYPE: PRT
<213> ORGANISM: Artificial
<220> FEATURE:
<223> OTHER INFORMATION: peptide

<400> SEQUENCE: 38

Trp Phe Asn Leu Ile Phe Lys Trp Ile
1               5

<210> SEQ ID NO 39
<211> LENGTH: 9
<212> TYPE: PRT
<213> ORGANISM: Artificial
<220> FEATURE:
<223> OTHER INFORMATION: peptide

<400> SEQUENCE: 39

Phe Gly His Arg Pro Tyr Trp Trp Ile
1               5

<210> SEQ ID NO 40
<211> LENGTH: 9
<212> TYPE: PRT
<213> ORGANISM: Artificial
<220> FEATURE:
<223> OTHER INFORMATION: peptide

<400> SEQUENCE: 40

Ile Tyr Pro Asn His Ser Ser Pro Cys
1               5

<210> SEQ ID NO 41
<211> LENGTH: 9
<212> TYPE: PRT
<213> ORGANISM: Artificial
<220> FEATURE:
<223> OTHER INFORMATION: peptide

<400> SEQUENCE: 41

Tyr Pro Asn His Ser Ser Pro Cys Leu
1               5

<210> SEQ ID NO 42
<211> LENGTH: 9
<212> TYPE: PRT
<213> ORGANISM: Artificial
<220> FEATURE:
<223> OTHER INFORMATION: peptide

<400> SEQUENCE: 42

Gly His Ala Met Gly Ser Ser Cys Val
1               5

<210> SEQ ID NO 43
<211> LENGTH: 9
<212> TYPE: PRT
<213> ORGANISM: Artificial
<220> FEATURE:
<223> OTHER INFORMATION: peptide

<400> SEQUENCE: 43

Val Trp Tyr Val Met Val Thr Ala Ala

```
1               5

<210> SEQ ID NO 44
<211> LENGTH: 9
<212> TYPE: PRT
<213> ORGANISM: Artificial
<220> FEATURE:
<223> OTHER INFORMATION: peptide

<400> SEQUENCE: 44

Trp Tyr Val Met Val Thr Ala Ala Leu
1               5

<210> SEQ ID NO 45
<211> LENGTH: 9
<212> TYPE: PRT
<213> ORGANISM: Artificial
<220> FEATURE:
<223> OTHER INFORMATION: peptide

<400> SEQUENCE: 45

Ala Leu Ser Tyr Thr Ile Ser Arg Met
1               5

<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Tyr Thr Ile Ser Arg Met Glu Glu Ser
1               5

<210> SEQ ID NO 47
<211> LENGTH: 9
<212> TYPE: PRT
<213> ORGANISM: Artificial
<220> FEATURE:
<223> OTHER INFORMATION: peptide

<400> SEQUENCE: 47

Ile Ser Arg Met Glu Glu Ser Ser Val
1               5

<210> SEQ ID NO 48
<211> LENGTH: 9
<212> TYPE: PRT
<213> ORGANISM: Artificial
<220> FEATURE:
<223> OTHER INFORMATION: peptide

<400> SEQUENCE: 48

Ser Arg Met Glu Glu Ser Ser Val Thr
1               5

<210> SEQ ID NO 49
<211> LENGTH: 9
<212> TYPE: PRT
<213> ORGANISM: Artificial
<220> FEATURE:
<223> OTHER INFORMATION: peptide

<400> SEQUENCE: 49

Arg Met Glu Glu Ser Ser Val Thr Leu
1               5
```

```
<210> SEQ ID NO 50
<211> LENGTH: 9
<212> TYPE: PRT
<213> ORGANISM: Artificial
<220> FEATURE:
<223> OTHER INFORMATION: peptide

<400> SEQUENCE: 50

Glu Ser Ser Val Thr Leu His Arg Leu
1               5

<210> SEQ ID NO 51
<211> LENGTH: 9
<212> TYPE: PRT
<213> ORGANISM: Artificial
<220> FEATURE:
<223> OTHER INFORMATION: peptide

<400> SEQUENCE: 51

Ser Phe Leu Trp Ser Val Phe Trp Leu
1               5

<210> SEQ ID NO 52
<211> LENGTH: 9
<212> TYPE: PRT
<213> ORGANISM: Artificial
<220> FEATURE:
<223> OTHER INFORMATION: peptide

<400> SEQUENCE: 52

Thr Tyr Tyr Gly Phe Lys Asn Phe Met
1               5

<210> SEQ ID NO 53
<211> LENGTH: 9
<212> TYPE: PRT
<213> ORGANISM: Artificial
<220> FEATURE:
<223> OTHER INFORMATION: peptide

<400> SEQUENCE: 53

Val Phe Trp Leu Ile Gln Ile Ser Val
1               5

<210> SEQ ID NO 54
<211> LENGTH: 9
<212> TYPE: PRT
<213> ORGANISM: Artificial
<220> FEATURE:
<223> OTHER INFORMATION: peptide

<400> SEQUENCE: 54

Ser Arg Val Phe Ile Ala Thr His Phe
1               5

<210> SEQ ID NO 55
<211> LENGTH: 9
<212> TYPE: PRT
<213> ORGANISM: Artificial
<220> FEATURE:
<223> OTHER INFORMATION: peptide

<400> SEQUENCE: 55

Ala Thr His Phe Pro His Gln Val Ile
1               5

<210> SEQ ID NO 56
```

```
<211> LENGTH: 9
<212> TYPE: PRT
<213> ORGANISM: Artificial
<220> FEATURE:
<223> OTHER INFORMATION: peptide

<400> SEQUENCE: 56

Thr His Phe Pro His Gln Val Ile Leu
1               5

<210> SEQ ID NO 57
<211> LENGTH: 9
<212> TYPE: PRT
<213> ORGANISM: Artificial
<220> FEATURE:
<223> OTHER INFORMATION: peptide

<400> SEQUENCE: 57

Phe Glu His Thr Pro Gly Val His Met
1               5

<210> SEQ ID NO 58
<211> LENGTH: 9
<212> TYPE: PRT
<213> ORGANISM: Artificial
<220> FEATURE:
<223> OTHER INFORMATION: peptide

<400> SEQUENCE: 58

Thr Pro Gly Val His Met Ala Ser Leu
1               5

<210> SEQ ID NO 59
<211> LENGTH: 9
<212> TYPE: PRT
<213> ORGANISM: Artificial
<220> FEATURE:
<223> OTHER INFORMATION: peptide

<400> SEQUENCE: 59

His Met Ala Ser Leu Ser Val Tyr Leu
1               5

<210> SEQ ID NO 60
<211> LENGTH: 9
<212> TYPE: PRT
<213> ORGANISM: Artificial
<220> FEATURE:
<223> OTHER INFORMATION: peptide

<400> SEQUENCE: 60

Leu Ser Val Tyr Leu Lys Thr Asn Val
1               5

<210> SEQ ID NO 61
<211> LENGTH: 9
<212> TYPE: PRT
<213> ORGANISM: Artificial
<220> FEATURE:
<223> OTHER INFORMATION: peptide

<400> SEQUENCE: 61

Tyr Leu Lys Thr Asn Val Phe Leu Phe
1               5

<210> SEQ ID NO 62
<211> LENGTH: 9
<212> TYPE: PRT
```

```
<213> ORGANISM: Artificial
<220> FEATURE:
<223> OTHER INFORMATION: peptide

<400> SEQUENCE: 62

Leu Phe Ala Leu Gly Phe Tyr Leu Leu
1               5

<210> SEQ ID NO 63
<211> LENGTH: 9
<212> TYPE: PRT
<213> ORGANISM: Artificial
<220> FEATURE:
<223> OTHER INFORMATION: peptide

<400> SEQUENCE: 63

Phe Ala Leu Gly Phe Tyr Leu Leu Leu
1               5

<210> SEQ ID NO 64
<211> LENGTH: 9
<212> TYPE: PRT
<213> ORGANISM: Artificial
<220> FEATURE:
<223> OTHER INFORMATION: peptide

<400> SEQUENCE: 64

Leu Gly Phe Tyr Leu Leu Leu Arg Leu
1               5

<210> SEQ ID NO 65
<211> LENGTH: 9
<212> TYPE: PRT
<213> ORGANISM: Artificial
<220> FEATURE:
<223> OTHER INFORMATION: peptide

<400> SEQUENCE: 65

Lys Tyr Asn Ile Ala Asn Trp Phe Leu
1               5

<210> SEQ ID NO 66
<211> LENGTH: 9
<212> TYPE: PRT
<213> ORGANISM: Artificial
<220> FEATURE:
<223> OTHER INFORMATION: peptide

<400> SEQUENCE: 66

Phe Gly Ile Asp Leu Leu Trp Ser Val
1               5

<210> SEQ ID NO 67
<211> LENGTH: 9
<212> TYPE: PRT
<213> ORGANISM: Artificial
<220> FEATURE:
<223> OTHER INFORMATION: peptide

<400> SEQUENCE: 67

Trp Ser Val Phe Trp Leu Ile Gln Ile
1               5

<210> SEQ ID NO 68
<211> LENGTH: 9
<212> TYPE: PRT
<213> ORGANISM: Artificial
<220> FEATURE:
```

<223> OTHER INFORMATION: peptide

<400> SEQUENCE: 68

Lys Trp Cys Ala Asn Pro Asp Trp Ile
1               5

<210> SEQ ID NO 69
<211> LENGTH: 9
<212> TYPE: PRT
<213> ORGANISM: Artificial
<220> FEATURE:
<223> OTHER INFORMATION: peptide

<400> SEQUENCE: 69

Cys Ala Asn Pro Asp Trp Ile His Ile
1               5

<210> SEQ ID NO 70
<211> LENGTH: 9
<212> TYPE: PRT
<213> ORGANISM: Artificial
<220> FEATURE:
<223> OTHER INFORMATION: peptide

<400> SEQUENCE: 70

Pro Phe Ala Gly Leu Val Arg Asn Leu
1               5

<210> SEQ ID NO 71
<211> LENGTH: 9
<212> TYPE: PRT
<213> ORGANISM: Artificial
<220> FEATURE:
<223> OTHER INFORMATION: peptide

<400> SEQUENCE: 71

Gly Leu Val Arg Asn Leu Gly Val Leu
1               5

<210> SEQ ID NO 72
<211> LENGTH: 9
<212> TYPE: PRT
<213> ORGANISM: Artificial
<220> FEATURE:
<223> OTHER INFORMATION: peptide

<400> SEQUENCE: 72

Arg Asn Leu Gly Val Leu Phe Gly Leu
1               5

<210> SEQ ID NO 73
<211> LENGTH: 9
<212> TYPE: PRT
<213> ORGANISM: Artificial
<220> FEATURE:
<223> OTHER INFORMATION: peptide

<400> SEQUENCE: 73

Val Leu Phe Gly Leu Gly Phe Ala Ile
1               5

<210> SEQ ID NO 74
<211> LENGTH: 9
<212> TYPE: PRT
<213> ORGANISM: Artificial
<220> FEATURE:
<223> OTHER INFORMATION: peptide

```
<400> SEQUENCE: 74

Leu Gly Phe Ala Ile Asn Ser Glu Met
1               5

<210> SEQ ID NO 75
<211> LENGTH: 9
<212> TYPE: PRT
<213> ORGANISM: Artificial
<220> FEATURE:
<223> OTHER INFORMATION: peptide

<400> SEQUENCE: 75

Gly Phe Ala Ile Asn Ser Glu Met Phe
1               5

<210> SEQ ID NO 76
<211> LENGTH: 9
<212> TYPE: PRT
<213> ORGANISM: Artificial
<220> FEATURE:
<223> OTHER INFORMATION: peptide

<400> SEQUENCE: 76

Phe Ala Ile Asn Ser Glu Met Phe Leu
1               5

<210> SEQ ID NO 77
<211> LENGTH: 9
<212> TYPE: PRT
<213> ORGANISM: Artificial
<220> FEATURE:
<223> OTHER INFORMATION: peptide

<400> SEQUENCE: 77

Cys Gln Gly Glu Asn Gly Thr Lys Pro
1               5

<210> SEQ ID NO 78
<211> LENGTH: 9
<212> TYPE: PRT
<213> ORGANISM: Artificial
<220> FEATURE:
<223> OTHER INFORMATION: peptide

<400> SEQUENCE: 78

Gly Thr Lys Pro Ser Phe Arg Leu Leu
1               5

<210> SEQ ID NO 79
<211> LENGTH: 9
<212> TYPE: PRT
<213> ORGANISM: Artificial
<220> FEATURE:
<223> OTHER INFORMATION: peptide

<400> SEQUENCE: 79

Ser Phe Arg Leu Leu Cys Ala Leu Thr
1               5

<210> SEQ ID NO 80
<211> LENGTH: 9
<212> TYPE: PRT
<213> ORGANISM: Artificial
<220> FEATURE:
<223> OTHER INFORMATION: peptide

<400> SEQUENCE: 80
```

Arg Leu Leu Cys Ala Leu Thr Ser Leu
1               5

<210> SEQ ID NO 81
<211> LENGTH: 9
<212> TYPE: PRT
<213> ORGANISM: Artificial
<220> FEATURE:
<223> OTHER INFORMATION: peptide

<400> SEQUENCE: 81

Cys Ala Leu Thr Ser Leu Thr Thr Met
1               5

<210> SEQ ID NO 82
<211> LENGTH: 9
<212> TYPE: PRT
<213> ORGANISM: Artificial
<220> FEATURE:
<223> OTHER INFORMATION: peptide

<400> SEQUENCE: 82

Leu Thr Ser Leu Thr Thr Met Gln Leu
1               5

<210> SEQ ID NO 83
<211> LENGTH: 9
<212> TYPE: PRT
<213> ORGANISM: Artificial
<220> FEATURE:
<223> OTHER INFORMATION: peptide

<400> SEQUENCE: 83

Thr Ser Leu Thr Thr Met Gln Leu Tyr
1               5

<210> SEQ ID NO 84
<211> LENGTH: 9
<212> TYPE: PRT
<213> ORGANISM: Artificial
<220> FEATURE:
<223> OTHER INFORMATION: peptide

<400> SEQUENCE: 84

Met Gln Leu Tyr Arg Phe Ile Lys Ile
1               5

<210> SEQ ID NO 85
<211> LENGTH: 9
<212> TYPE: PRT
<213> ORGANISM: Artificial
<220> FEATURE:
<223> OTHER INFORMATION: peptide

<400> SEQUENCE: 85

Arg Phe Ile Lys Ile Pro Thr His Ala
1               5

<210> SEQ ID NO 86
<211> LENGTH: 9
<212> TYPE: PRT
<213> ORGANISM: Artificial
<220> FEATURE:
<223> OTHER INFORMATION: peptide

<400> SEQUENCE: 86

Lys Ile Pro Thr His Ala Glu Pro Leu
1               5

<210> SEQ ID NO 87
<211> LENGTH: 9
<212> TYPE: PRT
<213> ORGANISM: Artificial
<220> FEATURE:
<223> OTHER INFORMATION: peptide

<400> SEQUENCE: 87

Thr His Ala Glu Pro Leu Phe Tyr Leu
1               5

<210> SEQ ID NO 88
<211> LENGTH: 9
<212> TYPE: PRT
<213> ORGANISM: Artificial
<220> FEATURE:
<223> OTHER INFORMATION: peptide

<400> SEQUENCE: 88

His Ala Glu Pro Leu Phe Tyr Leu Leu
1               5

<210> SEQ ID NO 89
<211> LENGTH: 9
<212> TYPE: PRT
<213> ORGANISM: Artificial
<220> FEATURE:
<223> OTHER INFORMATION: peptide

<400> SEQUENCE: 89

Leu Ser Phe Cys Lys Ser Ala Ser Ile
1               5

<210> SEQ ID NO 90
<211> LENGTH: 9
<212> TYPE: PRT
<213> ORGANISM: Artificial
<220> FEATURE:
<223> OTHER INFORMATION: peptide

<400> SEQUENCE: 90

Ser Phe Cys Lys Ser Ala Ser Ile Pro
1               5

<210> SEQ ID NO 91
<211> LENGTH: 9
<212> TYPE: PRT
<213> ORGANISM: Artificial
<220> FEATURE:
<223> OTHER INFORMATION: peptide

<400> SEQUENCE: 91

Cys Lys Ser Ala Ser Ile Pro Leu Met
1               5

<210> SEQ ID NO 92
<211> LENGTH: 9
<212> TYPE: PRT
<213> ORGANISM: Artificial
<220> FEATURE:
<223> OTHER INFORMATION: peptide

<400> SEQUENCE: 92

Ser Ile Pro Leu Met Val Val Ala Leu
1               5

```
<210> SEQ ID NO 93
<211> LENGTH: 9
<212> TYPE: PRT
<213> ORGANISM: Artificial
<220> FEATURE:
<223> OTHER INFORMATION: peptide

<400> SEQUENCE: 93

Ile Pro Leu Met Val Val Ala Leu Ile
1               5

<210> SEQ ID NO 94
<211> LENGTH: 9
<212> TYPE: PRT
<213> ORGANISM: Artificial
<220> FEATURE:
<223> OTHER INFORMATION: peptide

<400> SEQUENCE: 94

Ala Leu Ile Pro Tyr Cys Val His Met
1               5

<210> SEQ ID NO 95
<211> LENGTH: 11
<212> TYPE: PRT
<213> ORGANISM: Artificial
<220> FEATURE:
<223> OTHER INFORMATION: peptide

<400> SEQUENCE: 95

Arg Asp Ser Gly Gly Ser Asn Ala Lys Leu Thr
1               5                   10

<210> SEQ ID NO 96
<211> LENGTH: 12
<212> TYPE: PRT
<213> ORGANISM: Artificial
<220> FEATURE:
<223> OTHER INFORMATION: peptide

<400> SEQUENCE: 96

Arg Glu Ala Gly Thr Gln Val Val Gly Gln Leu Thr
1               5                   10

<210> SEQ ID NO 97
<211> LENGTH: 8
<212> TYPE: PRT
<213> ORGANISM: Artificial
<220> FEATURE:
<223> OTHER INFORMATION: peptide

<400> SEQUENCE: 97

Ser Asp Ala Gln Asn Thr Leu Tyr
1               5

<210> SEQ ID NO 98
<211> LENGTH: 8
<212> TYPE: PRT
<213> ORGANISM: Artificial
<220> FEATURE:
<223> OTHER INFORMATION: prptide

<400> SEQUENCE: 98

Ser Gly Asp Arg Tyr Glu Gln Tyr
1               5

<210> SEQ ID NO 99
<211> LENGTH: 10
```

```
<212> TYPE: PRT
<213> ORGANISM: Artificial
<220> FEATURE:
<223> OTHER INFORMATION: peptide

<400> SEQUENCE: 99

Ser Gly Thr Gly Gly Gln Asn Thr Leu Tyr
1               5                   10
```

ANTIGENS TARGETED BY PREVALENT PATHOGENNIC T CELLS IN TYPE 1 DIABETES AND USES THEREOF

CROSS-REFERENCE TO RELATED APPLICATIONS

This is a U.S. National Phase of PCT Application No. PCT/US2004/015752, filed May 20, 2004, which claims the benefit of U.S. Provisional Application No. 60/471,868, filed May 20, 2003.

STATEMENT OF GOVERNMENT SUPPORT

This invention was made with government support under Grant No. P01 DK52956 awarded by the National Institutes of Health. The government has certain rights in the invention.

BACKGROUND (1) Field of the Invention

The present invention generally relates to diagnosis and therapy of type 1 diabetes. More specifically, the invention provides methods of diagnosis, prevention and therapy of type 1 diabetes based on the identification of the islet (3 cell antigen targeted by pathogenic T cells.

(2) Description of the Related Art

REFERENCES CITED

Aichele, P., D. Kyburz, P. Ohashi, B. Odermatt, R. Zinkernagel, H. Hengartner, and H. Pircher. 1994. Peptide-induced T-cell tolerance to prevent autoimmune diabetes in a transgenic mouse model. Proc. Natl. Acad. Sci. USA. 91:444-448.

Alexander-Miller, M., G. Leggatt, and J. Berzofsky. 1996. Selective expansion of high- or low-avidity cytotoxic T-lymphocytes and efficacy for adoptive immunotherapy. Proc. Natl. Acad. Sci. USA. 93:4102-4107.

J. D. Altman et al., Science 274, 94 (1996).

A. Amrani et al., Nature 406, 739 (2000).

A. Amrani et al., J. Immunol. 167, 655 (2001).

B. Anderson, B. J. Park, J. Verdaguer, A. Amrani, P. Santamaria, Proc. Natl. Acad. Sci. U.S.A. 96, 9311 (1999).

Anderton, S., and D. Wraith. 1998. Hierarchy in the ability of T cell epitopes to induce peripheral tolerance to antigens from myelin. Eur. J. Immunol. 28:1251-1261.

Arden, S., T. Zhan, S. Steegers, S. Webb, B. Bergman, R. O'Brien, and J. Hutton. 1999. Molecular cloning of a pancreatic islet-specific glucose-6-phosphatase catalytic subunit-related protein. Diabetes. 48:531-540.

Arif, S., T. I. Tree, T. P. Astill, J. M. Tremble, A. J. Bishop, C. M. Dayan, B. O. Roep, and M. Peakman. 2004. Autoreactive T cell responses show proinflammatory polarization in diabetes but a regulatory phenotype in health. J Clin Invest. 113:451-463.

S. Baekkeskov et al., Nature 347, 151 (1990).

Bielekova, B., B. Goodwin, N. Richert, I. Cortese, T. Kondo, G. Afshar, B. Gran, J. Eaton, J. Antel, J. Frank, H. McFarland, and R. Martin. 2000. Encephalitogenic potential of the myelin basic protein peptide (amino acids 83-99) in multiple sclerosis: results of a phase II clinical trial with an altered peptide ligand. Nat. Med. 6:1167-1175.

Burke, D. H., L. Scates, K. Andrews, and L. Gold., J. Mol. Biol. 264, 650 (1996).

Cocca, B. A., A. M. Cline, and M. Z. Radic. 2002. Blebs and apoptotic bodies are B cell autoantigens. J. Immunol. 169:159-166.

L. Cox, E. L. Huczko, V. H. Engelhard, J. Shabanowitz, D. F. Hunt, in MHC: A Practical Approach, N. Fernandez, G. Butcher, Eds. (Oxford Univ. Press, New York, 1997), vol. 1, pp. 141.

T. P. DiLorenzo et al., Proc. Natl. Acad. Sci. U.S.A. 95, 12538 (1998).

T. P. DiLorenzo et al., Clin. Immunol. 105, 332 (2002).

Ellington, A. D., and J. W. Szostak, Nature 346,818 (1990).

Gammon et al., Nature (London) 319, 413 (1986).

Gross, D. A., S. Graff-Dubois, P. Opolon, S. Cornet, P. Alves, A. Bennaceur-Griscelli, O. Faure, P. Guillaume, H. Firat, S. Chouaib, F. A. Lemonnier, J. Davoust, I. Miconnet, R. H. Vonderheide, and K. Kosmatopoulos. 2004. High vaccination efficiency of low-affinity epitopes in antitumor immunotherapy. J Clin Invest. 113:425-433.

Group, D.P.T.-T.D.S. 2002. Effects of insulin in relatives of patients with type 1 diabetes mellitus. N. Engl. J. Med. 346:1685-1691.

K. Hamaguchi, H. R. Gaskins, E. H. Leiter, Diabetes 40, 842 (1991).

A. H. Hartemann et al., Clin, Exper. Immunol. 116, 225 (1999).

Hirao, 1., M. Spingola, D. Peabody, and A. D. Ellington, Mol. Divers. 4, 75 (1998).

Jaeger, J., T. Restle, and T. A. Steitz, The EMBO Journal 17, 4535 (1998).

Kappos, L., G. Comi, H. Panitch, J. Oger, J. Antel, P. Conlon, L. Steinman, and T.A.P.L.i.R.M.S. Group. 2000. Induction of a non-encephalitogenic type 2 T helper-cell autoimmune response in multiple sclerosis after administration of an altered peptide ligand in a placebo-controlled, randomized phase II trial. Nat. Med. 6:1176-1182.

Karin, N., D. Mitchell, S. Brocke, N. Ling, and L. Steinman. 1994. Reversal of experimental autoimmune encephalomyelitis by a soluble peptide variant of a myelin basic protein epitope: T cell receptor antagonism and reduction of interferon γ and tumor necrosis factor α production. J. Exp. Med. 180:2227-2237.

J. Karttunen, S. Sanderson, N. Shastri, Proc. Natl. Acad. Sci. U.S.A. 89, 6020 (1992).

Kensch, O., B. A. Connolly, H. J. Steinhoff, A. McGregor, R. S. Goody, and T. Restle, J Biol Chem. 275, 18271 (2000).

R. S. Liblau, F. S. Wong, L. T. Mars, P. Santamaria, Immunity 17, 1 (2002).

Lieberman, S., and T. DiLorenzo. 2003. A comprehensive guide to antibody and T-cell responses in type 1 diabetes. Tissue Antigens. 62:359.

Lieberman, S., A. Evans, B. Han, T. Takaki, Y. Vinnitskaya, J. Caldwell, D. Serreze, J. Shabanowitz, D. Hunt, S, Nathenson, P. Santamaria, and T. DiLorenzo. 2003. Identity of the beta cell antigen targeted by a prevalent population of pathogenic CD8+ T cells in autoimmune diabetes. Proc. Natl. Acad. Sci. USA. 100:8384-8388.

Liu, G., and D. Wraith. 1995. Affinity for class II MHC determines the extent to which soluble peptides tolerize autoreactive T cells in naive and primed adult mice—implications for autoimmunity. Int. Immunol. 7:1255-1263.

S. E. Martin, J. Shabanowitz, D. F. Hunt, J. A. Marto, Anal. Chem. 72, 4266 (2000).

C. C. Martin et al., J. Biol. Chem. 276, 25197 (2001).

McKown, K. et al., 1999. Lack of efficacy of oral bovine type II collagen added to existing therapy in rheumatoid arthritis. Arthritis Rheum. 42:1204-1208.

Metzler, B., and D. Wraith. 1993. Inhibition of experimental autoimmune encephalomyelitis by inhalation but not oral administration of the encephalitogenic peptide: influence of MHC binding affinity. Int. Immunol. 5:1159-1165.

Metzler, B., S. Anderton, S. Manickasingham, and D. Wraith. 2000. Kinetics of peptide uptake and tissue distribution following a single intranasal dose of peptide. Immunol. Invest. 29:61-70.

M. Nagata, P. Santamaria, T. Kawamura, T. Utsugi, J. W. Yoon, J. Immunol. 152, 2042 (1994).

Nicholson, L. B., J. M. Greer, R. A. Sobel, M. B. Lees, and V. K. Kuchroo. 1995. An altered peptide ligand mediates immune deviation and prevents autoimmune encephalomyelitis. Immunity. 3:397-405.

J. P. Palmer et al., Science 222, 1337 (1983).

K. C. Parker, M. A. Bednarek, J. E. Coligan, J. Immunol. 152, 163 (1994).

Perez-Diez, A., P. Spiess, N. Restifo, P. Matzinger, and F. Marincola. 2002. Intensity of the vaccine-elicited immune response determines tumor clearance. J. Immunol. 168: 338-347.

R. A. Pierce et al., J. Immunol. 163, 6360 (1999).

M. J. Pittet et al., Trends. Immunol. 23, 325 (2002).

F. Pociot, M. F. McDermott, Genes Immun. 3, 235 (2002).

Pozzilli, P. et al., 2000. No effect of oral iinsulin on residual beta-cell function in recent-onset type 1 diabetes (the IMDIAB VII). IMDIAB Group. Diabetologia. 43:1000-1004.

Princiotta, M. F., D. Finzi, S. B. Qian, J. Gibbs, S. Schuchmann, F. Buttgereit, J. R. Bennink, and J. W. Yewdell. 2003. Quantitating protein synthesis, degradation, and endogenous antigen processing. Immunity. 18:343-354.

D. U. Rabin, S. M. Pleasic, R. Palmer-Crocker, J. A. Shapiro, Diabetes 41, 183 (1992).

H. Rammensee, J. Bachmann, N. P. Emmerich, O. A. Bachor, S. Stevanovic, Immunogenetics 50, 213 (1999).

P. A. Reche, J. P. Glutting, E. L. Reinherz, Hum. Immunol. 63, 701 (2002).

Santamaria, P. 2001. Effector lymphocytes in autoimmunity. Curr. Opin Immunol. 13:663-669.

P. Santamaria et al., J. Immunol. 154, 2494 (1995).

Sauter, B., M. L. Albert, L. Francisco, M. Larsson, S. Somersan, and N. Bhardwaj. 2000. Consequences of cell death. Exposure To necrotic tumor cells, but not primary tissue cells or apoptotic cells, induces the maturation of immunostimulatory dendritic cells. J Exp Med. 191:423-434.

Schneider, D. J., J. Feigon, Z. Hostomsky, and L. Gold, Biochemistry 34, 9599 (1995).

D. V. Serreze, E. H. Leiter, Curr. Dir. Autoimmun. 4, 31 (2001).

D. V. Serreze et al., Diabetes 50, 1992 (2001).

M. Terajima et al., J. Exp. Med. 197, 927 (2003).

R. Tisch, H. McDevitt, Cell 85, 291 (1996).

Toes, R., R. Offring a, R. Blom, C. Melief, and W. Kast. 1996. Peptide vaccination can lead to enhanced tumor growth through specific T-cell tolerance induction. Proc. Natl. Acad. Sci. USA. 93:7855-7860.

Trentham, D. et al., 1993. Effects of oral administration of type II collagen on rheumatoid arthritis. Science. 261: 1727-1730.

J. D. Trudeau et al., J. Clin. Invest. 111, 217 (2003).

Tuerk, C., and L. Gold, Proc. Natl. Acad. Sci. USA 89:6988 (1992).

Tuerk, C., and L. Gold, Science 249:505 (1990).

F. S. Wong et al., Nat. Med. 9, 1026 (1999).

F. S. Wong, A. K. Moustakas, L. Wen, G. K. Papadopoulos, C. A. Janeway, Jr., Proc. Natl. Acad. Sci. U.S.A. 99, 5551 (2002).

Verdaguer, J., J.-W. Yoon, B. Anderson, N. Averill, T. Utsugi, B. Park, and P. Santamaria. 1996. Acceleration of spontaneous diabetes in TCR-β-transgenic nonobese diabetic mice by (3-cell cytotoxic CD8+ T cells expressing identical endogenous TCR-α chains. J. Immunol. 157:4726-4735.

J. Verdaguer et al., J. Exp. Med. 186, 1663 (1997).

Weiner, H. 1993. Double-blind pilot trial of oral tolerization with myelin antigens in multiple sclerosis. Science. 259: 1321-1324.

Wraith, D. C., D. E. Smilek, D. J. Mitchell, L. Steinman, and H. O. McDevitt. 1989. Antigen recognition in autoimmune encephalomyelitis and the potential for peptide-mediated immunotherapy. Cell 59:247-255.

Zeh, H., D. Perry-Lalley, M. Dudley, S. Rosenberg, and J. Yang. 1999. High avidity CTLS for two self-antigens demonstrate superior in vitro and in vivo anti-tumor efficacy. J. Immunol. 162:989-994.

Zhang, Y., B. O'Brien, J. Trudeau, R. Tan, P. Santamaria, and J. P. Dutz. 2002. In situ β-cell death promotes priming of diabetogenic CD8 T lymphocytes. J. Immunol. 168:1466-1472.

U.S. Pat. No. 5,472,841.
U.S. Pat. No. 5,496,938.
U.S. Pat. No. 5,503,978.
U.S. Pat. No. 5,567,588.
U.S. Pat. No. 5,580,737.
U.S. Pat. No. 5,582,981.
U.S. Pat. No. 5,637,459.
U.S. Pat. No. 5,654,151.
U.S. Pat. No. 5,683,867.
U.S. Pat. No. 5,705,337.
U.S. Pat. No. 5,712,375.
U.S. Pat. No. 5,726,017.
U.S. Pat. No. 5,773,598.
U.S. Pat. No. 5,786,462.
U.S. Pat. No. 6,028,186.
U.S. Pat. No. 6,083,696.
U.S. Pat. No. 6,110,900.
U.S. Pat. No. 6,124,449.
U.S. Pat. No. 6,127,119.
U.S. Pat. No. 6,140,490.
U.S. Pat. No. 6,147,204.
U.S. Pat. No. 6,168,778.
U.S. Pat. No. 6,171,795.

The NOD mouse is a widely studied model of human type 1 diabetes, an autoimmune disease characterized by inflammation of pancreatic islets (insulitis) followed by T cell-mediated destruction of the insulin-producing β cells (Serreze & Leiter, 2001). Both CD4+ and CD8+ T cells are required for this pathogenic process (Serreze & Leiter, 2001); however, CD8+ T cells appear to be responsible for the initial β cell insult (Serreze & Leiter, 2001; Tisch & McDevitt, 1996; DiLorenzo et al., 1998). While the pathogenicity of B cells and autoantibodies is less clear, the autoantigens currently believed to contribute to autoimmune diabetes pathogenesis in NOD mice and humans were all originally identified based on the presence of specific autoantibodies rather than by T cell recognition (Palmer et al., 1983; Baekkeskov et al., 1990; Rabin et al., 1992). Little is known of the (3 cell antigens targeted by the pathogenic CD8+ T cells. While one study identified an insulin peptide as the antigenic target of the majority of islet-infiltrating CD8+ T cells in NOD mice (Wong et al., 1999), the prevalence of these insulin-reactive CD8+ T cells was not confirmed in subsequent studies (Amrani et al., 2000; Trudeau et al., 2003). A substantial proportion of β cell-autoreactive CD8+ T cells isolated from NOD islets express a shared T cell receptor (TCR) α chain (Vα17-Jα42), suggesting recognition of a common β cell peptide (DiLorenzo et al., 1998; Santamaria et al., 1995). These T cells do not recognize the antigenic insulin peptide mentioned above (Anderson et al., 1999; Serreze et al., 2001). The pathogenicity of this prevalent T cell population has been well established through studies of the 8.3 T cell clone (a representative T cell clone of the Vα17-Jα42-expressing T cell population) (Amrani et al., 2000; Trudeau et al., 2003; Anderson et al., 1999; Nagata et al., 1994; Verdaguer et al., 1997). 8.3-like T cells are present in the earliest islet infiltrates of NOD mice (DiLorenzo et al., 1998) and undergo avidity maturation as islet inflammation progresses to overt disease (Amrani et al., 2000). At any given time, 8.3-like T cells can constitute up to 30-40% of the islet-associated CD8+ T cells (Trudeau et al., 2003). Additionally, quantitation of 8.3-like T cells in peripheral blood predicts diabetes development in individual NOD mice (Trudeau et al., 2003), unlike any other single immune indicator identified to date. While the prevalence and pathogenicity of 8.3-like T cells has been clearly established, the identity of their ligand has remained elusive. The 8.3 T cell clone is restricted to the class I major histocompatibility complex (MHC) molecule H-2K$^d$ (Nagata et al., 1994). The artificial oligopeptides NRP-V7 and NRP-A7 have previously been shown to bind to 8.3-like T cells in the context of H-2K$^d$ molecules (Anderson et al., 1999; Amrani et al., 2001). However, those studies do not suggest the identity of the natural 8.3-like T cell ligand responsible for type 1 diabetes autoimmunity.

The determination of the 8.3-like T cell ligand, as well as other T cell ligands associated with type 1 diabetes is thus desirable since it would open up new options for diagnosis, prevention and therapy of that disease. A characterization of the precise role of these ligands in type 1 diabetes pathogenesis is also needed. This invention satisfies these needs.

SUMMARY OF THE INVENTION

Accordingly, the inventors have succeeded in identifying the 8.3-like T cell ligand present on f3 cells that is responsible for type 1 diabetes. That ligand is islet-specific glucose-6-phosphatase catalytic subunit-related protein (IGRP), and its CD8+ T cell-binding peptide comprising amino acids 206-214 of the IGRP sequence (SEQ ID NO:1 for mice; SEQ ID NO:2 for humans). The inventors have also identified several other CD8+ T cell ligands from IGRP that contribute to type 1 diabetes, particularly when T cells reacting to IGRP$_{206-214}$ are eliminated with a high affinity ligand, for example IGRP$_{206-214}$.

Thus, in some embodiments, the invention is directed to isolated and purified oligopeptides or polypeptides less than 355 amino acids comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(LN)(F/L)(G/N)IDLL (SEQ ID NO:6), KWCANPDWI (SEQ ID NO:7), and SFCKSASIP (SEQ ID NO:8).

In other embodiments, the present invention is directed to isolated and purified oligopeptides or polypeptides comprising at least one of the above sequences in a sterile pharmaceutical preparation.

Additionally, the present invention is directed to isolated and purified oligopeptides 8-10 amino acids in length, completely homologous with a mammalian IGRP having at least 90% homology to SEQ ID NO:1 or SEQ ID NO:2, wherein the oligopeptide is capable of binding a human MHC class I molecule.

The present invention is also directed to antisense molecules complementary to at least a portion of an mRNA encoding a mammalian IGRP at least 90% homologous to SEQ ID NO:1 or SEQ ID NO:2. In these embodiments, the antisense molecules are capable of inhibiting translation of a mammalian IGRP.

In related embodiments, the invention is directed to ribozymes specific for a portion of an mRNA encoding a mammalian IGRP at least 90% homologous to SEQ ID NO:1 or SEQ ID NO:2. The ribozymes of these embodiments inhibit translation of a mammalian IGRP.

In other related embodiments, the invention is directed to RNAi molecules homologous to a portion of an mRNA encoding a mammalian IGRP at least 90% homologous SEQ ID NO:1 or SEQ ID NO:2. In these embodiments, the RNAi molecule is capable of inhibiting translation of a mammalian IGRP.

The invention is also directed to methods of treating a mammal that is at risk for or has type I diabetes. The methods comprise administering an oligopeptide to the mammal in a manner sufficient to reduce CD8+ T cells reactive to IGRP. In these methods, the oligopeptide is 8-10 amino acids in length and comprises a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21).

In further embodiments, the invention is directed to other methods of treating a mammal that is at risk for or has type 1 diabetes. These additional methods comprise administering an oligopeptide to the mammal in a manner sufficient to reduce CD8+ T cells reactive to IGRP. In these methods, the oligopeptide is 8-10 amino acids in length, completely homologous with a mammalian IGRP, and capable of binding an MHC class 1 molecule of the mammal.

The invention is further directed to additional methods of treating a mammal that is at risk for or has type 1 diabetes. The methods comprise administering to the mammal an oligopeptide 8-10 amino acids in length, wherein the oligopeptide is a medium- or low-affinity ligand to an IGRP$_{206-214}$-reactive CD8+ T cell.

Additionally, the invention is directed to methods of preventing a CD8+ T cell that is cytotoxic to pancreatic islet β-cells from destroying a β-cell. The methods comprise treating the n-cell with a compound capable of specifically binding an oligopeptide 8-10 amino acids in length, and completely homologous with a mammalian IGRP having at least 90% homology to SEQ ID NO:1 or SEQ ID NO:2. In these methods, the oligopeptide is capable of binding an MHC class I molecule of the mammal.

The invention is also directed to other methods of preventing a CD8+ T cell that is cytotoxic to pancreatic islet β-cells from destroying a β-cell. The methods comprise treating the CD8+ T cell with an oligopeptide of 8-10 amino acids comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21), and an MHC class I molecule that is capable of binding the oligopeptide.

In related embodiments, the invention is directed to additional methods of preventing a CD8+ T cell that is cytotoxic to pancreatic islet β-cells from destroying a β-cell. The methods comprise treating the CD8+ T cell with an oligopeptide in a manner sufficient to prevent binding of the CD8+ T cell to IGRP. In these methods, the oligopeptide is 8-10 amino acids in length and comprises a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21).

In additional embodiments, the invention is directed to other methods of treating a mammal at risk for type 1 diabetes. These methods comprise administering to the mammal an antisense molecule, a ribozyme, or an RNAi molecule. In these embodiments, the antisense molecule, the ribozyme, and the RNAi molecule are capable of specifically inhibiting translation of a mammalian IGRP.

The present invention is also directed to additional methods of treating a mammal having type 1 diabetes. The methods comprise transplanting pancreatic islet β-cells into the pancreas of the mammal. In these embodiments, the β-cells are transfected with a vector that expresses an antisense molecule, a ribozyme, or an RNAi molecule that is capable of specifically inhibiting translation of a mammalian IGRP.

The invention is also directed to methods for determining whether a mammal is at risk for or has type 1 diabetes. The methods comprise determining the presence of CD8+ T cells reactive to IGRP in the mammal by obtaining a sample of lymphocytes comprising CD8+ T cells from the mammal, combining the lymphocytes with an oligopeptide, and determining whether any CD8+ T cells specifically bind to the oligopeptide. In these methods, the oligopeptide is 8-10 amino acids in length and comprises a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21). Additionally, the oligopeptide or the MHC molecule further comprises a detectable label. In these methods, CD8+ T cell binding to the oligopeptide indicates that the mammal is at risk for or has type 1 diabetes.

In related embodiments, the invention is directed to other methods for determining whether a mammal is at risk for or has type 1 diabetes. The methods comprise determining the presence of CD8+ T cells reactive to IGRP in the mammal by obtaining a sample of lymphocytes comprising CD8+ T cells from the mammal, combining the lymphocytes with an oligopeptide of 8-10 amino acids that is completely homologous with a mammalian IGRP, and an MHC class I molecule that is capable of binding the oligopeptide, where the oligopeptide or the MHC molecule further comprises a detectable label, and determining whether any CD8+ T cells specifically bind to the oligopeptide. In these methods, CD8+ T cell binding to the oligopeptide indicates that the mammal is at risk for or has type 1 diabetes.

DETAILED DESCRIPTION OF THE INVENTION

Figure 1:
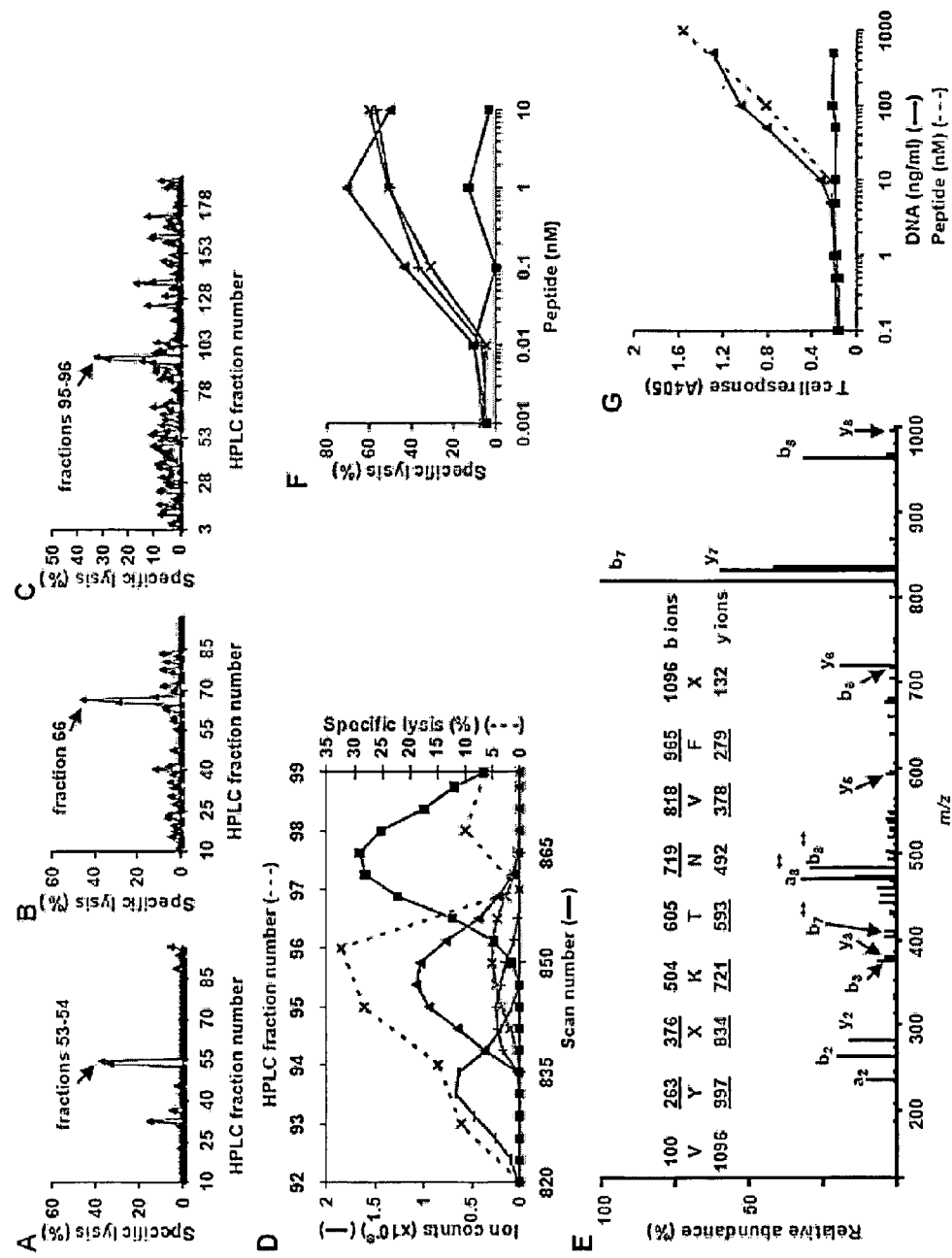
FIG. 1 is graphs of experimental data establishing the identification of $IGRP_{206-214}$ as the natural β cell peptide recognized by the pathogenic T cell clone 8.3. Panels A to C. Epitope reconstitution activity of first-(A), second-(B), and third-dimension (C) HPLC fractions of $H-2K^d$-eluted NIT-1 peptides. RMAS/$K^d$ cells were pulsed with peptide fractions and used as targets in $^{51}Cr$-release assays with 8.3 CTL as effectors (15). Panel D. Determination of candidate peptides by correlation of ion abundance curves (plotted on the left and bottom axes) with epitope reconstitution activity of third-dimension HPLC fractions (right and top axes). Peptide m/z values are indicated in the key. Panel E. Collision-activated dissociation (CAD) mass spectrum of candidate peptide $(M+2H)^{+2}$ ion with monoisotopic m/z of 548.845. X represents I or L. Ions observed in the spectrum are underlined; the b ions originate from the N-terminus of the peptide and the y ions from the C-terminus. Panel F. Recognition of VYLKTNVFL (SEQ ID NO:19) ($IGRP_{206-214}$) by 8.3 CTL. RMA-S/$K^d$ cells were pulsed with the indicated peptides and used as targets in $^{51}Cr$-release assays with 8.3 CTL as effectors. Panel G. Verification of IGRP as the source of the natural antigenic peptide recognized by 8.3 CTL. COS-7 cells were transfected with varying concentrations of an IGRP expression construct, or vector alone, together with 10 ng/ml of an $H-2K^d$ expression construct (solid lines). Separate cultures were transfected with the $H-2K^d$ construct alone and pulsed with varying concentrations of $IGRP_{206-214}$ peptide (broken line). Following co-culture with 8.3 CTL, T cell response was measured as IFN-γ-release by ELISA and is presented as absorbance at 405 nm (A405).

The present invention is based on the identification of the 8.3-like T cell ligand present on β cells that is responsible for type 1 diabetes. As established by the research described in Example 1, the ligand is islet-specific glucose-6-phosphatase catalytic subunit-related protein (IGRP), and its predominant CD8$^+$ T cell-binding peptide comprising amino acids 206-214 of the IGRP sequence, having the sequence VYLKTNVFL (SEQ ID NO:19) in the mouse, using the commonly accepted single letter amino acid abbreviations. Other mouse IGRP peptides capable of binding CD8$^+$ T cells that are involved in the pathology of type 1 diabetes are FLWSVFWLI (SEQ ID NO:4) (amino acids 152-160); TYYGFLNFM (SEQ ID NO:9) (21-29); LRLFGIDLL (SEQ ID NO:10) (225-233); KWCANPDWI (SEQ ID NO:7) (241-249) and SFCKSASIP (SEQ ID NO:8) (324-332). See Examples 3 and 4.

As used herein, an IGRP amino acid sequence includes any naturally occurring mammalian amino acid sequence that is islet specific and is at least 90% identical to SEQ ID NO:1 (Mouse IGRP, from GenBank NP 067306) or SEQ ID NO:2 (Human IGRP, from GenBank NP 066999). The IGRP mouse and human amino acid sequences are not limited to SEQ ID NO:1 and SEQ ID NO:2, respectively, but includes any variants naturally present in mice or humans. The identification of any mammalian IGRP amino acid sequence can be readily made without undue experimentation, e.g., by identifying mRNA sequences limited to islet cells that are highly (i.e., >90%) homologous to already-identified mRNA sequences of mouse or human IGRP (e.g., as found in GenBank accessions NP 021331 and NP 021176, respectively), and determining the amino acid sequence of the expressed protein.

As further discussed in Example I, the mouse IGRP$_{206-214}$ peptide has the sequence VYLKTNVFL(SEQ ID NO:19). The analogous human sequence, from GenBank NP 066999, is TYLKTNLFL (SEQ ID NO:22). Thus, the mouse and human sequences differ at the first (V vs. T) and seventh position (V vs. L). It is also known that the oligopeptide sequences KYNKANVFL (SEQ ID NO:11) (NRP-V7) and KYNKANAFL (SEQ ID NO:12) (NRP-A7) are additional 8.3-like T cell ligands (Anderson et al., 1999; Amrani et al., 2001). These differ from the naturally occurring mouse and human sequences at the first, third, fifth, and seventh positions. The differences among these sequences at the first position is not conservative, since V (Val) is nonpolar, T (Thr) is polar, and K (Lys) is positively charged. This indicates that the first position of these peptides do not contribute to 8.3 T cell binding. However, the three different amino acids at the seventh position, V (Val), L (Leu) and A (Ala), are all nonpolar, indicating that a nonpolar residue is required for that position in order to retain 8.3 T cell binding. Therefore, one can conclude that an oligopeptide having the naturally-conserved sequence YLKTN(A/I/L/V)FL (SEQ ID NO:3) are 8.3 T cell ligands. As used herein, (A/I/L/V) signifies that the amino acid at that position can be any of the non-polar amino acids A, 1, L or V. Since the mouse H-2K$^d$ class I molecule is known to require at least a 9-mer, at least nine amino acids is preferred where mouse MHC molecules and T cells are utilized. A Blast search revealed that none of the 8-mers are present in any known amino acid sequence, except for IGRP.

With regard to the other IGRP peptides identified as capable of binding CD8$^+$ T cells, peptides 152-160 (FLWSVFWLI) (SEQ ID NO:4), 241-249 (KWCANPDWI) (SEQ ID NO:7), and 324-332 (SFCKSASIP) (SEQ ID NO:8) are identical in humans and mice. However, peptides 21-29 and 225-233 are different in mice and humans. Peptide 21-29 is TYYGFKNFM (SEQ ID NO:52) in mice and AYYTFLNFM (SEQ ID NO:23) in humans, and peptide 225-231 is LRLFGIDLL (SEQ ID NO:10) in mice and LRVLNIDLL (SEQ ID NO:24) in humans. The human peptides would also be expected to be capable of binding CD8$^+$ T cells.

Thus, in some embodiments, the present invention is directed to isolated and purified oligopeptides or polypeptides less than 355 amino acids comprising comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8). These oligopeptides and polypeptides are also useful in that they are CD8$^+$ T cell ligands comprising peptide sequences involved in type 1 diabetes and are thus useful for diagnostic or therapeutic applications.

As used herein, "isolated and purified" means present in a greater concentration than would be found in nature. Preferably, an isolated and purified oligopeptide or polypeptide is at least about 10% of the peptide component of the preparation; more preferably at least about 25%; even more preferably at least about 50%; still more preferably at least about 75%; and most preferably at least about 90% of the peptide component of a preparation.

In preferred embodiments, these oligopeptides or polypeptides are completely homologous to a mammalian IGRP (e.g., mouse and human) having at least 90% homology to SEQ ID NO:1 or SEQ ID NO:2. In other preferred embodiments, the oligopeptides or polypeptides comprise 100 amino acids or less, more preferably 25 amino acids or less, even more preferably 13-25 amino acids, and most preferably 8-10 amino acids, since CD8$^+$ T cells generally only bind oligopeptides of 8-10 amino acids.

In these embodiments, preferred polypeptides or oligopeptides comprise the above peptides having the sequences that VYLKTNVFL(SEQ ID NO:19) or TYLKTNLFL (SEQ ID NO:22), since those sequences are present in the naturally occurring IGRP from mice and humans, respectively.

In further aspects of these embodiments, the oligopeptide or polypeptide also comprises an antigenic carrier, in order to more effectively use the peptides in immunization protocols, to tolerize a mammal to IGRP, preventing development of type 1 diabetes, as was achieved in the experiment described in Example 2. A nonlimiting example of an antigenic carrier is incomplete Freund's adjuvant. See also Gammon et al., 1986.

In other aspects, the oligopeptide or polypeptide further comprises a detectable label. Such labeled peptides are useful in diagnostic protocols, e.g., to determine the presence of 8.3-like CD8$^+$ T cells, to identify a mammal that has, or is at risk for, type 1 diabetes. The invention is not limited to any particular detectable label, and the skilled artisan can select a label most appropriate for any particular application without undue experimentation. Examples include a fluorescent moiety, a radioactive molecule, and an assayable enzyme (e.g., β-galactosidase or streptavidin). Methods for labeling peptides with any of these detectable moieties are well known.

In further aspects, the above-identified oligopeptides of 8-10 amino acids can be usefully combined with an MHC class I molecule that is capable of binding the oligopeptide, for example a mouse H-2K$^d$ molecule, which binds the IGRP$_{206-214}$. An MHC class I molecule for any of the other peptides can be identified using methods known in the art. Since CD8$^+$ T cells only bind to an antigen in the context of an MHC class I molecule, the oligopeptide-MHC class I mixtures are useful for creating a T cell ligand. The MHC class I molecules are preferably employed in the form of tetramers. See, e.g., Altman et al., 1996; Trudeau et al., 2003. In some applications, e.g., diagnostics, the oligopeptide of the oligopeptide-MHC class I mixtures further comprises a detectable label, such as those previously discussed, i.e., conjugated to the oligopeptide. Alternatively or additionally, the MHC class I molecule could employ a detectable label.

In some methods of treatment, directed toward eliminating CD8$^+$ T cells, the oligopeptide or the MHC class I molecule can also include a cytotoxic molecule. In these methods, the cytotoxic oligopeptide-MHC class I mixture binds to the 8.3-like T cell, where the cytotoxic molecule kills the T cell.

The invention is not narrowly limited to any particular cytotoxic molecule that is bound to the oligopeptide or MHC class I molecule. The skilled artisan could identify various cytotoxic molecules useful in these aspects, and could select the appropriate cytotoxic molecule for any particular application without undue experimentation. Examples of potentially useful cytotoxic molecules include radioactive molecules (e.g., $^{131}$I, $^{90}$Y), and toxic chemicals or proteins (e.g., 5-fluorouridine or ricin).

Since CD4$^+$ T cells are also involved in the pathogenic process of type 1 diabetes, and since CD4$^+$ T cells bind oligopeptides that are 13-25 amino acids, and only when presented on MHC class II molecules, mixtures of oligopeptides with MHC class II molecules are also within the scope of the invention. In these embodiments, the oligopeptides are 13-25 amino acids and comprise a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8). Analogous to previously described oligopeptide-MHC class I mixtures, the oligopeptides or MHC class II molecules of the oligopeptide-MHC class II mixtures can also usefully comprise a detectable label or a cytotoxic molecule.

It is also envisioned that any of the above-described oligopeptides or polypeptides are usefully provided in a sterile pharmaceutical preparation, particularly when the oligopeptide or polypeptide is to be utilized for therapeutic treatments. Thus, in some embodiments, the oligopeptide or polypeptide in a sterile pharmaceutical preparation is capable of tolerizing a mammal to reduce CD8$^+$ T cells reactive to IGRP. Also included as useful in a sterile pharmaceutical preparation is a mammalian IGRP protein itself, i.e., having at least 90% homology to SEQ ID NO:1 or SEQ ID NO:2. Preferably, this mammalian IGRP is a mouse IGRP or a human IGRP.

As indicated in Examples 2 and 3, it appears that a general characteristic of IGRP itself makes it unusually capable of contributing peptides that are ligands for T cells involved in type 1 diabetes.

Thus, the invention is also directed to isolated and purified oligopeptides 8-10 amino acids in length and completely homologous with a mammalian IGRP (e.g., mouse and human), where the oligopeptide is capable of binding a MHC class I molecule of the mammal. Preferably, the oligopeptide has at least 90% homology to SEQ ID NO:1 or SEQ ID NO:2. In preferred embodiments, the isolated and purified oligopeptide comprises a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8). In some preferred embodiments, particularly where the peptide is to be used diagnostically, the oligopeptide further comprises a detectable label as previously described, e.g., a fluorescent molecule, a radioactive molecule, or an enzyme. In other preferred embodiments, the peptide further comprises an MHC class I molecule that is capable of binding the oligopeptide. These oligopeptides, either with or without the detectable label, can also comprise an MHC class I molecule that is capable of binding the oligopeptide. As with previously discussed embodiments, the oligopeptide-MHC class I mixture can also comprise cytotoxic molecule, conjugated to the oligopeptide or to the MHC class I molecule.

Despite efforts to identify a function for IGRP, none has been found. It is therefore likely that therapy to reduce or eliminate expression of IGRP on islet cells would be beneficial in reducing or eliminating pathogenic islet cell destruction in type 1 diabetes, since such a therapy would eliminate the target ligand for the autoimmune reactions leading to type 1 diabetes. The reduction or elimination of IGRP expression can be achieved by treatment with antisense molecules, ribozymes, or RNAi molecules that target IGRP mRNA. In these embodiments, the antisense molecule, ribozyme, or RNAi molecules an be comprised of nucleic acid (e.g., DNA or RNA) or nucleic acid mimetics (e.g., phosphorothionate mimetics) as are known in the art.

Thus, the present invention is additionally directed to antisense molecules complementary to at least a portion of an mRNA encoding a mammalian (e.g., mouse and human) IGRP. In these embodiments, the antisense molecule is capable of inhibiting translation of a mammalian IGRP. Preferably, the mammalian IGRP is at least 90% homologous to SEQ ID NO:1 or SEQ ID NO:2. The antisense molecule for any mammalian IGRP can be designed without undue experimentation using known IGRP sequence information, e.g., as provided in GenBank accessions NM 021331 (mouse) and NM 021176 (human).

In related embodiments, the invention is directed to ribozymes that specifically cleave an mRNA encoding a mammalian (e.g., mouse or human) IGRP, thus inhibiting translation of the mammalian IGRP. Preferably, the mammalian IGRP is at least 90% homologous to SEQ ID NO:1 or SEQ ID NO:2. Since ribozyme technology is well established, the skilled artisan could design a ribozyme as described above without undue experimentation.

In additional related embodiments, the invention is directed to RNAi molecules that are homologous to a portion of an mRNA encoding a mammalian IGRP, and that are capable of inhibiting translation of a mammalian (e.g., mouse or human) IGRP. As is well known, an RNAi (including siRNA) molecule is a short double stranded nucleic acid that interferes with transcription or translation of a homologous gene. As with previous embodiments, the mammalian IGRP is at least 90% homologous SEQ ID NO:1 or SEQ ID NO:2. Since RNAi technology is well established, the skilled artisan could design an RNAi molecule as described above without undue experimentation.

Many of the above-described compositions are useful in methods of treating mammals (including but not limited to humans and rodents such as mice) that are at risk for, or have type 1 diabetes. As such, the above-described compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

Accordingly, in some embodiments, the invention is directed to methods of treating a mammal, where the mammal is at risk for or has type 1 diabetes. The methods comprise administering an oligopeptide in a sterile pharmaceutical preparation to the mammal in a manner sufficient to reduce T cells reactive to IGRP. In these embodiments, the oligopeptide comprises a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21). The last sequence is the sequence of the peptide NRP-I4, which is a peptide known to react to 8.3-like T cells, and which is shown in Example 3 to be an effective treatment for type 1 diabetes. The T cells reduced by these methods can be CD4$^+$, or preferably, CD8$^+$. In these methods, the oligopeptide or polypeptide treatment tolerizes the mammal to eliminate the T cells. Where the T cells are CD8$^+$, these methods would reduce or eliminate T cells reactive to IGRP in β-cells. See Examples 2-4. The oligopeptides or polypeptides of these embodiments are described above. They can be any size considered appropriate by the skilled artisan as appropriate for tolerization protocols, including 8-10mers, 13-25mers, or less than 25, or less than 50, or less than 100, or less than 300, or even larger, including an entire IGRP protein, or several of the peptides conjugated to an inert or immunogenic carrier. Protocols for tolerizing a mammal to T cell reactivity are well known. See, e.g., Gammon et al., 1986.

These methods include embodiments where more than one of the above-identified oligopeptides is used in the treatment, in order to eliminate other reactive CD8$^+$ T cells.

In other embodiments, the invention is directed to additional methods of treating a mammal, where the mammal is at risk for or has type I diabetes. These methods comprise administering, to the mammal, an oligopeptide of 8-10 amino acids comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), SFCKSASIP (SEQ ID NO:8), and YNIANWFL (SEQ ID NO:21). In these methods, a class I MHC molecule capable of binding the oligopeptide is also included with the oligopeptide, in such a manner as to cause oligopeptide-MHC binding. The oligopeptide and/or the class I MHC molecule in these embodiments further comprises a cytotoxic molecule, as described above. The oligopeptide-cytotoxic molecule is administered to the mammal in a manner sufficient to reduce CD8$^+$ T cells reactive to IGRP. The reduction in CD8$^+$ T cells is achieved when the peptide-MHC molecule-cytotoxic molecule binds to the 8.3-like T cell, which is killed by the cytotoxic molecule. As with the embodiments described above, more than one oligopeptide can be administered.

In these embodiments, the MHC class I molecules are preferably employed in the form of tetramers. See, e.g., Altman et al., 1996; Trudeau et al., 2003. However, the MHC class I molecule can also be present as part of an antigen-presenting cell. Such compositions are particularly useful for measuring cytokine (particularly interferon-γ) production from CD8$^+$ T cells. See, e.g., Example 2 and Terajima et al., 2003.

In related embodiments, the invention is directed to additional methods of treating a mammal, where the mammal is at risk for or has type 1 diabetes. These methods comprise administering to the mammal an oligopeptide 8-10 amino acids in length that is completely homologous with a mammalian IGRP, and is capable of binding a mammalian MHC class I molecule, as described above. The oligopeptide is preferably completely homologous with a mammalian IGRP having at least 90% homology to SEQ ID NO:1 or SEQ ID NO:2. In these methods, a class I MHC molecule capable of binding the oligopeptide is also included with the oligopeptide, in such a manner as to cause oligopeptide-MHC binding. In these embodiments, the oligopeptide and/or the class I MHC molecule further comprise a cytotoxic molecule, as described above. The oligopeptide-cytotoxic molecule is administered to the mammal in a manner sufficient to reduce CD8$^+$ T cells reactive to IGRP. The reduction in CD8$^+$ T cells is achieved when the peptide-MHC molecule-cytotoxic molecule binds to the IGRP-reactive T cell, which is then killed by the cytotoxic molecule. More than one oligopeptide can be administered in these embodiments.

As shown in Example 3, a particularly effective type 1 diabetes treatment is with an oligopeptide that has medium- or low-affinity binding to an IGRP$_{206-214}$-reactive CD8$^+$ T cell. Thus, the invention is also directed to additional methods of treating a mammal, wherein the mammal is at risk for or has type 1 diabetes. The methods comprising administering an oligopeptide 8-10 amino acids in length to the mammal, wherein the oligopeptide is a medium- or low-affinity ligand to an IGRP$_{206-214}$-reactive CD8+ T cell. Preferred examples of useful oligopeptides for these methods are KYNIANWFL (SEQ ID NO:65) and KYNKANAFL (SEQ ID NO:12), as utilized in Example 3.

In further embodiments, the invention is directed to methods of preventing a CD8$^+$ T cell that is cytotoxic to pancreatic islet β-cells from destroying a β-cell. These methods comprise treating the β-cell with a compound capable of binding an oligopeptide, where the oligopeptide is 8-10 amino acids in length and is completely homologous with a mammalian IGRP, as described above. By binding domains on β-cell IGRP, reaction of CD8$^+$ T cells with IGRP, which can lead to the destruction of the β-cell, can be prevented. The oligopeptide is preferably completely homologous with a mammalian IGRP having at least 90% homology to SEQ ID NO:1 or SEQ ID NO:2. In these embodiments, the oligopeptide-binding compound prevents binding of the oligopeptide to the MHC, or prevents binding of the oligopeptide-MHC complex to a $CD8^+$ T cell.

In preferred embodiments, the compound can bind an oligopeptide or polypeptide comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8).

In these embodiments, the compound capable of binding the oligopeptide can be any compound capable of interfering with the $CD8^+$ binding to the p cell, either by reducing the numbers of oligopeptide-MHC binding, or by causing a physical interference to the T cell binding to the oligopeptide-MHC complex. In preferred embodiments, the compound is an antibody or an aptamer.

Methods of making antibodies to an oligopeptide are routine, and the skilled artisan would expect that such an antibody could be made to any IGRP oligopeptide without undue experimentation. The antibodies can be from a polyclonal, monoclonal, or recombinant source. As used herein, "antibodies" also include a fragment of a whole antibody that comprises a typical immunoglobulin antigen binding site (e.g., Fab or Fab2). The antibodies can also be of any vertebrate (e.g., mouse, chicken, rabbit, goat or human), or of a mixture of vertebrates (e.g., humanized mouse).

Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. See, e.g., Burke et al., 1996; Ellington and Szostak 1990; Hirao et al., 1998; Jaeger et al., 1998; Kensch et al., 2000; Schneider et al., 1995; and U.S. Pat. Nos. 5,773,598; 5,496,938; 5,580,737; 5,654,151; 5,726,017; 5,786,462; 5,503,978; 6,028,186; 6,110,900; 6,124,449; 6,127,119; 6,140,490; 6,147,204; 6,168,778; and 6,171,795.

Aptamers that bind to virtually any particular target can be selected by using an iterative process called SELEX, which stands for Systematic Evolution of Ligands by EXponential enrichment (Burke et al., 1996; Ellington and Szostak, 1990; Schneider et al., 1995; Tuerk and Gold, 1992; Tuerk and Gold, 1990). Several variations of SELEX have been developed which improve the process and allow its use under particular circumstances. See, e.g., U.S. Pat. Nos. 5,472,841; 5,503,978; 5,567,588; 5,582,981; 5,637,459; 5,683,867; 5,705,337; 5,712,375; and 6,083,696. Thus, the production of aptamers to any particular oligopeptide, including IGRP oligopeptides, requires no undue experimentation.

Additionally, the pancreatic islet β-cell in these methods can be treated ex vivo or in vitro (e.g., on islet β cells that are for transplanting into a patient having type 1 diabetes). In preferred embodiments, the islet β-cell is part of a pancreas of a mammal at risk for or having type 1 diabetes. While the methods are not limited to the use with any particular mammal, a mouse or a human is preferred.

The present invention is also directed to methods of preventing a $CD8^+$ T cell that is cytotoxic to pancreatic islet β-cells from destroying a β-cell. The methods comprise treating the $CD8^+$ T cell with an oligopeptide of 8-10 amino acids comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(LN)(F/L)(G/N)IDLL (SEQ ID NO:6), KWCANPDWI (SEQ ID NO:7), and SFCKSASIP (SEQ ID NO:8), as described above, along with an MHC class I molecule that is capable of binding the oligopeptide, as described above. The MHC class I molecules in these embodiments is preferably in the form of a tetramer, as described above. In these embodiments, the $CD8^+$ T cell binds the oligopeptide-MHC combination, preventing the T cell from binding to the oligopeptide-MHC on the β-cell.

In some embodiments of these methods, the oligopeptide or MHC molecule further comprises a cytotoxic molecule, as described above, such that the T cell is killed when it binds to the oligopeptide-MHC-cytotoxic molecule combination.

The pancreatic islet β-cell in these methods can also be treated ex vivo or in vitro (e.g., on islet β cells that are for transplanting into a patient having type 1 diabetes). In preferred embodiments, the islet β-cell is part of a pancreas of a mammal at risk for or having type 1 diabetes. While the methods are not limited to the use with any particular mammal, a mouse or a human is preferred.

In related embodiments, the invention is directed to other methods of preventing a $CD8^+$ T cell that is cytotoxic to pancreatic islet β-cells from destroying a β-cell. The methods comprise treating the $CD8^+$ T cell with an oligopeptide of 8-10 amino acids completely homologous with a mammalian IGRP, as described above, along with an MHC class I molecule that is capable of binding the oligopeptide, as described above. The oligopeptide or these embodiments is capable of binding a human MHC class I molecule. Preferably, the oligopeptide has at least 90% homology to SEQ ID NO:1 or SEQ ID NO:2.

The MHC class I molecules in these embodiments is preferably in the form of a tetramer, as described above. In these embodiments, the $CD8^+$ T cell binds the oligopeptide-MHC combination, preventing the T cell from binding to the oligopeptide-MHC on the β-cell.

In some embodiments of these methods, the oligopeptide or MHC molecule further comprises a cytotoxic molecule, as described above, such that the T cell is killed when it binds to the oligopeptide-MHC-cytotoxic molecule combination.

The pancreatic islet β-cell in these methods can also be treated ex vivo or in vitro (e.g., on islet β cells that are for transplanting into a patient having type 1 diabetes). In preferred embodiments, the islet β-cell is part of a pancreas of a mammal at risk for or having type 1 diabetes. While the methods are not limited to the use with any particular mammal, a mouse or a human is preferred.

Additionally, the present invention is directed to methods of treating a mammal at risk for type I diabetes. The methods of these embodiments comprise administering to the mammal a compound capable of specifically decreasing expression of IGRP in the mammal. In these embodiments, the compound is selected from the group consisting of the antisense molecule, the ribozyme, and the RNAi molecule previously described, where the compound is administered in a manner sufficient to decrease expression of IGRP in the mammal. While the methods are not limited to the use with any particular mammal, a mouse or a human is preferred.

A known method of treatment of mammals (including humans) having type I diabetes is transplanting pancreatic islet β-cells into the pancreas of the mammal. However, since β-cell-autoreactive CD8+ T cells are generally present after transplant, the transplanted β-cells are often also destroyed. The present invention provides methods for reducing or eliminating this destruction of the transplanted β-cells. The methods involve transfecting the β-cells with a vector expressing a nucleic acid that reduces or eliminates expression of the IGRP in the cells. The transfected cells, which are expressing little or no IGRP, are then transplanted into the mammal. Since those cells express little or no IGRP, autoreactive CD8+ T cells are not able to bind to and destroy the β-cells.

Thus, in these embodiments, the invention is directed to additional methods of treating a mammal having type I diabetes. The methods comprise transplanting pancreatic islet β-cells into the pancreas of the mammal, where the β-cells are transfected with a vector that expresses a nucleic acid. The nucleic acid is selected from the group consisting of the antisense molecule described above, the ribozyme described above, and the RNAi molecule described above. In these embodiments, the nucleic acid is expressed in a manner sufficient to decrease expression of IGRP in the β-cells.

These embodiments are not limited to any particular type of vector. As is well known in the art, examples of suitable vectors include a naked DNA vector and a viral vector (e.g., adenoviral or lentiviral). The skilled artisan can select and synthesize an appropriate vector without undue experimentation.

As with other embodiments, the methods are not limited to use with any particular mammal. In preferred embodiments, the mammal is a mouse or a human.

The discovery of the role of IGRP in type I diabetes suggests several diagnostic methods. Accordingly, in some embodiments, the invention is directed to methods for determining whether a mammal is at risk for or has type 1 diabetes. The methods comprise determining the presence of CD8+ T cells reactive to IGRP in the mammal by
  a. obtaining a sample of lymphocytes comprising CD8+ T cells from the mammal by standard methods (e.g., venipuncture);
  b. combining the lymphocytes with an oligopeptide of 8-10 amino acids comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8), as described above, along with an MHC class I molecule that is capable of binding the oligopeptide, as described above, and where the oligopeptide or the MHC class I molecule further comprises a detectable label, as described above; and
  c. determining whether any CD8+ T cells specifically bind to the oligopeptide. In these methods, CD8+ T cell binding to the oligopeptide indicates that the mammal is at risk for or has type I diabetes.

These methods can be used with any mammal, although the mammal is preferably a mouse or a human.

The determination step (c.) can be by any known means. In some preferred embodiments, the determination step is performed by counting labeled CD8+ T cells using a cell sorter (e.g., a fluorescence activated cell sorter) or labeled cell counter (e.g., Coulter counter). In other preferred embodiments, the determination step is performed by microscopic observation of the lymphocytes under conditions where the label can be observed, e.g., with a fluorescence microscope if a fluorescent label is used, or light microscope if an enzyme label and colored enzyme substrate is used to visualize the bound T cells. In additional preferred embodiments, the determination step is performed by measuring activation of the CD8+ T cells, preferably by measuring interferon-γ production by known methods, for example using an ELISpot assay (see, e.g., Hartemann et al., 1999).

The invention is also directed to other methods for determining whether a mammal is at risk for or has type 1 diabetes. The methods comprise determining the presence of CD8+ T cells reactive to IGRP in the mammal by
  a. obtaining a sample of lymphocytes comprising CD8+ T cells from the mammal by standard methods (e.g., venipuncture);
  b. combining the lymphocytes with an oligopeptide 8-10 amino acids in length that is completely homologous with a mammalian IGRP, where the oligopeptide is capable of binding a human MHC class I molecule, as described above, along with and an MHC class I molecule that is capable of binding the oligopeptide, as described above, and where the oligopeptide or the MHC class I molecule further comprises a detectable label, as described above; and
  c. determining whether any CD8+ T cells specifically bind to the oligopeptide. In these methods, CD8+ T cell binding to the oligopeptide indicates that the mammal is at risk for or has type 1 diabetes.

In preferred embodiments, the oligopeptide used in these methods has at least 90% homology to SEQ ID NO: 1 or SEQ ID NO:2. As with the other diagnostic method described above, the determination step is preferably performed by counting labeled CD8+ T cells using a cell sorter or labeled cell counter, or by microscopic observation of the lymphocytes under conditions where the label can be observed, or by measuring activation of the CD8+ T cells, e.g., by measuring interferon-γ production, for example using an ELISpot assay.

All of the above treatment or diagnostic methods suggest second medical use embodiments (e.g., the use of an oligopeptide or polypeptide comprising a sequence selected from the group consisting of YLKTN(A/I/L/V)FL (SEQ ID NO:3), FLWSVFWLI (SEQ ID NO:4), (T/A)YY(G/T)FLNFM (SEQ ID NO:5), LR(L/V)(F/L)(G/N)IDLL (SEQ ID NO:6), KWCANPDWI (SEQ ID NO:7), and SFCKSASIP (SEQ ID NO:8), in a sterile pharmaceutical preparation, for the manufacture of a medicament for treating a mammal, where the mammal is at risk for or has type 1 diabetes, by administering the oligopeptide or polypeptide to the mammal in a manner sufficient to reduce T cells reactive to IGRP); all such second medical use embodiments suggested by the above claims are specifically envisioned herein.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Identity of the Antigen Targeted by Prevalent Pathogenic T Cells in Diabetes

Example Summary

CD8+ T cells are essential for destruction of the insulin-producing pancreatic n-cells in autoimmune (type 1) diabetes. Yet their antigenic targets are largely unknown. Here we reveal that the 13 cell target of a prevalent population of pathogenic CD8+ T cells in NOD mice is islet-specific glucose-6-phosphatase catalytic subunit-related protein (IGRP). The human IGRP gene maps to a diabetes susceptibility locus, indicating that IGRP is also an antigen for pathogenic T cells in human type 1 diabetes and, thus, a new target for diagnostic and therapeutic approaches.

Materials and Methods

Mice.

NOD/Lt mice were maintained by brother-sister mating. 8.3-TCRαβ-transgenic NOD mice, designated 8.3-NOD, have been described (Verdaguer et al., 1997). All mice were maintained under specific pathogen-free conditions and used in accordance with institutional guidelines for animal welfare.

Class I MHC-Associated Peptides.

H-2K$^d$ molecules were immunoaffinity purified from 1.4× 10$^{10}$ interferon-γ-treated NIT-1 pancreatic β cells (Hamaguchi et al., 1991) using monoclonal antibody SF1-1.1, and their associated peptides extracted as previously described (Cox et al., 1997). Peptide extracts were fractionated by two rounds of reverse phase HPLC as described (Pierce et al., 1999).

Epitope Reconstitution Assays.

8.3 CTL were generated by culturing splenocytes from 8.3-NOD mice with mitomycin C-treated NOD splenocytes pulsed with NRP-A7 peptide as described (DiLorenzo et al, 2002). CTL were used in 16 h $^{51}$Cr-release cytotoxicity assays to test for recognition of peptide-pulsed RMA-S/K$^d$ target cells (provided by M. Bevan, University of Washington, Seattle, Wash., USA) at an effector to target ratio of 40:1 as described (DiLorenzo et al., 2002). Synthetic peptides were used at concentrations as indicated in the figures, and 7×10$^8$, 6×10$^8$, and 2×10$^9$ NIT-1-cell-equivalents of peptide were used for assays of first-, second-, and third-dimension HPLC fractions, respectively.

Peptide Analysis.

Active second-dimension fraction 66 was loaded on a reverse-phase microcapillary column and analyzed by micro-ESI on a home-assembled FT-ICR MS, equipped with nanoflow liquid chromatography and an online effluent splitter (Cox et al., 1997; Pierce et al., 1999). Briefly, effluent from the microcapillary HPLC column was split such that one-nineteenth was directed into the FT-ICR MS for ESI MS analysis and the remaining eighteen-nineteenths were deposited directly into the wells of a 96-well plate for epitope reconstitution assays. In this way, each well could be correlated to a set of scans in the mass spectral data. Peptide masses eluting in the area of CTL activity and having an elution profile similar to the activity lysis profile were marked as antigen candidates. Good candidates had a deconvoluted (M+H)+ mass between 800 and 1600 Da, the mass range characteristic of peptides eluted from class I MHC molecules.

Sequence Analysis and Synthesis of Candidate Antigens.

CAD mass spectra were recorded for selected peptide candidates using a ThermoFinnigan ion trap mass spectrometer (LCQ). Candidate masses were targeted throughout the chromatographic run. Candidate peptides (VYLKTNVFL (SEQ ID NO:19) and IYQKAFDLI (SEQ ID NO:20)) were synthesized by standard Fmoc chemistry using a Gilson peptide synthesizer (model AMS422) and purified to >95% by reverse phase HPLC. Candidate antigen sequences were confirmed by comparing CAD spectra to those of synthetic peptides. Further sequence confirmation and an estimation of copy number per cell was determined by running an aliquot of the active fraction and comparing antigen ion abundance to an identical run with synthetic antigen spiked in at a known level. Synthetic and naturally processed peptide co-elution further confirmed the identity of the antigen.

Synthetic Peptides.

NRP-A7 (KYNKANAFL) (SEQ ID NO:12), NRP-V7 (KYNKANVFL) (SEQ ID NO:11), INS B$_{15-23}$ (LYLVCGERG) (SEQ ID NO:13), INS-19 (LYLVCGERI) (SEQ ID NO:14), TUM (KYQAVTTTL) (SEQ ID NO:15), and G6Pase (KYCLITIFL) (SEQ ID NO:16) peptides were synthesized by standard solid-phase methods using Fmoc chemistry in an automated peptide synthesizer (Applied Biosystems model 433A), and their identities were confirmed by mass spectrometry.

Transient Transfection.

COS-7 cells were transfected using a DEAE-dextran protocol as described (Karttunen et al., 1992). 10 ng/ml of DNA for the class I MHC molecule (H-2K$^d$ or H-2D$^b$) expression constructs was used along with concentrations of IGRP expression construct or vector alone as indicated in the figure. Separate cultures were transfected with the H-2K$^d$ construct alone and pulsed with varying concentrations of IGRP$_{206-214}$ peptide. Following co-culture with 8.3 CTL, T cell response was measured as IFN-γ release by ELISA.

T Cell Receptor Transfectants.

T cell receptors from the previously isolated NOD-derived β cell-autoreactive class I MHC-restricted T cell clones AI4, AI12.B1.1, AI12.B1.2, AI12.B1.3, AI15.A10, AI15.F5 (DiLorenzo et al., 1998), and 8.3 (Verdaguer et al., 1997) were expressed in the TCR− T cell hybridoma 58α−β− (engineered to express the TCR ζ chain and CD8αβ and provided by H.-C. Chang, Dana Farber, Boston, Mass., USA) as described (Serreze et al., 2001). TCR expression was verified by flow cytometric analysis of growing clones using an antibody to CD3ε (145-2C11). RMA-S/K$^d$ cells incubated overnight at 28° C. were used to present exogenously added synthetic peptides at concentrations as indicated in the figures. Peptide recognition by the TCR transfectants was measured by IL-2 production as previously described (Serreze et al., 2001).

H-2K$^d$ Stabilization Assay.

RMA-S/K$^d$ cells, cultured overnight at 28° C., were pulsed with peptides in complete DMEM for 1 h at 28° C., incubated at 37° C. for 3 h, washed, stained with anti-H-2K$^d$ monoclonal antibody SF1-1.1, counter-stained with FITC-conjugated polyclonal goat anti-mouse antibody, and analyzed by flow cytometry. Data were calculated by subtracting mean fluorescence intensity of H-2K$^d$ on non-peptide-pulsed cells from that on peptide-pulsed cells.

Tetramer Staining and Flow Cytometry.

Islet-associated and peripheral blood-derived CD8+ T cells were isolated from NOD mice as previously described (Amrani et al., 2000; Trudeau et al., 2003). Tetramers were prepared and used as previously described (Amrani et al., 2000).

Results and Discussion

To identify the pancreatic β cell antigen naturally recognized by the diabetogenic 8.3-like CD8+ T cell population, we purified H-2K$^d$ class I MHC molecules from the NOD-derived pancreatic β cell line NIT-1 by immunoaffinity chromatography. Peptides were eluted from the H-2K$^d$ molecules and fractionated by reverse phase high-performance liquid chromatography (HPLC). Fractions were tested for their ability to elicit 8.3 cytotoxic T lymphocyte (CTL)-mediated lysis of peptide-pulsed target cells (FIG. 1A). Fractions composing the active peak were pooled and subjected to another round of HPLC under different conditions. A single peak of activity was observed (FIG. 1B). Second-dimension fraction 66 was rechromatographed and a portion of the effluent was analyzed by electrospray ionization (ESI) on a Fourier transform ion cyclotron resonance mass spectrometer (FT-ICR MS) equipped with nanoflow liquid chromatography and an online effluent splitter. For this splitter experiment, a portion of the effluent was deposited in 96-well plates for determination of epitope reconstitution activity, and the remainder was directed to the mass spectrometer. Testing of peptide fractions for recognition by 8.3 CTL yielded a single peak of activity (FIG. 1C). Candidate peptides were identified by comparing the abundances of ions observed in the active and adjoining fractions with the lysis profile from the epitope reconstitution assay (FIG. 1D). Over 100 peptide candidates were present in the scan window; of these, approximately 35 eluted entirely within the window. Candidates were ranked based on the extent of alignment between their ion abundance curves and the lysis profile. Only the abundance curves for the best candidates and one very abundant later-eluting peptide are shown in FIG. 1D. The millimass accuracy capability of the FT-ICR MS allowed co-eluting peptides differing by <0.1 mass unit to be easily distinguished, and the detection limit of the instrument (2-10 attomoles) made it possible to detect peptide candidates present at only a few copies per cell (Martin et al., 2000).

Based on alignment between abundance curves and the lysis profile, the best peptide candidate, while not the most abundant, was the one having a doubly charged monoisotopic m/z of 548.845 (FIG. 1D). Sequence analysis yielded VYXKTNVFX (SEQ ID NO:17) (FIG. 1E), where X represents either I or L, amino acids of identical mass which cannot be differentiated by the instrument. Similarly, the sequence of the abundant later-eluting peptide (m/z of 555.835$^{+2}$) was determined to be XYQKAFDXX (SEQ ID NO:18) (S. M. Lieberman et al., data not shown). Protein database searches yielded one perfect match each for VYXKTNVFX (SEQ ID NO:17) and XYQKAFDXX (SEQ ID NO:18) (VYLKTNVFL (SEQ ID NO:19) and IYQKAFDLI (SEQ ID NO:20), respectively). These peptides were synthesized and tested in epitope reconstitution assays. FIG. 1F reveals that VYLKTNVFL (SEQ ID NO:19) is the natural β cell peptide recognized by 8.3 and that activated 8.3 CTL respond to it in an equivalent dose-dependent manner as to the previously described synthetic agonist NRP-A7 and superagonist NRP-V7 (Anderson et al., 1999; Amrani et al., 2001), with half-maximal activity observed at a peptide concentration of ~50 μM. Approximately 100 copies of VYLKTNVFL(SEQ ID NO:19)/H-2K$^d$ are present per interferon (IFN)-γ-treated NIT-1 cell.

A BLAST search of the entire NCBI non-redundant protein database resulted in only one exact hit for VYLKTNVFL (SEQ ID NO:19) corresponding to residues 206-214 of murine islet-specific glucose-6-phosphatase catalytic subunit-related protein (IGRP) (Arden et al., 1999). To confirm that the source of the antigenic peptide was indeed IGRP, we transfected COS-7 cells with varying concentrations of an expression construct for IGRP, or vector alone, together with an H-2K$^d$ expression construct and tested for recognition by 8.3 CTL. Cells transfected with IGRP, but not vector alone, stimulated 8.3 CTL to release IFN-γ in a dose-dependent manner upon co-culture (FIG. 1G). This response required the expression of H-2K$^d$; transfection of the IGRP construct along with an H-2D$^b$ expression construct resulted in a T cell response profile similar to that of vector alone (S. M. Lieberman et al., data not shown). To our knowledge, IGRP has not previously been implicated as either a T cell or B cell antigen in NOD mice or in type 1 diabetes patients. Thus, IGRP is the natural target of the prevalent and pathogenic 8.3-like T cell population in NOD mice and represents a new β cell autoantigen.

Figure 2:
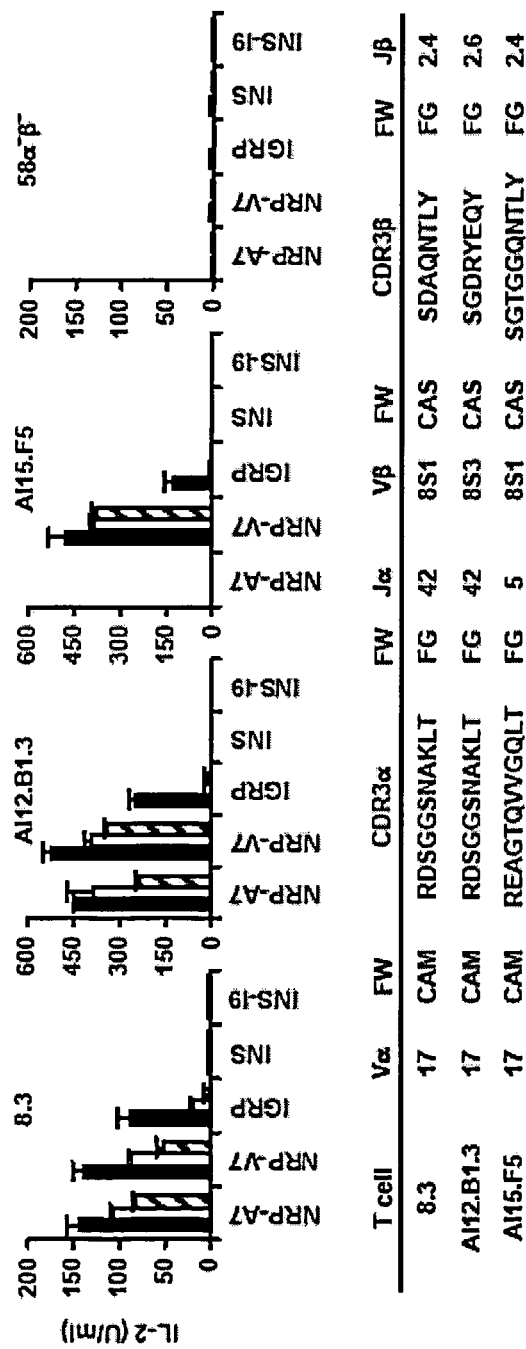
FIG. 2 is graphs of experimental results establishing that multiple early insulitic T cell clones recognize $IGRP_{206-214}$. 58 $α^−β^−$ transfectants expressing the indicated TCRs were cultured with RMA-S/$K^d$ cells pulsed with the indicated peptides and IL-2 release (mean±SD) was measured by ELISA. The partial TCR α and β chain sequences for 8.3 and for the early insulitic T cell clones AI12.B1.3 and AI15.F5 were previously reported (DiLorenzo et al., 1998; Santamaria et al., 1995, Nagata et al., 1994. The AI4, AI12.B1.1, AI12.B1.2, and AI15.A10 lines, all of which express non-Vα17 TCR α chains, did not respond to any of the peptides tested, although they were capable of signaling through the transfected TCR as evidenced by their release of IL-2 in response to plate-bound anti-CD3ε (S. M. Lieberman et al., data not shown). IGRP, $IGRP_{206-214}$; INS, INS $B_{15-23}$; FW, framework residues; CDR, complementarity-determining region. Peptide sequences in figure: RDSGGSNAKLT (SEQ ID NO:95), REAGTQVVGQLT (SEQ ID NO:96), SDAQNTLY (SEQ ID NO:97), SGDRYEQY (SEQ ID NO:98), and SGTGGQNTLY (SEQ ID NO:99).

We previously isolated a set of six β cell-autoreactive CD8+ T cell clones of unknown antigenic specificity from early insulitic lesions of young NOD mice (designated AI4, AI12.B1.1, AI12.B1.2, AI12.B1.3, AI15.A10, and AI15.F5) (DiLorenzo et al., 1998). We had earlier reported that AI12.B1.3, which expresses a Vα17-Jα42 TCR α chain nearly identical to that of 8.3, recognizes NRP-A7 (Serreze et al., 2001). Thus, we hypothesized it would also recognize IGRP$_{206-214}$. To test whether this and any other clones in our panel were IGRP$_{206-214}$-reactive, we assayed their ability to recognize IGRP$_{206-214}$. AI12.B1.3 recognized IGRP$_{206-214}$, as well as NRP-V7 and NRP-A7, but not the previously identified antigenic insulin peptide (INS B$_{15-23}$) or its 19 variant (INS-19) (Wong et al., 1999; Wong et al., 2002) (FIG. 2). Hence, the 8.3 clonotype is not unique; other β cell-autoreactive CD8+ T cells sharing the prevalent Vα17-Jα42 TCR α chain also recognize IGRP$_{206-214}$. Importantly, AI15.F5, which expresses a Vα17-Jα5 TCR α chain and a similar TCR β chain to 8.3, also responded to IGRP$_{206-214}$ and NRP-V7, although it did not recognize NRP-A7 (FIG. 2). This demonstrates that reactivity to IGRP$_{206-214}$ is not limited strictly to T cells expressing a Vα17-Jα42 TCR α chain. Further, the ability of AI15.F5 to recognize NRP-V7, but not NRP-A7, is consistent with the recent observation that NRP-V7/H-2K$^d$ tetramers stain a larger population of islet T cells than do NRP-A7 tetramers (Trudeau et al., 2003). Thus, previous measurements of NRP-A7 reactivity (Amrani et al., 2000) have underestimated the prevalence of the IGRP$_{206-214}$-reactive T cell population.

Figure 3:
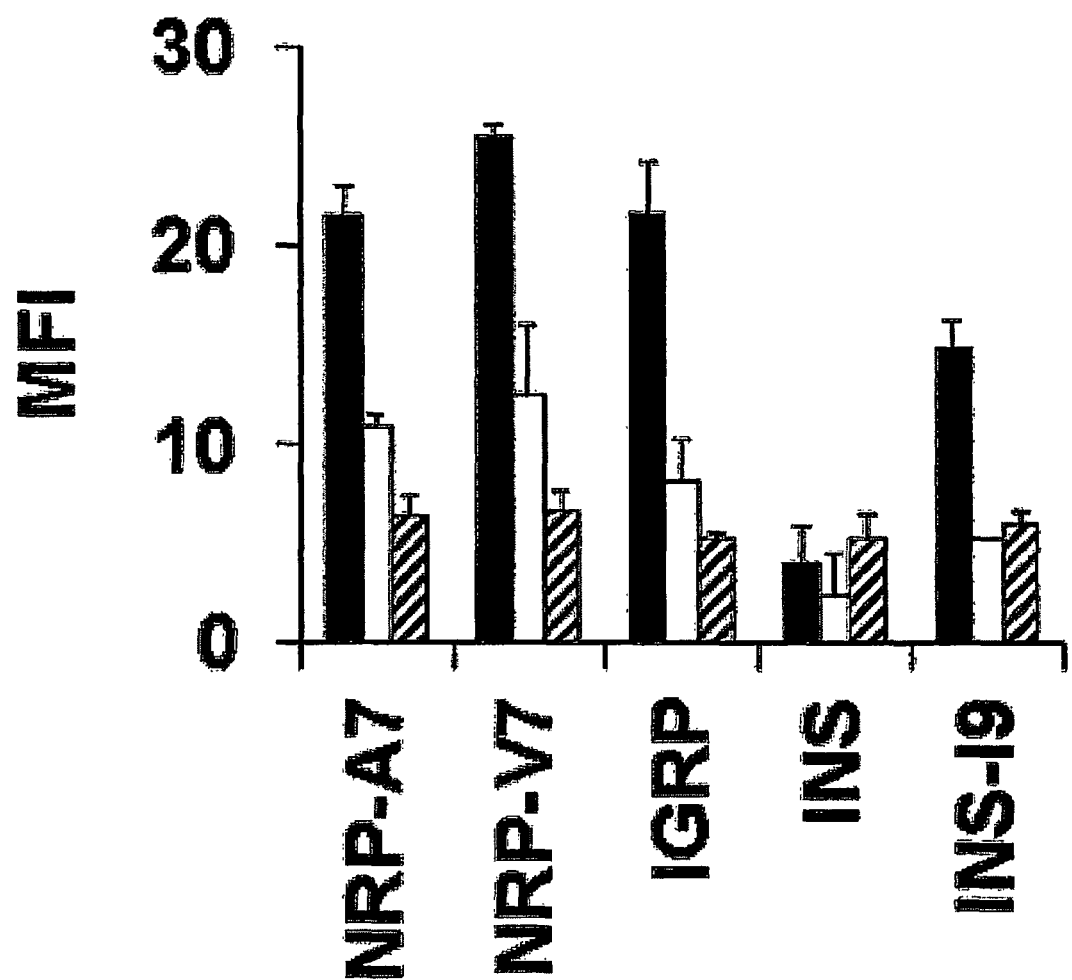
FIG. 3 is a graph of experimental results establishing that $IGRP_{206-214}$ does not demonstrate poor peptide binding to $H-2K^d$. RMA-S/$K^d$ cells were pulsed with the indicated peptides, stained with an anti-$H-2K^d$ antibody, and analyzed by flow cytometry. IGRP, $IGRP_{206-214}$; INS, INS $B_{15}$-23; MFI, mean fluorescence intensity.

The only other known natural ligand for an NOD-derived diabetogenic CD8+ T cell clone is INS B$_{15-23}$ presented by H-2K$^d$ (Wong et al., 1999). The insulin peptide exhibits very poor binding to H-2K$^d$, and it has been suggested that this results in insufficient peptide presentation for T cell negative selection in the thymus (Wong et al., 2002). To determine whether poor MHC binding is a characteristic of autoantigenic peptides in general, we tested the ability of IGRP$_{206-214}$ to bind H-2K$^d$. In H-2K$^d$ stabilization assays, IGRP$_{206-214}$ demonstrated good MEC binding, comparable to that of the synthetic ligands NRP-V7 and NRP-A7 and considerably better than that of INS B$_{15-23}$, which was barely detectable even at the highest peptide concentration tested (FIG. 3). Like NRP-V7 and NRP-A7, IGRP$_{206-214}$ contains the expected H-2K$^d$ anchor residues, i.e., Y at position 2 and L at 9, while INS B$_{15-23}$ has G at position 9, which makes its binding to H-2K$^d$ unfavorable. When G at position 9 is replaced with I, the resulting INS-I9 peptide shows improved binding to H-2K$^d$ (FIG. 3) (Wong et al., 2002). Furthermore, when the protein sequence of murine IGRP is analyzed by several different algorithms designed to identify good MHC-binding peptides (SYFPEITHI (Rammensee et al., 1999), BIMAS (Parker et al., 1994), or RANKPEP (Reche et al., 2002)), IGRP$_{206-214}$ consistently ranks among the best H-2K$^d$ binders (third, first, or second, respectively). Taken together, these observations indicate that poor MHC class I binding is not a requirement for self-peptides recognized by autoreactive CD8$^+$ T cells.

Figure 4:
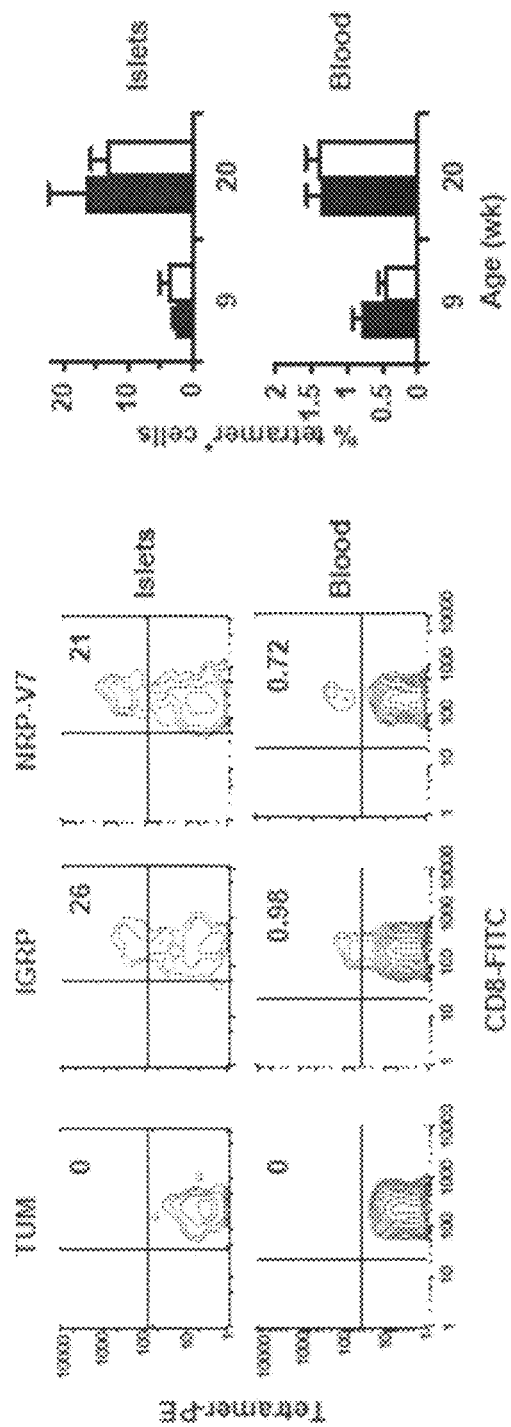
FIG. 4 is graphs of experimental results establishing that $IGRP_{206-214}$-reactive T cells are readily detected in islets and peripheral blood of NOD mice directly ex vivo. Cells from islets or peripheral blood of 9- or 20-week-old nondiabetic NOD mice were stained with anti-CD8 and the indicated peptide/$H-2K^d$ tetramers. The left panel shows representative tetramer staining patterns of samples from 20-week-old mice gated on the CD8+ population. Numbers indicate percentage of tetramer-positive cells within the CD8+ population. The right panel shows the percentage (mean±SD) of tetramer-positive cells within the CD8+ population for five individual mice per age group. TUM/$H-2K^d$ tetramers stained 0% of cells in each group. IGRP, $IGRP_{206-214}$.

A recent study demonstrated that NRP-V7/H-2K$^d$ tetramers could be used to detect and to quantify islet- and peripheral blood-derived NRP-V7-reactive CTL directly ex vivo (Trudeau et al., 2003). However, the use of natural self-peptides in tetramer studies to identify autoreactive T cells directly ex vivo has only been reported for melanocyte-antigen-specific T cells (Pettet et al., 2002). To evaluate whether the natural IGRP peptide, which differs from the 8.3 superagonist NRP-V7 (KYNKANVFL) (SEQ ID NO:11) by only three residues, could similarly be used to quantify the prevalent β cell-autoreactive T cell population, we isolated T cells from both islets and peripheral blood of 9- and 20-week-old nondiabetic NOD mice and stained them with IGRP$_{206-214}$, NRP-V7, or negative control peptide (TUM) tetramers. A sizeable proportion of islet T cells from 9- or 20-week-old mice was IGRP-reactive, and a population of IGRP-reactive cells was clearly measurable in peripheral blood (FIG. 4). Importantly, for both islet and peripheral blood samples of 9- or 20-week-old mice, the size of the CD8$^+$ T cell population that stained with tetramer was similar whether IGRP$_{206-214}$ or NRP-V7 tetramers were used for detection. Thus, the natural peptide can be used to detect and to quantify IGRP$_{206-214}$-reactive islet and peripheral blood T cells directly ex vivo.

The role of CD8$^+$ T cells in autoimmune diseases such as type 1 diabetes is becoming more widely recognized (Liblau et al., 2002); however, knowledge of the natural ligands of these pathogenic T cells in spontaneous autoimmune diseases is extremely limited. Here we have identified IGRP as the source of the natural peptide recognized by a prevalent population of pathogenic CD8$^+$ T cells in NOD mice. IGRP is an islet-specific protein expressed in pancreatic β cells, and to a lesser extent in α cells, and shares approximately 50% identity with the catalytic subunit of the liver enzyme glucose-6-phosphatase (G6Pase) (Martin et al., 2001). Importantly, IGRP$_{206-214}$ differs from the homologous residues of murine G6Pase (KYCLITIFL) (SEQ ID NO:16) at six of nine positions. Accordingly, this liver G6Pase peptide is not recognized by 8.3 CTL (S. M. Lieberman et al., data not shown). Despite its homology to G6Pase, no catalytic activity has been demonstrated for IGRP, and its function is unknown (Ardin et al., 1999; Martin et al., 2001). From its sequence, it is predicted to be an ER-resident protein that spans the membrane nine times (Arden et al., 1999). The abundance of its RNA places IGRP among β cell genes expressed at moderate to high levels (Id.), and the protein can be readily detected in islets by immunohistochemistry (Martin et al., 2001). Intriguingly, the human IGRP gene, which maps to chromosome 2q28-32 (26), overlaps a diabetes susceptibility locus, IDDM7 (2q31) (Pociot & McDermott, 2002), for which the responsible gene is unknown.

The IGRP-reactive T cell population constitutes a substantial component of even the earliest NOD islet infiltrates (FIG. 2) (DiLorenzo et al., 1998), and its pathogenicity has been clearly established (Amrani et al., 2000; Trudeau et al., 2003; Anderson et al., 1999; Nagata et al., 1994; Verdaguer et al., 1997). Thus, the response to IGRP appears to be one of the first events leading to β cell destruction by CD8$^+$ T cells in autoimmune diabetes. Now, with the identification of IGRP as the natural β cell antigen targeted by 8.3-like T cells, critical aspects of their development, activation, and expansion can be further investigated. Already this knowledge has made possible the elucidation of the mechanisms responsible for the avidity maturation of this pathogenic T cell population in NOD mice (Han et al, in preparation). In addition, it will now be possible to confirm that a similarly prevalent IGRP-reactive T cell population participates in the pathogenesis of human type 1 diabetes. As several β cell autoantigens in NOD mice overlap those that have been identified in patients (Tisch & McDevitt, 1996), and the human IGRP gene maps to a diabetes susceptibility locus, it is likely that IGRP will demonstrate considerable importance in the development of the human disease.

Example 2

Protection of NOD Mice from Type 1 Diabetes Using IGRP$_{206-214}$

Ten NOD female mice were treated with 100 micrograms of IGRP$_{206-214}$ peptide (in phosphate-buffered saline) intraperitoneally, starting at 3.5 weeks of age. Forty mice were used as controls. Each control mouse was treated with the TUM peptide (KYQAVTTTL) (SEQ ID NO:15). The mice received one injection of peptide every two weeks for the first three injections, and then one injection every three weeks thereafter. At ~25 weeks-old, two (20%) of the IGRP$_{206-214}$ mice developed diabetes, vs. 26 control mice (~65%). The two mice that have developed diabetes did not have IGRP$_{206-214}$-reactive T-cells in islets, as determined by T-cell staining with NRP-V7/K$^d$ tetramers. This was also confirmed by determining whether islet-derived T-cells from these mice produced interferon-γ upon stimulation with IGRP$_{206-214}$ and NRP-V7 in vitro. There were no significant differences in interferon-γ production vs. cells stimulated with the negative control peptide TUM. In one of these two mice, the islets contained T-cells that responded to two IGRP peptides other than IGRP$_{206-214}$. These results indicate that tolerization to IGRP$_{206-214}$ protects against the development of type 1 diabetes, and that other IGRP peptides can contribute to the development of type 1 diabetes.

Further supporting the assertion that other IGRP peptides can contribute to the development of type 1 diabetes, the inventors have also discovered that the peptide CALTSLTTM (SEQ ID NO:81), present in mouse IGRP at amino acid residues 296-304, is presented by the MHC class I molecule H-2Db.

Example 3

Prevention of Diabetes by Manipulation of Anti-IGRP Autoimmunity: High Efficiency of a Low Affinity Altered Peptide Ligand Example Summary Antigen therapy holds great promise for the prevention of organ-specific autoimmunity. However, limited clinical trials in humans have almost invariably met with failure, possibly because the principles guiding the choice of treatment remain poorly defined. Here, we have examined the antidiabetogenic properties of wild type or altered peptide ligands of CD8+ T-cells recognizing an epitope from islet-specific glucose 6 phosphatase catalytic subunit-related protein (IGRP$_{206-214}$), a prevalent population of autoreactive T-cells in murine autoimmune diabetes. We show that pancreatic islet-associated CD8+ T-cells in nonobese diabetic mice recognize several additional epitopes of IGRP, and that these cells play a role in the outcome of peptide-treatment protocols designed to induce IGRP$_{206-214}$-specific tolerance. Altered peptide ligands targeting IGRP$_{206-214}$-reactive CD8+ T-cells could effectively curb the progression of diabetes, but only at doses that spared low avidity IGRP$_{206-214}$-specific clonotypes. In contrast, near complete depletion of the IGRP$_{206-214}$-reactive T-cell pool by relatively high doses of these ligands resulted in enhanced recruitment of sub-dominant IGRP epitope-reactive T-cell specificities and did not significantly inhibit diabetes progression. These results suggest that peptide therapy in organ-specific autoimmunity is most effective under conditions that foster the occupation of the target organ lymphocyte niche by non-pathogenic, low avidity clonotypes.

Introduction

Administration of autoantigenic proteins or peptides in solution can blunt the initiation and/or progression of autoimmunity in experimental models of autoimmune disease (Wraith et al, 1989; Metzler and Wraith, 1993; Liu and Wraith, 1995; Anderton and Wraith, 1998; Karin et al., 1994). However, limited clinical trials in humans employing similar strategies have almost invariably met with failure (Weiner, 1993; Trentham, et al., 1993; McKown et al., 1999; Pozzalli et al., 2000; Group, D.P.T.-T.D.S., 2002; Kappos et al., 2000; Bielekova et al., 2000). This suggests that the principles guiding the choice and conditions of treatment are poorly defined and, as a result, inadequate for human application.

Unlike their experimental counterparts, spontaneous organ-specific autoimmune disorders result from complex responses against numerous epitopes in multiple antigens that arise spontaneously in a stochastic and often unpredictable sequence. This complexity is compounded by the fact that lymphocyte clones recognizing identical epitopes engage antigen/MHC within a broad range of avidities, the strength of which correlates with pathogenic potential (Amrani et al., 2000; Santamaria, 2001; Liblau et al., 2002). Consequently, the outcome of any immunization strategy for the prevention of autoimmunity is likely to be influenced by the choice of autoantigen(s), dose, periodicity of treatment, and route and form of administration. Unfortunately, our current understanding of the independent contribution of these variables to treatment outcome is extremely limited.

Type 1 diabetes (T1D) in both humans and nonobese diabetic (NOD) mice is an autoimmune disease that results from selective destruction of pancreatic beta cells by T-lymphocytes. Human and murine T1D involve complex B- and CD4+ T-cell responses against a growing list of antigens (Lieberman and DiLorenzo, 2003). Although initiation of T1D clearly requires the recruitment of autoreactive CD4+ T-cells, there is compelling evidence that initiation and progression of T1D is CD8+ T-cell-dependent (Santamaria, 2001; Liblau et al., 2002). Others and we have shown that a large fraction of all islet-associated CD8+ cells in NOD mice use highly homologous TCRTCRα chains (Vα17-Jα42) (Santamaria et al., 1995; Verdaguer et al., 1996; Verdaguer et al., 1997; DiLorenzo et al., 1998) and recognize the same mimotope (NRP-A7) (Anderson et al., 1999). These T-cells are already a significant component of the earliest NOD islet CD8+ infiltrates (DiLorenzo et al., 1998; Anderson et al., 1999; Amrani et al., 2001), are diabetogenic (Verdaguer et al., 1996; Verdaguer et al., 1997), target a peptide from islet-specific glucose 6 phosphatase catalytic subunit-related protein (IGRP$_{206-214}$)(Lieberman et al., 2003), and are unusually frequent in the periphery (~1/200 circulating CD8+ cells) (Lieberman et al., 2003; Trudeau et al., 2003). Notably, progression of insulitis to diabetes in NOD mice is invariably accompanied by cyclic expansion of the circulating IGRP$_{206-214}$-reactive CD8+ T-cell pool (Trudeau et al., 2003), and by avidity maturation of its islet-associated counterpart (Amrani et al., 2000). When considered together, these data strongly support the idea that IGRP$_{206-214}$-reactive CD8+ T-cells play a key role in the initiation and/or progression of murine T1D. Intriguingly, the human igrp gene, which maps to chromosome 2q28-32 (Martin et al., 2001), overlaps a T1D susceptibility locus, IDDM7 (2q31) (Pociot and McDermott, 2002), raising the possibility that IGRP may also be target of the human diabetogenic response.

Administration of soluble peptides (without adjuvant) is an effective way of inducing antigen-specific T-cell tolerance (Aichele et al., 1994; Toes et al., 1996). Previously, we showed that repeated treatment of pre-diabetic NOD mice with soluble NRP-A7 peptide blunted avidity maturation of the IGRP$_{206-214}$-reactive CD8+ T-cell subset by selectively deleting clonotypes expressing TCRs with the highest affinity for peptide/MHC (Amrani et al., 2000). These observations suggested that avidity maturation of pathogenic T-cell populations is a key event in the progression of benign inflammation to overt disease in autoimmunity. However, they also raised the possibility that NRP-A7's anti-diabetogenic activity was mediated by occupation of the "high avidity clonotype niche" (emptied by NRP-A7 treatment) by "low avidity" (and potentially antidiabetogenic) clonotypes. To test this hypothesis, we here identified APLs with partial, full or super agonistic activity for IGRP$_{206-214}$-reactive CD8+ T-cells and compared their anti-diabetogenic activity in vivo over a wide dose-range.

Our data show that wild-type NOD mice spontaneously mount highly prevalent CD8+ T-cell responses against numerous IGRP epitopes, and that peptide therapy aimed at selectively targeting the IGRP$_{206-214}$-reactive CD8+ T-cell subset is effective if it does not delete non-diabetogenic, low avidity clonotypes. Complete depletion of the prevalent IGRP$_{206-214}$-reactive T-cell niche with high doses of IGRP$_{206-214}$ or high affinity APLs was associated with enhanced recruitment of sub-dominant epitope-specific IGRP-reactive T-cell specificities and did not blunt diabetes progression. These data raise important considerations for the design of antigen-specific immunotherapies in autoimmunity.

Materials and Methods

Mice, Cell Lines and Antibodies.

8.3-NOD mice, expressing the TCRαTCRαβ- -rearrangements of the NRPA7/IGRP$_{206-214}$-reactive, H-2K$^d$-restricted beta cell-reactive CD8+ T-cell clone NY8.3 have been described (Verdaguer et al., 1997). NOD mice were purchased from Taconic Farms (Germantown, N.Y.). Anti-Lyt-2 (CD8α) (53-6.7), anti-L3T4 (IM7), anti-Vβ8.1/8.2 (MR5-2), anti-H-2K$^d$ (SF1-1.1), and anti-H-2D$^b$ (KH95) mAbs were from PharMingen (San Diego, Calif.).

Peptides and Peptide Libraries.

The peptide libraries used to identify APLs for this study were prepared using multipin synthesis technology and standard FMOC chemistry (Chiron Technologies, San Diego, Calif.) (Amrani et al., 2001). The first screen was done using NRP-based dipeptide libraries. Libraries capable of eliciting responses were deconvoluted by probing single amino acid variants of NRP. Representative APLs displaying partial, full or super-agonistic activities (FIG. 1) were chosen for in vivo experimentation. Specific single custom peptides were purified through rpHPLC to >80% purity and sequenced by ion spray mass spectrometry (Chiron Technologies, San Diego, Calif.). Peptides were resuspended at 10 mg/ml in 0.1M HEPES (Sigma, St. Louis, Mo.) in 40% acetonitrile (Fisher Scientific, Fair Lawn, N.J.) at pH 7.4, aliquoted at −80° C., and further resuspended in PBS prior to use. This resuspension strategy differs from that used in (Amrani et al., 2000), in that it obviates concentration of diluted stocks of peptide by vacuum centrifugation immediately prior to resuspension in PBS and injection into mice. The latter strategy results in loss of material owing to difficulties in re-solubilization of dried peptide. H-2K$^d$ or H-2D$^b$-binding IGRP peptide libraries were designed by screening the IGRP amino acid sequence with Rankpep (http://mifdfci.harvard.edu/cgi-bin/rankpep.cgi) and SYFPEITHI (http://syfpeithi.bmiheidelberg.com). Pepsets comprised of predicted MHC-binders with scores >39 (rankpep) or >25 (syfpeithi) were synthesized, resuspended as described above, and used for in vitro assays at 10 µM.

Generation of NOD Islet-Derived CD8+ T-Cell Lines.

Islet-derived CD8+ T-cells from peptide-treated or unmanipulated NOD mice were generated by culturing pancreatic islets in complete media (CM: RPMI 1640 media containing 10% fetal bovine serum), containing 0.5 U/ml Takeda rhIL-2 (10-50 islets/well in 24-well plates). The in vivo-activated, IL-2R+ lymphocytes migrating from islets into the culture media were used in functional assays within 6-9 days of islet isolation (Amrani et al., 2000; Anderson et al., 1999).

Proliferation Assays.

Naïve or NRP-A7-differentiated (see below) splenic CD8+ T-cells from 8.3-NOD mice (2×10$^4$/well) were incubated, in duplicate, with peptide-pulsed (0.01, 0.1 and 1 µM), γ-irradiated (3,000 rad) NOD splenocytes (10$^5$/well) for 3 days at 37° C. in 5% CO$_2$. Cultures were pulsed with 1 µCi of ($^3$H)-thymidine during the last 18 hours of culture and harvested.

Cytokine Secretion.

Naïve splenic CD8+ T-cells from 8.3-NOD mice (2×10$^4$/well) were incubated with peptide-pulsed (0.001, 0.01, 0.1, 1 and/or 10 µM) γ-irradiated NOD splenocytes (10$^5$/well) in 96-well plates for 48 hours at 37° C. Short-term islet-derived T-cell lines from peptide-treated or unmanipulated NOD mice (adjusted at 2×10$^4$ CD8+ T-cells/well) were tested the same way, but using 10 µM of peptide. The supernatants (100 µl/well) were assayed in duplicate for IL-2, IL-4, and/or IFN-γ content by ELISA using commercially available kits (Genzyme Diagnostics, Cambridge, Mass.).

Tetramer Staining.

Tetramers were prepared and used as described in (Amrani et al., 2000). Hand-picked pancreatic islets from individual mice were cultured in complete media supplemented with 0.5 U/ml of Takeda rhIL-2 for 7-9 days. T-cells (10$^6$ per 20 µl) were then stained for 45 minutes on ice in 20 µl of wash media (0.2% sodium bicarbonate, 0.1% sodium azide and 2% FBS in RPMI-1640) containing anti-CD8-FITC (clone YTS169.4; 0.5 µg) and tetramer (85.5 nM). After washing, the cells were resuspended in wash media and analyzed with a flow cytometer (Becton Dickinson). For the analysis of tetramer staining at equilibrium, T-cells were stained for 2 hours at room temperature with 20 µl of wash media (0.2% sodium bicarbonate, 0.1% sodium azide and 2% FBS in RPMI-1640) containing anti-CD8α-FITC (clone YTS169.4; 0.5 µg) and different concentrations of tetramers (8.55, 17.1, 42.75 and 85.5 nM). After washing, cells were resuspended in 100 µl of wash media, fixed in 0.4% paraformaldehyde and analyzed with a flow cytometer. The apparent K$_d$ values were determined by plotting the negative reciprocal of the slope of the line fit to Scatchard plots of fluorescence units (median of CD8+ population tetramer staining)/nM versus fluorescence units.

H-2K$^d$-stabilization assay. RMA-SK$^d$ cells that had been cultured overnight at 26° C. were seeded, in quadruplicate, at 10$^4$ cells/well in 96-well plates, pulsed with peptides in RPMI-1640, 0.25% BSA for 1 hour at 26° C., incubated at 37° C. for 3 hours, washed, stained with anti-H-2K$^d$-FITC or anti-H-2D$^b$-FITC, and the mean fluorescence intensity (mfi) for MHC class I expression analyzed by flow cytometry (Anderson et al., 1999). Controls used included TUM (H-2K$^d$-binder), LCMV-GP33 (H-2D$^b$-binder) and no peptide. The dissociation constant (K$_d$) was measured by repeating the experiments described above except using different concentrations of peptides (10 µl, 0.1, 0.01, 0.001 µM). The K$_d$ values were calculated as the concentration of peptide required to rescue 50% of the H-2K$^d$ molecules on RMA-SK$_d$ cells (100% at 10 µM).

Peptide Treatment.

Cohorts of 3-to-4 week-old female NOD mice were injected with 1-100 µg of peptide in PBS intraperitoneally. This was repeated every 2 weeks until the 7-8th week, and every 3 weeks thereafter. Mice were monitored for development of hyperglycemia until at least the 28th week of age. The 8.3-CD8+ T-cell tolerogenic activity of APLs was determined by treating 8-15 wk-old 8.3-NOD mice with one i.p. injection of 100 µg of peptide. Peptide-treatment experiments employing older mice (28-30 wk-old) and NRP-A7 yielded results statistically similar to those seen in younger mice, indicating that reductions in transgenic T-cell numbers resulting from peptide treatment were independent of the age of mice. Mice were sacrificed a week after treatment, and their spleens analyzed for presence of 8.3-CD8+ T-cells by flow cytometry.

Statistical Analyses.

Data were compared using linear regression and variance analysis, Mann-Whitney U test or $\chi^2$.

Results

APLs for IGRP$_{206-214}$-Reactive CD8+ T-Cells.

Figure 5:
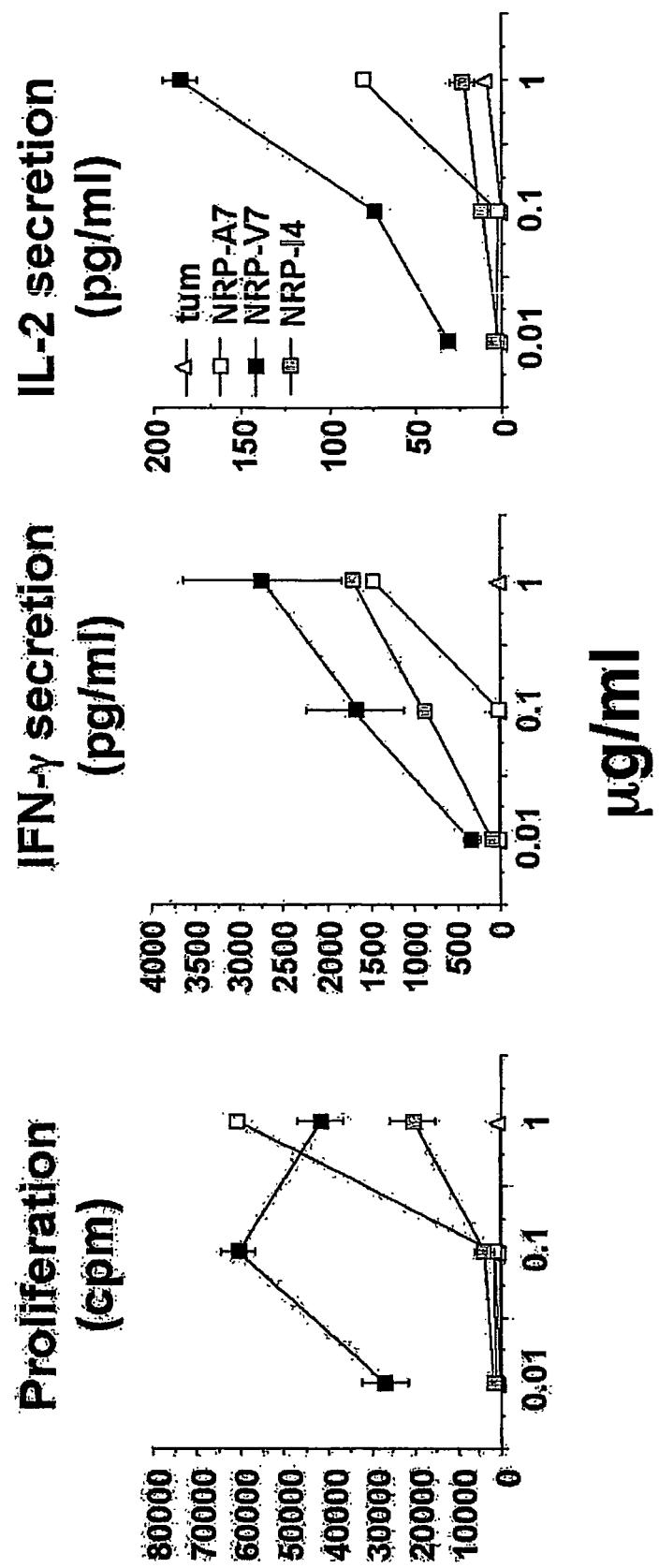
FIG. 5 is graphs of experimental results showing the agonistic activity of APLs of 8.3-CD8+ T-cells. Naïve splenic 8.3-CD8+ cells ($2×10^4$) were incubated, in duplicate, with peptide-pulsed (0.01-1 μM), γ-irradiated NOD splenocytes ($10^5$) for 2 or 3 days (cytokine secretion and proliferation assays, respectively) and pulsed with 1 μCi of ($^3H$)-thymidine, harvested and counted (for proliferation assays). The supernatants of the 2 day cultures (100 µl) were assayed for IL-2, IL-4 and/or IFN-γ by ELISA. None of the libraries induced IL-4 secretion (not shown). Data are mean±SE and are representative of two or three different experiments.
Figure 6:
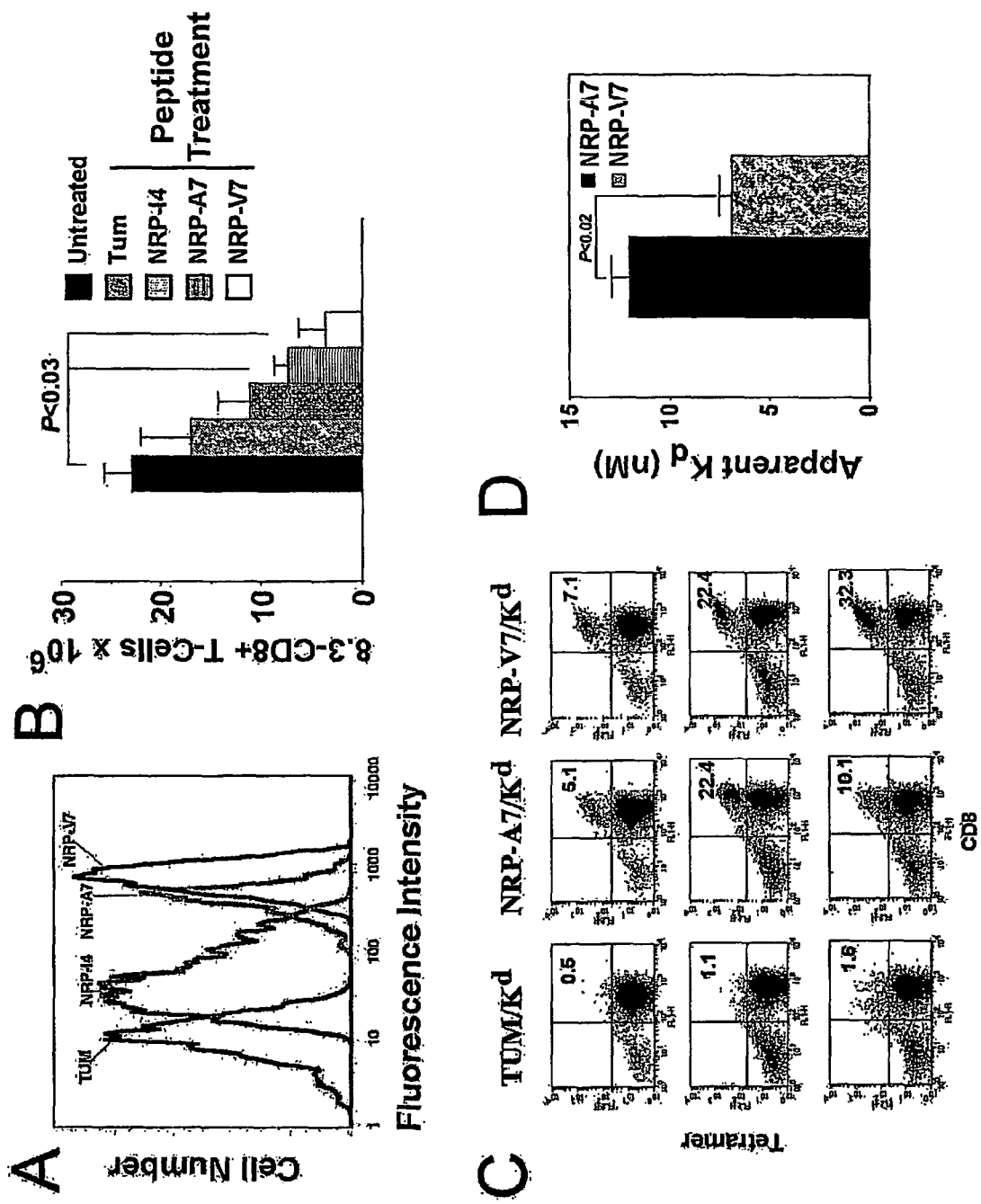
FIG. 6 is graphs of experimental results showing differences in the functional avidity of APLs correlate with differences in peptide/MHC-binding avidity and tolerogenic activity. Panel A shows the fluorescence intensity of tetramer staining. Naïve splenic 8.3-CD8+ T-cells were stained with different APL/$K^d$-PE tetramers and a CD8-FITC mAb. Panel B shows the tolerogenic activity of APLs against 8.3-CD8+ T-cells in vivo. The graph compares total numbers of total CD8+ splenocytes in untreated (10±1 wk-old; n=9) or APL-treated 8.3-NOD mice. Mice received 11.p. injection of 100 µg of peptide in PBS 7 days prior to analysis. The age and number of mice that were studied is as follows: TUM-treated (11±1 wk-old; n=5); NRP-I4-treated (9±1 wk-old; n=3); NRP-A7-treated (11±1 wk-old; n=7); and NRP-V7-treated (14±2 wk-old; n=3). Panel C shows tetramer-binding ability of islet-associated CD8+ T-cells from 20 wk-old non-transgenic NOD mice. Vertical panels correspond to three individual mice. Numbers in the upper right quadrants of each panel correspond to percentage of tetramer-positive CD8+ cells. Note that NRP-V7 stains these cells with higher fluorescence intensity than NRP-A7. Panel D shows CD8+ T-cells propagated from islets of 9 wk-old female NOD mice bind NRP-V7/$K^d$ tetramers (n=6 mice) with higher avidity (lower $K_d$) than NRPA7/$K^d$ (n=6 mice).

We first searched for NRP APLs capable of engaging the 8.3-TCR with different affinity, as compared to NRP-A7. This work, which was initiated well before the discovery of IGRP206-214, involved generating numerous single amino acid mutants of NRP and testing their ability to elicit 8.3-CD8+ T-cell responses (Amrani et al., 2001). NRP-I4 was chosen as a potential "low avidity" APL candidate, since it behaved as a partial agonist; it was quite efficient at triggering IFN-γ secretion by naïve 8.3-CD8+ T-cells, but significantly less efficient than NRP-A7 at inducing other responses (FIG. 5). NRP-V7 was chosen as a potential "very high avidity" APL because it had superior agonistic activity on 8.3-CD8+ T-cells than NRP-A7 (agonist) (FIG. 5). To confirm that these peptides were in fact recognized with different avidity by 8.3-CD8+ cells (they all bound to K$^d$ with similar avidity, as determined by the RMA-SK$^d$ stabilization assay; data not shown), we tested the ability of the corresponding peptide/MHC tetramers to stain naïve 8.3-CD8+ cells. As shown in FIG. 6A, the tetramer staining intensities were consistent with the functional avidities of the different peptides (FIG. 5). The functional avidity of these peptides also correlated well with their tolerogenic activity in vivo. Treatment of 8.3-NOD mice, expressing a TCR that recognizes NRP-V7 with intermediate-to-high avidity (our unpublished data), with a single injection of NRP-V7 (100 µg in PBS) contained fewer 8.3-CD8+ splenocytes than 8.3-NOD mice treated with NRP-A7 or NRP-I4 (FIG. 6B).

Experiments employing CD8+ cells derived from pancreatic islets of wild-type NOD mice indicated that differential binding of each of these peptide/K$^d$ complexes by IGRP$_{206-214}$-reactive CD8+ T-cells was not a peculiarity of cells expressing the 8.3-TCR. Whereas the NRP-I4 tetramer could not stain T-cells derived from islets of 20 wk-old wild-type NOD mice above the threshold for detection by flow cytometry (data not shown), the NRP-V7 tetramer generally did so with higher fluorescence intensity than the NRP-A7 tetramer (FIG. 6C). Quantitative measurements of avidity confirmed these results. NRP-V7 tetramers bound CD8+ cells derived from pancreatic islets of 9 wk-old NOD mice with significantly lower $K^d$ (higher avidity) than NRP-A7 (FIG. 6D). As a whole, these data demonstrate that $IGRP_{206-214}$-reactive CD8+ cells recognize NRP-I4, NRP-A7 and NRP-V7 with increasing affinity, both in vitro and in vivo.

$IGRP_{206-214}$APLs Can Curb the Progression of T1D in NOD Mice but Only within a Narrow Range of Dose and Affinity.

Figure 7:
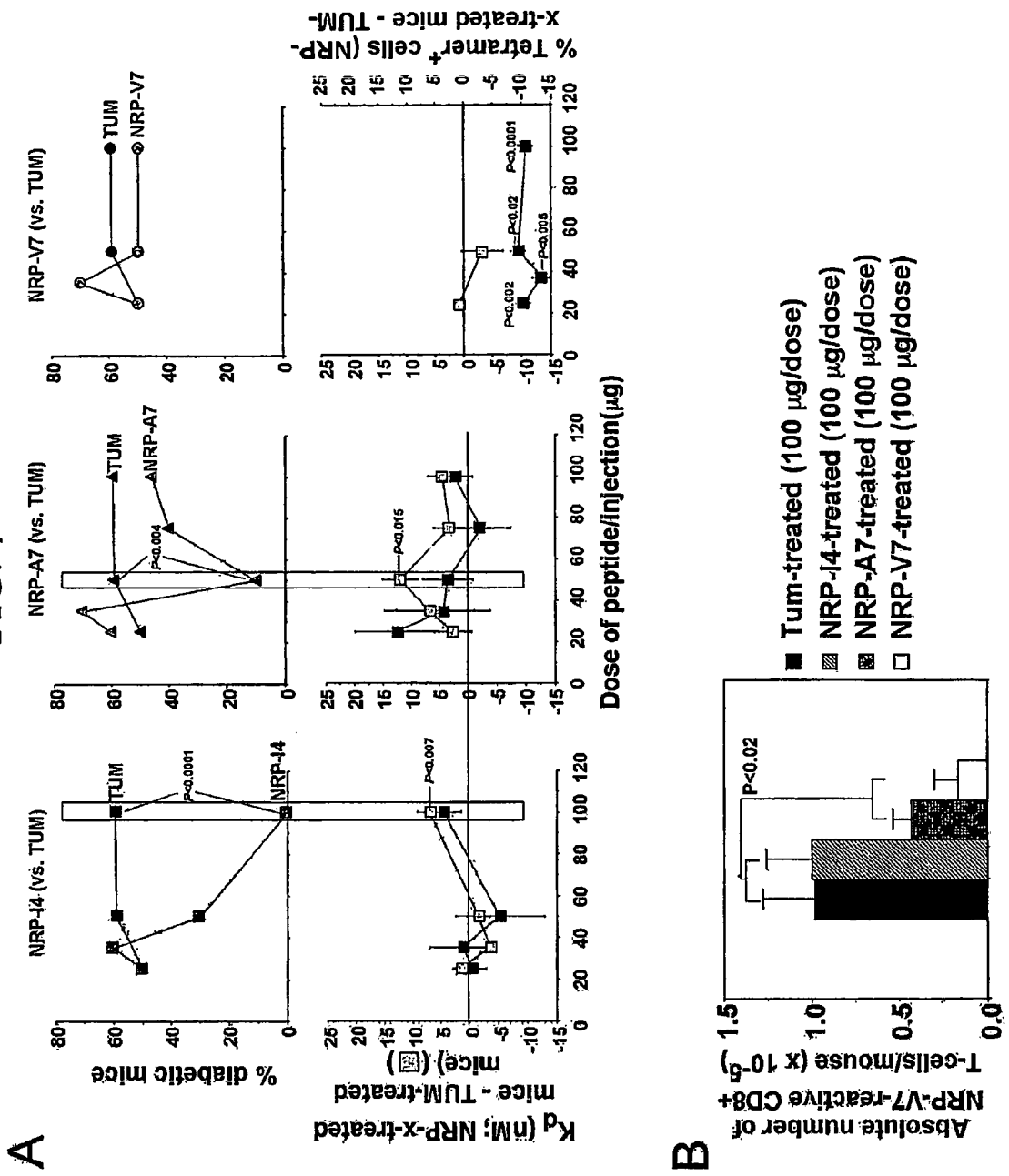
FIG. 7 is graphs of experimental results showing the anti-diabetogenic activity of APLs in wild-type NOD mice. Panel A (upper graphs) show the incidence of diabetes in TUM vs. APL-treated female NOD mice. N values were as follows: TUM:≤25 µg (n=29), 50 µg (n=10), 100 µg (n=69); NRP-I4: µg (n=30), 35 µg (n=10), 50 µg (n=10), 100 µg (n=10); NRP-A7: ≤25 µg (n=29), 35 µg (n=10), 50 µg (n=10), 75 mg (n=10), 100µg (n=50); NRPV7: ≤25 µg (n=30), 35 µg (n=10), 50 µg (n=10), 100 µg (n=59). Panel A (lower graphs) show the effects of APL vs. TUM-treatment on the percentages and avidity of NRP-V7/$K^d$ tetramer-binding cells within islet-derived CD8+ cells. Mice were sacrificed at diabetes onset or at the end of the study (32 wk) to isolate islet-associated CD8+ T-cells. Data are presented as differences in values obtained in APL- vs. TUM-treated mice (x±SE). Values above or below zero indicate that APL treatment resulted in recruitment of low or high avidity T-cells, and/or in recruitment of higher or lower percentages of tetramer-reactive CD8+ T-cells, respectively. N values were as follows: NRP-I4: ≤25 µg (n=15, 7 T1D), 35 µg (n=4, 3 T1D), 50 µg (n=3, 1 T1D), 100 µg (n=7, 0 T1D); NRP-A7: <25 µg (n=9, 5 T1D), 35 µg (n=4, 4 T1D), 50 µg (n=5, 1 T1D), 75 µg (n=3, 0 T1D), 100 µg (n=10); NRP-V7: <25 µg (n=10, 7 T1D), 35 µg (n=6, 3 T1 D), 50 µg (n=10, 5 T1D), 100 µg (n=47, 31 T1D). Measurements of avidity were only possible in mice containing tetramer-positive cells in islets. The n values were as follows: NRP-I4: ≤25 µg (n=15), 35 µg (n=4), 50 µg (n=2), 100 µg (n=7); NRP-A7: <25 µg (n=6), 35 µg (n=4), 50 µg (n=5), 75 µg (n=2), 100 µg (n=10); NRP-V7: ≤25 µg (n=7), 50 µg (n=2). Panel B shows the absolute number of NRP-V7/$K^d$ tetramer-binding CD8+ T-cells in mice treated with different peptides at 100 µg/injection.

We next investigated whether the anti-diabetogenic activity of the above APLs was a function of "avidity", as defined not only by the affinity of individual peptide/MHC complexes for specific TCRs, but also by the absolute number of peptide/MHC complexes that are available for recognition (i.e. dose of peptide). This was done by treating cohorts of female NOD mice with repeated injections of TUM (negative control), NRP-I4, NRP-A7 and NRP-V7 (in PBS) over a wide dose range, and by following the mice for development of diabetes (FIG. 7A, top). Starting at 3-4 weeks of age, mice received one injection of peptide i.p. every 2 (first three doses) or 3 weeks after initiation of treatment. Mice were sacrificed at diabetes onset or at the end of the follow-up period (28-32 weeks), to investigate the effects of treatment on the size and tetramer-binding avidity of the islet-associated $IGRP_{206-214}$-reactive CD8+ T-cell subpopulation (FIG. 7A, bottom).

NRP-I4 was anti-diabetogenic in a dose-dependent manner: it was not protective at all when given at <20 μg/injection, but was highly anti-diabetogenic when given at 100 μg/injection (FIG. 7A, top). Strikingly, the protective effect of NRP-I4 (at 100 μg/injection) was associated with recruitment of low avidity $IGRP_{206-214}$-reactive CD8+ cells into islets, rather than with massive deletion of the $IGRP_{206-214}$-reactive CD8+ cell subset. Thus, the percentages (FIG. 7A, bottom, right y axis) and absolute numbers (FIG. 7B) of NRP-V7-reactive CD8+ cells contained in the islets of these mice were similar to those seen in TUM-treated controls. Furthermore, the islet-associated CD8+ cells of NRP-I4-treated mice bound NRP-V7 tetramers with significantly lower avidity than those derived from islets of TUM-treated mice (left y axis) (the values shown in FIG. 7A reflect differences between these two groups of mice). The most logical interpretation of these results is that the protective effect of high-dose NRP-I4 treatment resulted from selective deletion of high-avidity $IGRP_{206-214}$-reactive CD8+ cells. In agreement with this view, NRP-A7, a higher affinity ligand of $IGRP_{206-214}$-reactive CD8+ cells, protected mice from diabetes at a lower dose than NRP-I4 (50 μg/injection), and this, too, coincided with accumulation of low avidity $IGRP_{206-214}$-reactive CD8+ T-cells within islets (FIG. 7A, bottom). The absolute number of NRP-V7-reactive T-cells in the islets of these mice were reduced, but not significantly, as compared to TUM-treated mice ($0.6 \times 10^5 \pm 0.3$ vs. $1 \times 10^5 \pm 0.3$, respectively).

However, this interpretation that protection by high doses of NRP-I4 and intermediate doses of NRP-A7 was due solely to deletion of high avidity clonotypes was at odds with two unexpected observations. First, high doses of NRP-A7 (100 μg/injection) were ineffective. It should be noted that here we prepared the inoculum by diluting concentrated stocks of peptide with vehicle, as opposed to by dissolving material dried from diluted stocks (Amrani et al., 2000). As the latter strategy results in peptide loss (our observations), it should not be a surprise that in a previous study NRP-A7 was protective when given at the "100 μg" dose (Amrani et al., 2000). The second unexpected observation was that NRP-V7 (an even higher affinity ligand of $IGRP_{206-214}$-reactive CD8+ T-cells than NRP-A7) was not significantly protective at any dose (FIG. 7A, top). This was puzzling because the islets of NRP-A7-(100 μg/dose) and NRP-V7-treated mice (over a range of doses) either contained significantly reduced numbers of NRP-V7-reactive CD8+ cells, or were almost completely devoid of these T-cells, respectively (FIGS. 7A, top, and 7B). Thus, the anti-diabetogenic activity of NRP-I4 (at 100 μg) and NRP-A7 (at 50 μg) could not be attributed to deletion of (high avidity) $IGRP_{206-214}$-reactive CD8+ cells alone. Rather, the data suggested that protection required the recruitment of low avidity $IGRP_{206-214}$-reactive CD8+ cells to islets. Presumably, these low avidity cells would promote a state of chronic, yet non-pathogenic inflammation.

Wild-Type NOD Mice Spontaneously Mount CD8+ T-Cell Responses Against Numerous IGRP Epitopes.

Figure 8:
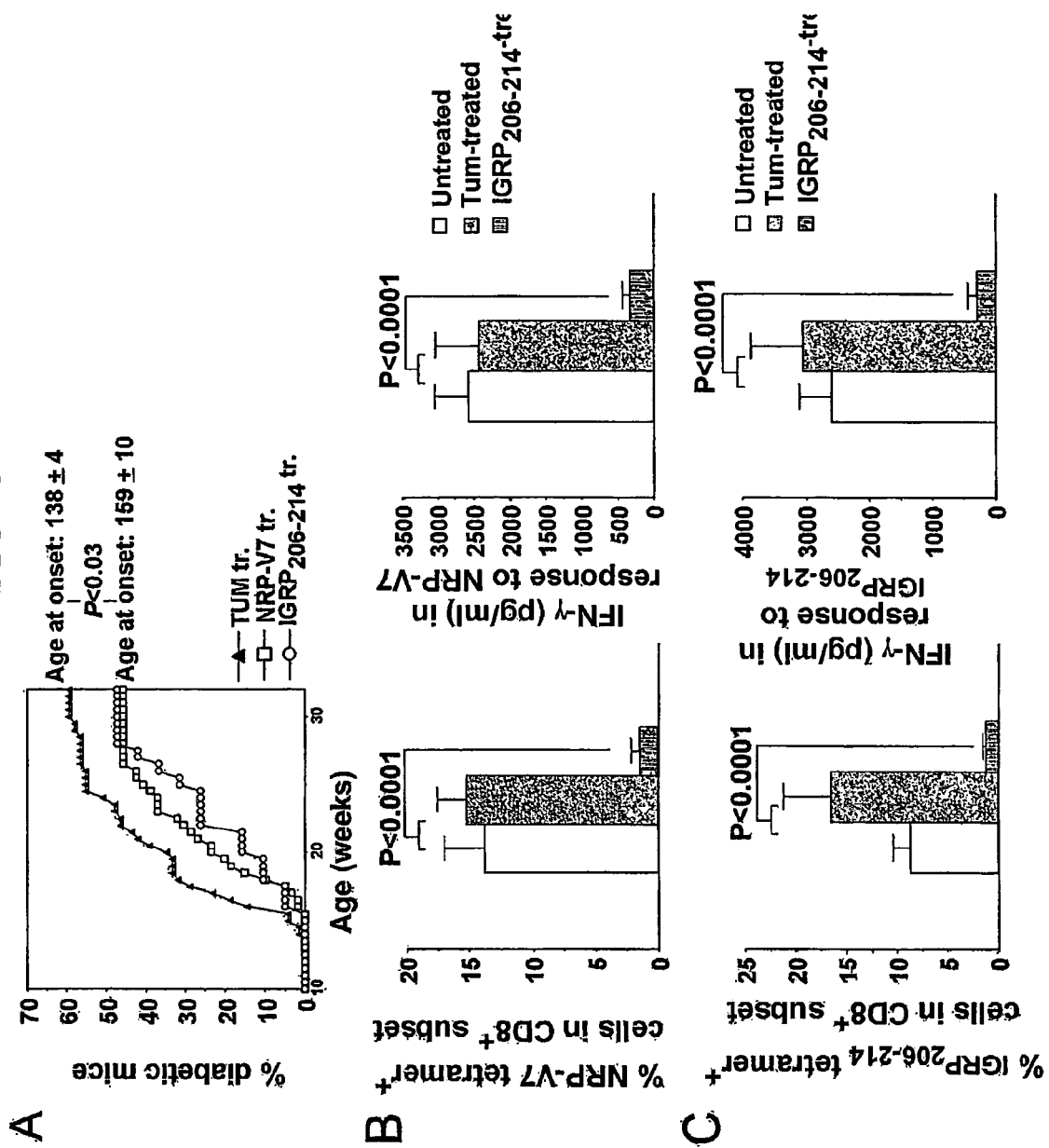
FIG. 8 is graphs of experimental results demonstrating that NRP-V7 and IGRP$_{206-214}$ cannot blunt diabetes progression despite depleting the IGRP$_{206-214}$-reactive CD8+ T-cell pool. Panel A shows the cumulative incidence of T1D in TUM (n=69), NRP-V7 (n=59) and IGRP$_{206-214}$-treated NOD mice (n=19). All mice received 100 µg (TUM, NRP-V7 and IGRP$_{206-214}$) or 75 µg of peptide/injection (IGRP$_{206-214}$; n=9). No differences were noted in mice receiving 75 or 100 µg of IGRP$_{206-214}$, hence the data were pooled. Panel B shows the percentage of NRP-V7/$K^d$ tetramer-reactive cells (left) and IFN-γ secretion (right) by islet-associated CD8+ T-cells from untreated, or TUM- and IGRP$_{206-214}$-treated NOD mice. No significant differences were noted between diabetic and non-diabetic mice within individual treatment groups. N values for tetramer staining were: Untreated group: n=11 (2 diabetic); TUM-treated group: n=20 (9 diabetic); NRP-V7-treated group: n=52 (32 diabetic); IGRP$_{206-214}$-treated group: n=17 (8 diabetic). N values for IFN-γ secretion were: Untreated group: n=28 (19 diabetic); TUM-treated group: n=11 (7 diabetic); and IGRP$_{206-214}$-treated group: n=12 (6 diabetic). Panel C is the same as Panel B, but employing IGRP$_{206-214}$/$K^d$ tetramers or IGRP$_{206-214}$ peptide. N values for tetramer staining were: Untreated group: n=28 (19 diabetic); TUM-treated group: n=3 (0 diabetic); IGRP$_{206-214}$-treated group: n=14 (6 diabetic). N values for IFN-γ secretion were: Untreated group: n=29 (9 diabetic); TUM-treated group: n=7 (4 diabetic); and IGRP$_{206-214}$-treated group: n=11 (5 diabetic).

Treatment of NOD mice with high doses of $IGRP_{206-214}$ (75-100 μg/injection) yielded results very similar to those obtained in NRP-V7-treated mice: this peptide delayed the age at onset of diabetes, but did not significantly reduce its incidence (FIG. 8A). Notably, the ineffectiveness of $IGRP_{206-214}$ treatment was also associated with near complete deletion of the intra-islet $IGRP_{206-214}$-reactive CD8+ T-cell subpopulation, as determined by both flow cytometry (FIGS. 8B and C, left panels) and functional assays employing islet-derived T-cells (FIGS. 8B and C, right panels).

Figure 9:
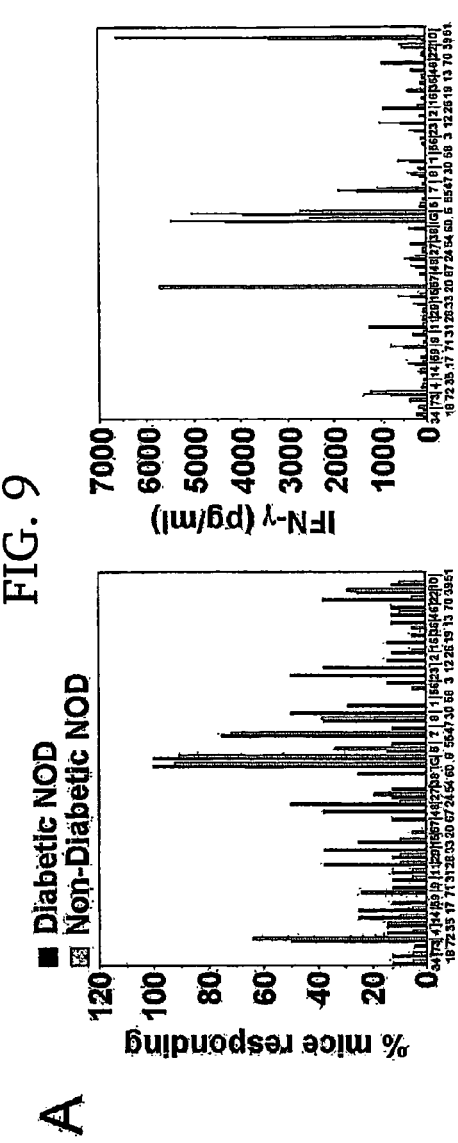
FIG. 9 is graphs of experimental results showing that NOD mice spontaneously mount intra-islet CD8+ T-cell responses against multiple IGRP epitopes. Panel A (left) shows the percentage of diabetic and non-diabetic NOD mice that contain intra-islet CD8+ T-cells recognizing epitopes of IGRP. Panel A (right) shows the average amounts of IFN-γ secreted by islet-derived CD8+ T-cells from mice that responded to the corresponding peptide (excluding mice that did not respond). Data are from Table II. Panel B shows examples of mice containing IGRP$_{324-332}$- or IGRP$_{21-29}$-reactive CD8+ T-cells within islets, as determined with tetramers. Panel C shows the cumulative amounts of IFN-γ secreted by islet-derived CD8+ T-cells in response to IGRP peptides.
Figure 9:
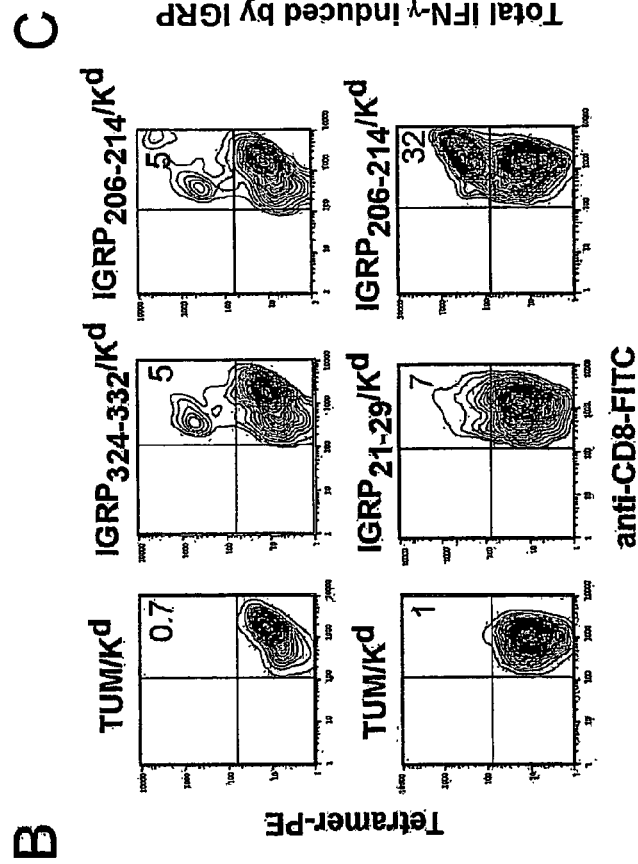
Figure 9:
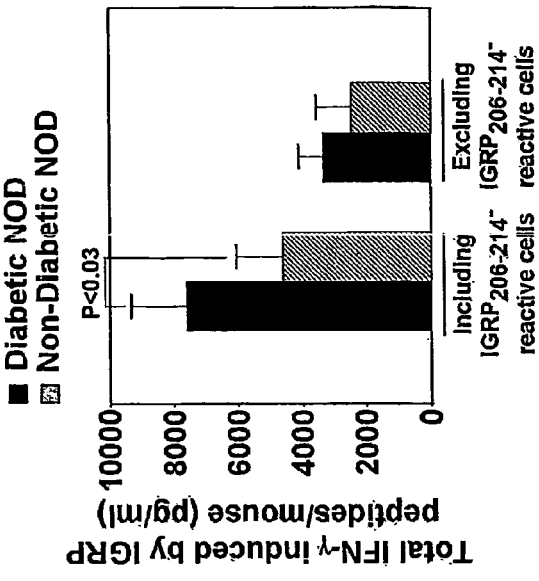

These results prompted us to consider the possibility that near complete deletion of the $IGRP_{206-214}$-reactive CD8+ subset (by NRP-V7 or $IGRP_{206-214}$ treatment) might have somehow fostered the creation of a "niche" for subdominant autoreactive T-cell specificities in islets. Conceivably, recruitment and/or accumulation of these clonotypes could have counteracted any protection afforded by deletion of the dominant $IGRP_{20-214}$-reactive pool. Since staining of islet-derived T-cells of TUM-versus NRP-V7- or $IGRP_{206-214}$-treated mice with high avidity insulin 15-23/$K^d$ (InsL) tetramers (the only other known target of beta cell autoreactive CD8+ cells (Wong et al., 1999)), did not reveal significant differences (data not shown), we wondered whether the anti-IGRP-CD8+ cell response in diabetes involved multiple epitopes. To investigate this, we designed an IGRP-based peptide library comprised of 76 MHC class I-binding nonamers (33 $K^d$- and 43 $D^b$-binding) (Table I, ordered based on their location in IGRP; from amino to carboxy termini). Only one of these peptides ($IGRP_{207-215}$; peptide "6") was cross-reactive with $IGRP_{206-214}$ (peptide "IG") as determined by its ability to elicit 8.3-CD8+ T-cell responses (data not shown). We then tested the ability of each of these IGRP peptides, as well as NRP-V7 and TUM (at 10 μM) to elicit IFN-γ secretion by CD8+ cells propagated from islets of pre-diabetic (21±1 weeks) or acutely diabetic NOD mice (18+1 weeks) (Table II and FIG. 9A). Although most mice, regardless of diabetes status, contained $IGRP_{206-214}$ (and $IGRP_{207-215}$)-reactive CD8+ T-cells in islets (peptides "IG" and "6", respectively) Table II and FIG. 9A, left panel), cells derived from the diabetic mice mounted more vigorous responses against these two epitopes than cells derived from non-diabetic animals (FIG. 9A, right panel, which excludes non-responder mice (<50 pg/ml)). Experiments employing $IGRP_{206-214}$ tetramers confirmed the existence of a correlation between the magnitude of IFN-γ secretion by islet-associated CD8+ T-cells and the percentage of tetramer-positive cells (p<0.001), suggesting that the above differences in IFN-γ secretion reflected differences in cell numbers (data not shown). Interestingly, a significant number of mice also mounted responses against other IGRP epitopes, particularly peptides 72, 7, 8 and 39. Limited studies with tetramers confirmed the presence of peptide 72 and peptide 39-reactive CD8+ T-cells in at least some animals (FIG. 9B). Comparison of the magnitude of the total anti-IGRP responses further indicated that whereas the response against IGRP$_{206-214}$ was significantly higher in diabetic animals than in non-diabetic ones, the combined response against other IGRP epitopes (excluding IGRP$_{206-214}$) was not (FIG. 9C). This is consistent with the hypothesis that progression to overt diabetes involves the recruitment of IGRP$_{206-214}$-reactive clonotypes, as we have previously proposed (Amrani et al., 2000; Lieberman et al., 2003).

TABLE I

IGRP-Specific Peptide Library

| # | SEQUENCE | RESIDUES | # | SEQUENCE | RESIDUES |
|---|---|---|---|---|---|
| 25 | DFLHRSGVL | 2-10 | 62 | LFALGFYLL | 216-224 |
| 26 | FLHRSGVLI | 3-11 | 63 | FALGFYLLL | 217-225 |
| 27 | SGVLIIHHL | 7-15 | 64 | LGFYLLLRL | 219-227 |
| 28 | DYRTYYGFL | 18-26 | 10 | LRLFGIDLL | 225-231 |
| 29 | TYYGFLNFM | 21-29 | 66 | FGIDLLWSV | 228-236 |
| 30 | GFLNFMSNV | 24-32 | 67 | WSVFWLIQI | 234-242 |
| 31 | SNVGDPRNI | 30-38 | 68 | KWCANPDWI | 241-249 |
| 32 | GDPRNIFSI | 33-41 | 69 | CANPDWIHI | 243-251 |
| 33 | IYFPLWFQL | 41-49 | 70 | PFAGLVRNL | 255-263 |
| 34 | LWFQLNQNV | 45-53 | 71 | GLVRNLGVL | 258-266 |
| 35 | QLNQNVGTK | 48-56 | 72 | RNLGVLFGL | 261-269 |
| 36 | LNQNVGTKM | 49-57 | 73 | VLFGLGFAI | 265-273 |
| 37 | NQNVGTKMI | 50-58 | 74 | LGFAINSEM | 269-277 |
| 38 | WFNLIFKWI | 66-74 | 75 | GFAINSEMF | 270-278 |
| 39 | FGHRPYWWI | 76-84 | 76 | FAINSEMFL | 271-279 |
| 40 | IYPNHSSPC | 89-97 | 77 | CQGENGTKP | 282-290 |
| 41 | YPNHSSPCL | 90-98 | 78 | GTKPSFRLL | 287-295 |
| 42 | GHAMGSSCV | 114-122 | 79 | SFRLLCALT | 291-299 |
| 43 | VWYVMVTAA | 122-130 | 80 | RLLCALTSL | 293-301 |

TABLE I-continued

IGRP-Specific Peptide Library

| # | SEQUENCE | RESIDUES | # | SEQUENCE | RESIDUES |
|---|---|---|---|---|---|
| 44 | WYVMVTAAL | 123-131 | 81 | CALTSLTTM | 296-304 |
| 45 | ALSYTISRM | 130-138 | 82 | LTSLTTMQL | 298-306 |
| 46 | YTISRMEES | 133-141 | 83 | TSLTTMQLY | 299-307 |
| 47 | ISRMEESSV | 135-143 | 84 | MQLYRFIKI | 304-312 |
| 48 | SRMEESSVT | 136-144 | 85 | RFIKIPTHA | 308-316 |
| 49 | RMEESSVTL | 137-145 | 86 | KIPTHAEPL | 311-319 |
| 50 | ESSVTLHRL | 140-148 | 87 | THAEPLFYL | 314-322 |
| 51 | SFLWSVFWL | 151-159 | 88 | HAEPLFYLL | 315-323 |
| 4 | FLWSVFWLI | 152-160 | 89 | LSFCKSASI | 323-331 |
| 53 | VFWLIQISV | 156-164 | 90 | SFCKSASIP | 324-332 |
| 54 | SRVFIATHF | 167-175 | 91 | CKSASIPLM | 326-332 |
| 55 | ATHFPHQVI | 172-180 | 92 | SIPLMVVAL | 330-338 |
| 56 | THFPHQVIL | 173-181 | 93 | IPLMVVALI | 331-339 |
| 57 | FEHTPGVHM | 193-201 | 94 | ALIPYCVHM | 337-345 |
| 58 | TPGVHMASL | 196-204 | | | |
| 59 | HMASLSVYL | 200-208 | | | |
| 60 | LSVYLKTNV | 204-212 | | | |
| 61 | YLKTNVFLF | 207-215 | | | |

Table II, shown on the following two pages, illustrates peptides ordered from the amino to the carboxy terminus of IGRP. Only peptides that elicited a response in at least one mouse are shown. Symbols: M#=mouse number; IU=diabetic, non-peptide-treated mice; N=non-diabetic, non-peptide-treated mice; IT=diabetic, TUM peptide-treated mice; T=non-diabetic, TUM peptide-treated mice; IIG=diabetic IGRP$_{206-214}$ peptide-treated mice; IG=non-diabetic, IGRP$_{206-214}$ peptide-treated mice; nd=not determined. Significant responses are shaded.

TABLE II

Amounts of IFN-γ (pg/ml) secreted by islet-derived CD8+ T-cells

| M# | Age wk | 34 (Kd) | 18 (Db) | 73 (Kd) | 72 (Kd) | 4 (Db) | 35 (Kd) | 44 (Db) | 17 (Db) | 59 (Kd) | 71 (Kd) | 9 (Db) | 31 (Db) | 11 (Db) | 28 (Db) | 29 (Db) | 15 (Db) | 20 (Db) | 57 (Kd) | 67 (Kd) | 48 (Db) | 24 (Db) | 27 (Db) | 54 (Db) | 38 (Kd) | 60 (Kd) |
|---|---|---|---|---|---|---|---|---|---|---|---|---|---|---|---|---|---|---|---|---|---|---|---|---|---|---|
| IU1 | 12 | | | | | | | | | | | | | | | | | | | | | | | | | 82 |
| IU2 | 13 | | | | 105 | | | | | | | | | | | | | | | | | | | | | 354 |
| IU3 | 20 | | | | 2342 | nd | | | | 95 | | | | | 63 | | 604 | | | 134 | 66 | 110 | | 330 | | |
| IU4 | 17 | 69 | 68 | | 161 | 94 | | 63 | 78 | | | 52 | | | 54 | | | | | | 439 | 631 | 72 | | | |
| IU5 | 23 | | | | 267 | | 61 | | | | | | | | 71 | 76 | 61 | | | | | 125 | | | | |
| IU6 | 21 | | | | | | | 177 | 385 | | | | 282 | | | | | | | | 100 | 468 | | | | |
| IU7 | 19 | 201 | 168 | | 100 | | | 141 | | | 90 | | | | | | 144 | | | | | 225 | 90 | | | |
| IU8 | 17 | | | | | | | | | | 337 | | | 52 | | | | | | | | | 102 | | | |
| N1 | 17 | | | | | | | | | | | | | 1225 | | | | | | | | | | | | |
| N2 | 21 | | | | 2988 | | | | | | | | 50 | | | | | | | | | | | | | |
| N3 | 25 | | | | | | | | | | | | | | | | | | | | | | | | | |
| N4 | 25 | | | | 4707 | | | | | | 222 | 54 | | | | | | | | | | | | | | |
| N5 | 21 | | | | 996 | | | 55 | 72 | | | | | | | | | 5710 | | | | | | | | |
| N6 | 21 | | | | 255 | | | | | | | | | | 61 | 59 | | | | | | 54 | 51 | | | |
| N7 | 25 | | | | 1438 | | | | | | | | | | | | | | | | | | | | | |
| N8 | 25 | | | | | | | | | | | | | | | | | | | | | | | | | |
| N9 | 19 | | | | 150 | | | | | | | | | | | | | | | | | | | | | |
| N10 | 19 | | | | 193 | | | | | | | | | | | | | | | | | | | | | |
| N11 | 19 | | | | 343 | | | | | | | | | | 61 | 52 | | | | | | | 54 | | | |
| N12 | 19 | | | | 1491 | | | | | | | | | | | | 53 | | | | | | | | | |
| N13 | 21 | | | | | | | | | | | | | | | | | | | | | | | | | |
| N14 | 21 | | | | | | | | | | | | | | | | | | | | | | | | | |
| N15 | 21 | | | | | | | | | | | | | | | | | | | | | | | | | |
| N16 | 20 | | | | 84 | | | | | | | | | | | | | | | | | | | | | |
| N17 | 20 | | | | 229 | | | | | | 1947 | | | | | | | | | | | | | | | |
| N18 | 19 | | | | | | | | | | | | | | | | | | | | | | | | | |
| N19 | 20 | | | | | | | | | | | | | | | | | | | | | | | | | |
| N20 | 20 | | | | | | | | | | | | | | | | | | | | | | | | | |

TABLE II-continued

Amounts of IFN-γ (pg/ml) secreted by islet-derived CD8+ T-cells

| | | | | | | | | | | | | | | | | | | | | | | |
|---|---|---|---|---|---|---|---|---|---|---|---|---|---|---|---|---|---|---|---|---|---|---|
| N21 | 19 | nd | nd | | | 96 | 65 | nd | nd | nd | nd | nd | nd | nd | nd | nd | nd | nd | nd | nd | nd | nd |
| N22 | 16 | nd | nd | | | 181 | nd | nd | nd | nd | nd | nd | nd | nd | nd | nd | nd | nd | nd | nd | nd | nd |
| N23 | 24 | nd | nd | | | 725 | nd | nd | nd | nd | nd | nd | nd | nd | nd | nd | nd | nd | nd | nd | nd | nd |
| N24 | 18 | nd | nd | | 358 | 194 | nd | nd | nd | nd | nd | nd | nd | nd | nd | nd | nd | nd | nd | nd | nd | nd |
| N25 | 23 | nd | nd | | | 223 | | 62 | | | | | | | | | | | | | 300 | |
| IT1 | 16 | | | | | 210 | | | 57 | | | | | | | | | | | | 288 | |
| IT2 | 16 | | | | | 498 | | | | | | | | | | | | | | | | |
| IT3 | 15 | | | | | 498 | | | | | | | | | | | | | 50 | | | 105 |
| IT4 | 20 | | | | | 1920 | | | | 132 | | | | | | | | | 50 | | | |
| T1 | 21 | 70 | 77 | | | | 96 | 61 | | 71 | 77 | 51 | 85 | | 70 | | | 57 | 72 | | | |
| T2 | 20 | | | | | | | | | | | | | | | | | | | | | |
| T3 | 21 | | | | | | | | | | | | | | | | | | | | | |
| IT5 | 20 | 713 | 650 | 359 | | 481 | 431 | 124 | 621 | 615 | 234 | 556 | 279 | 164 | 629 | 662 | 291 | 114 | 339 | 541 | 718 | 975 | 384 | 197 |
| IT6 | 26 | 150 | | | | 246 | | | | | | | 494 | | | 166 | 80 | | 317 | 255 | | | |
| IG6 | 27 | | | | | | | | | | | | | | | | | | | | | | |
| IG1 | >27 | | 97 | | | 67 | | 73 | 73 | 80 | | | | 83 | 157 | 207 | 73 | | | 247 | 93 | | |
| IG3 | >27 | 75 | 83 | | | | | | | | | | | 57 | 66 | 60 | | | | | | | |
| IG4 | >27 | | | | | | 106 | | | 83 | | 64 | | | | | | | | | | 143 | 64 |
| IG8 | >27 | | | | | | 64 | | | | | | | | | | | | | | | | |
| IG9 | >27 | 169 | 151 | | | | | | | 80 | | | | | | | | | | | | | |

TABLE II-continued

Amounts of IFN-γ (pg/ml) secreted by islet-derived CD8+ T-cells

| M# | Age wk | IG (Kd) | 6 (Db) | 55 (Db) | 7 (Db) | 47 (Db) | 8 (Db) | 30 (Db) | 1 (Db) | 58 (Kd) | 36 (Db) | 5 (Db) | 3 (Db) | 23 (Db) | 12 (Db) | 2 (Db) | 26 (Db) | 16 (Db) | 19 (Db) | 36 (Kd) | 13 (Db) | 46 (Db) | 70 (Kd) | 22 (Db) | 39 (Kd) | 10 (Db) | 51 (Db) |
|---|---|---|---|---|---|---|---|---|---|---|---|---|---|---|---|---|---|---|---|---|---|---|---|---|---|---|---|
| IU1 | 12 | 3938 | 4434 | | | | | | 584 | | | | | | | | | | | | | | | | | | |
| IU2 | 13 | 481 | 513 | | | | | 162 | nd | | | nd | nd | | | | | | | | | | | | | | |
| IU3 | 20 | 239 | 9239 | | 1366 | | | 52 | | | | | | | | | | | | | | | | | | | |
| IU4 | 17 | 1597 | 1811 | | 338 | 56 | | | | | | | | | | | | | | | | | | | | | |
| IU5 | 23 | 1992 | 1943 | 59 | 1393 | | 125 | 67 | 74 | | | 138 | 96 | 592 | 1450 | 121 | | | | | | | | 70 | 306 | 61 | |
| IU6 | 21 | 1213 | 1945 | | 1069 | | 67 | | | | | | | 74 | | | | | | | | | | 71 | 306 | | |
| IU7 | 19 | 7838 | 6121 | | 1304 | | 194 | 211 | | | | | | 149 | 105 | | | | | | | | | 76 | 341 | | |
| IU8 | 17 | 252 | 86 | | 1304 | | | | | | | | | 60 | 71 | | | | | | | | 943 | | | | |
| N1 | 17 | 264 | 1706 | | 278 | | | | | | | | | | | | 910 | | | | | | | | | 90 | |
| N2 | 21 | 722 | 745 | | 2030 | | 163 | | | | | | | | | | 154 | | | | | | | | | | |
| N3 | 25 | 1061 | 9099 | | 58 | | | | | | 111 | | | | | | | | | | | | | | | | |
| N4 | 25 | 344 | 440 | | | | | | | | | | | | | | | | | | | | | | | | |
| N5 | 21 | 1644 | 1647 | | 3605 | | 414 | | | | | 80 | | | | | | | | | | | | | 1374 | 659 | |
| N6 | 21 | 1915 | 1416 | | 457 | | 86 | | | | | 79 | | | | | | 73 | | | 51 | | | | | | |
| N7 | 25 | 854 | 930 | | 254 | | 617 | | | | | 157 | | | | | | | | | | | | | | | |
| N8 | 25 | 399 | 268 | | 1372 | | | | | | | | | | | | | 83 | | | | 56 | | 52 | 156 | | |
| N9 | 19 | 270 | 203 | | | | | | | | | | | | | | | | | | | | | | 151 | | |
| N10 | 19 | 38 | | | | | | | | | | | | | | | | | | | 51 | | | | | | |
| N11 | 19 | 188 | 220 | | 242 | | 77 | | | | | 70 | | | | | | 64 | | | | | | | 125 | | |
| N12 | 19 | 188 | 466 | | 1431 | | 631 | | | | | 146 | | | | | | | | | | | | | 242 | | |
| N13 | 21 | 3 | | | | | | | | | | | | | | | | | | | | | | | | | |
| N14 | 21 | 863 | 944 | | 63 | | | | | | | | | | | | | | | | | | | | | | |
| N15 | 21 | 3529 | 633 | | 426 | | | | | | | 75 | | | | | | | | | | 66 | | | 145 | | |
| N16 | 20 | 123 | 94 | | 168 | | | | | | | | | | | | | | | | | | | | | | |
| N17 | 20 | 646 | 611 | | 880 | | 129 | | | | | | | | | | | | | | | | | | | | |
| N18 | 19 | 2993 | 1775 | | | | | | | | | | | | | | | | | | | | | | | | |
| N19 | 20 | 5129 | 3387 | | | | | | | | | | | | | | | | | | | | | | | | |
| N20 | 20 | 1281 | 1551 | | | | | | | | | | | | | | | | | | | | | | | | |

TABLE II-continued

Amounts of IFN-γ (pg/ml) secreted by islet-derived CD8+ T-cells

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| N21 | 19 | 1498 | | | 656 | | | | 246 | | | | | | | 65 | | | | | | | | | | | | | | nd | |
| N22 | 16 | 2053 | nd | nd | nd | nd | nd | nd | nd | nd | nd | nd | nd | nd | nd | nd | nd | nd | nd | nd | nd | nd | nd | nd | nd | nd | nd | nd | nd | nd | nd |
| N23 | 24 | 2855 | nd | nd | nd | nd | nd | nd | nd | nd | nd | nd | nd | nd | nd | nd | nd | nd | nd | nd | nd | nd | nd | nd | nd | nd | nd | nd | nd | nd | nd |
| N24 | 18 | 491 | nd | nd | nd | nd | nd | nd | nd | nd | nd | nd | nd | nd | nd | nd | nd | nd | nd | nd | nd | nd | nd | nd | nd | nd | nd | nd | nd | nd | nd |
| N25 | 23 | 2996 | nd | nd | nd | nd | nd | nd | nd | nd | nd | nd | nd | nd | nd | nd | nd | nd | nd | nd | nd | nd | nd | nd | nd | nd | nd | nd | nd | nd | nd |
| IT1 | 16 | 1600 | 1302 | | | 275 | | | | | | | | | | | | | | | | | | | | | | | | | |
| IT2 | 16 | 1667 | 1343 | | | 263 | | | | | | | | | | | | | | | | | | | | | | | | | |
| IT3 | 15 | 1834 | 2000 | | 258 | | | | | | | | | | | | | | | | | | | | | | | | | | |
| IT4 | 20 | 2188 | 2577 | | 162 | 171 | | | | | | | | | | | | | | | | | | | | | | | | | |
| T1 | 21 | 6169 | 6393 | | 2510 | | 118 | | | | | 243 | | 61 | | 103 | | 72 | 94 | 51 | 75 | | 53 | | | | | | | | |
| T2 | 20 | 454 | 267 | | 91 | | | | | | | | | | 80 | | | 83 | | 57 | | 98 | | 74 | | 52 | | 64 | | | |
| T3 | 21 | 1 | | | | | | | | | | | | | | | | | | | | | | | | | | | | | |
| IIG1 | 20 | 1284 | 1144 | 418 | 500 | 265 | 319 | 407 | 1112 | | 615 | 474 | 958 | 724 | | | 429 | 268 | 499 | 1080 | 512 | 895 | 370 | 187 | 776 | 417 | 392 | 587 | 414 | 632 | |
| IIG5 | 26 | 395 | 113 | 119 | 108 | 114 | | | | | 1523 | | | | | | | 200 | | | | | | | | | | 1800 | | 228 | |
| IIG6 | 27 | 57 | | | | | | | | | | | | | | | | | | | | | 5800 | | | | | | | | |
| IG1 | >27 | 163 | 97 | | | | | 83 | 77 | | | | 80 | 73 | | 127 | 83 | | | 57 | 107 | | | | | 107 | | | | | 70 |
| IG3 | >27 | 1 | | | | | | | | | | | | | | | | | | | | | 128 | | | | | 940 | | | |
| IG4 | >27 | 26 | 60 | | | | | | 68 | | | | 53 | | | 64 | | | 62 | 70 | | | | | | 55 | | | 87 | | |
| IG8 | >27 | 1 | | | | | | | | | | | | | | | | | | | | | | | | | | 117 | | | |
| IG9 | >27 | 1 | | | | | | 87 | | | | | | | | | | | | | | | | | 51 | | | | | | |

Enhanced T-Cell Responses Against Subdominant Epitopes of IGRP in Mice Depleted of IGRP$_{206-214}$-Reactive CD8+ T-Cells.

Figure 10:
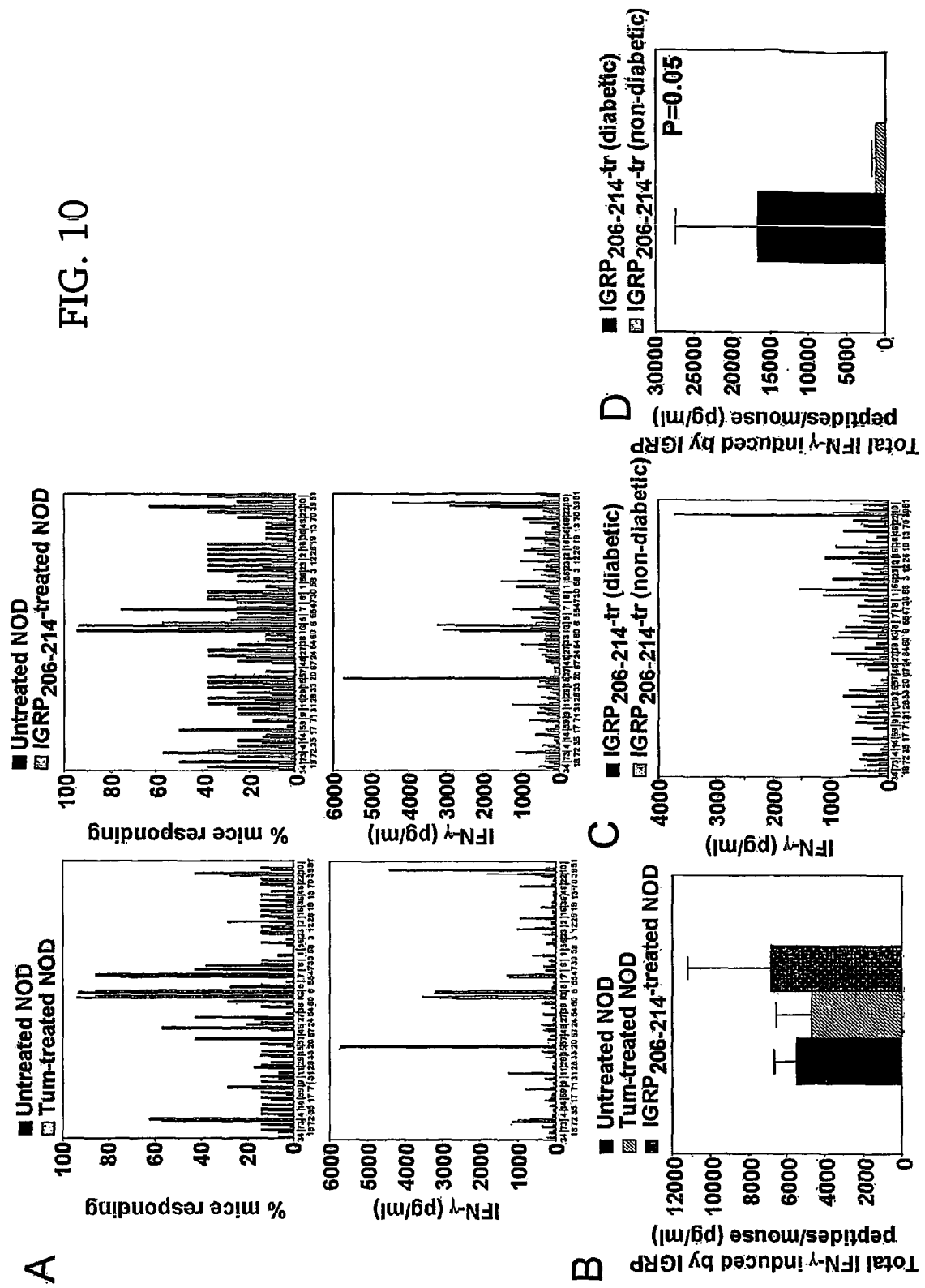
FIG. 10 is graphs of experimental results showing that IGRP$_{206-214}$-treatment reduces IGRP206-214-reactivity but increases responses against other IGRP epitopes, particularly in mice progressing to overt diabetes. Panel A (top graphs) shows the percentage of untreated, and TUM- or IGRP$_{206-214}$-treated NOD mice that contain intra-islet CD8+ T-cells recognizing epitopes of IGRP. Panel A (bottom graphs) shows the average amounts of IFN-γ secreted by islet-derived CD8+ T-cells from mice responding to the corresponding peptides. Data are from Table II. Panel B shows the cumulative amounts of IFN-γ secreted by islet-derived CD8+ T-cells in response to IGRP peptides. Panel C is the same as in Panel B except that Panel C compares IGRP$_{206-214}$-treated NOD mice that developed diabetes vs. those that did not. Panel D shows the cumulative amounts of IFN-γ secreted by islet-derived CD8+ T-cells of diabetic and non-diabetic IGRP$_{206-214}$-treated NOD mice in response to IGRP peptides.

We next investigated whether near complete deletion of the IGRP$_{206-214}$-reactive CD8+ subset by IGRP$_{206-214}$ treatment might have failed to protect mice from diabetes because it fostered the creation of a "niche" for T-cell clones recognizing sub-dominant epitopes of IGRP in islets. To that end, we evaluated the presence of anti-IGRP CD8+ T-cells in untreated, TUM-treated and IGRP$_{206-214}$-treated NOD mice (Table II, FIG. 10A). TUM treatment did not significantly increase the frequency or magnitude of anti-IGRP responses. In contrast, whereas IGRP$_{206-214}$ treatment reduced both the frequency and magnitude of the anti-IGRP$_{206-214}$ response, it increased the frequency and magnitude of T-cell responses against other IGRP epitopes (Table II and FIG. 10A). As a result, the magnitude of the total intra-islet anti-IGRP response in IGRP$_{206-214}$-treated NOD mice was similar to those calculated for untreated or TUM-treated animals (FIG. 10B). Importantly, presence of subdominant anti-IGRP-reactive CD8+ T-cell responses in islets of IGRP$_{206-214}$-treated NOD mice was most obvious in mice that had progressed to diabetes (FIGS. 6C and D). Taken together, these observations provide an explanation for the paradoxical ineffectiveness of IGRP$_{206-214}$ and NRP-V7) peptide treatment for TID prevention.

Discussion

Recent years have witnessed the emergence of CD8+ cells as major effectors of tissue damage in organ-specific autoimmunity (Liblau et al., 2002). We have previously shown that a significant fraction of islet-associated CD8+ cells in NOD mice recognize a peptide from the islet-specific protein IGRP (IGRP$_{206-214}$) Lieberman et al., 2003). We have also shown that this T-cell subset undergoes a process of avidity maturation that results from the competitive outgrowth of a small pool of high avidity clonotypes at the expense of a larger pool of non-diabetogenic, low avidity ones (Amrani et al., 2000). The present work was initiated to investigate the conditions under which manipulation of the IGRP$_{206-214}$-reactive CD8+ T-cell pool with APLs had therapeutic significance. Our data show that chronic treatment of mice with intermediate doses of an intermediate affinity APL (NRP-A7) or high doses of a low affinity APL (NRP-I4) afforded near complete protection from diabetes. Disease protection was associated with local accumulation of nondiabetogenic, low avidity IGRP$_{206-214}$-reactive CD8+ T-cells at the expense of their high avidity counterparts, which were deleted. Unexpectedly, repeated treatment of mice with low or high doses of a very high affinity APL (NRP-V7) or high doses of the natural peptide ligand (IGRP$_{206-214}$) only afforded marginal protection from disease. Strikingly, our detailed systematic analyses of the islet-associated CD8+ T-cells of these mice revealed that the islets of these mice contained very few IGRP$_{206-214}$-reactive CD8+ T-cells, but increased populations of CD8+ T-cells recognizing numerous other IGRP epitopes. These results strongly argue against the usefulness of high avidity APL therapy for the prevention of organ-specific autoimmunity via elimination of prevalent subpopulations of autoreactive T-lymphocytes.

An important new observation that has emerged from this work is that NOD islet-associated CD8+ T-cells mount responses to numerous epitopes of IGRP, in addition to IGRP$_{206-214}$. If we assume that the magnitude of IFN-γ that is secreted by islet-derived T-cells in response to different IGRP epitopes correlates with the number of reactive clonotypes (a situation that is true for IGRP$_{206}$-2,4-reactive cells), IGRP-reactive CD8+ T-cells would account for ~40% of all NOD islet-associated CD8+ T-cells. Since only about half of these T-cells recognize IGRP$_{206-214}$, these observations suggest that high prevalence of the anti-IGRP-specific CD8+ T-cell response in diabetes is not simply due to the high peripheral frequency of Vα17-Jα42+, IGRP$_{206-214}$-specific CD8+ T-cells in pre-diabetic animals (Trudeau et al., 2003). Rather, these new data point to the existence of something unique about IGRP that makes it a preferred target of autoreactive CD8+ T-cell responses in diabetogenesis. Since IGRP is expressed in beta cells at levels comparable to those of other beta cell proteins that are not target of autoimmune attack (Martin et al., 2001; Arden et al., 1999), it is tempting to speculate that its immunogenicity is related to its molecular nature and/or predicted intracellular topology (i.e. the endoplasmic reticulum membrane). Recently, it has been shown that a large fraction of MHC class Upeptide complexes in cells originate from defective ribosomal products (DRiPs), which are rapidly degraded by the proteasome after synthesis (Princiotta et al., 2003). The hydrophobicity and unusual transmembrane structure of IGRP may promote a high rate of DRiP formation in beta cells and/or dendritic cells. Alternatively, the location of IGRP in the endoplasmic reticulum membrane may foster its accumulation in beta cell apoptotic bodies, membrane-bound particles containing packed nuclear material (Cocca et al., 2002). Since the nuclear membrane is part of the ER system, IGRP might segregate with nuclear fragments into apoptotic bodies, which are readily phagocytosed by immature DCs (Sauter et al., 2000). Although this hypothesis is speculative, two lines of evidence indirectly support it. First, capture of apoptotic NIT-1 (IGRP+) and IGRP-transfected P815 cells by dendritic cells in vitro results in 8.3-T cell activation (our unpublished observations). Second, induction of beta cell apoptosis in vivo enhances cross-presentation of IGRP$_{206-214}$ to 8.3-T-cells in the PLNs (Zhang et al., 2002).

Since soluble peptides are usually cleared within 2 days (Metzler et al., 2000), they induce a weak and short-lived activation state that, in the absence of costimulatory signals (such as those induced on dendritic cells by adjuvants), leads to anergy and deletion (Aichele et al., 1994; Toes et al., 1996). Since this tolerogenic stimulus must reach an undefined threshold of TCR occupancy, the effectiveness of soluble peptides for induction of tolerance should be a function of dose, as well as affinity for TCR and MHC. Accordingly, the observation that the effectiveness of NRP-I4 and NRP-A7 therapy increased with dose was not unexpected, nor was the fact that NRP-A7 reached maximum protective activity at a lower dose than NRP-I4 (NRP-A7 is recognized with much higher avidity than NRP-I4). Notably, the islets of mice treated with protective doses of NRP-A7 and NRP-I4 contained normal or only slightly reduced numbers of IGRP$_{206-214}$-reactive CD8+ T-cells, and these cells bound NRP-V7 tetramers with lower avidity than those isolated from TUM-treated controls. These observations suggest that protective doses of NRP-A7 and NRP-I4 selectively delete pathogenic, high-avidity clonotypes, sparing their low-avidity counterparts.

Since the efficacy of vaccination protocols for induction of anti-tumor immunity requires the recruitment of high avidity CTL (Alexander-Miller et al., 1996; Perex-Diaz et al., 2002; Zeh et al., 1999), it is safe to assume that deletion of prevalent high avidity clonotypes by NRP-I4 and NRP-A7 does protect mice from T1D. However, the loss of NRP-A7's antidiabetogenic potential with increased doses of peptide despite significant depletion of the total IGRP$_{206-214}$-reactive T-cell pool implied that protection was not solely due to deletion of high avidity clonotypes. This surprising outcome was clearly not a peculiarity of NRP-A7, because mice treated with the natural ligand (IGRP$_{206-214}$) or NRP-V7 (a higher affinity APL than NRP-A7) were only slightly protected from disease despite the fact that their islets barely contained IGRP$_{206-214}$-reactive CD8+ T-cells. Therefore, the protective effect of NRP-I4 and NRP-A7 must have also required the recruitment of low avidity clonotypes. This concept is supported by mathematical modeling of T-cell avidity maturation in untreated and APL-treated mice (A.F.M. Maree, P. Santamaria, and L. Edelstein-Keshet, in preparation). This work forecasts that APL-induced protection from diabetes would require occupation of the intra-islet T-lymphocyte niche by non-pathogenic low avidity clonotypes. Whether these cells afford diabetes protection by denying access of other autoreactive specificities to the site, or by secreting immunoregulatory factors remains to be determined. Autoreactive T-cells with immunoregulatory properties have been found in normal individuals (Arif et al., 2004), and APLs can induce specific immunoregulatory T-cells (Kappos et al., 2000; Nicholson et al., 1995).

A fundamental observation of this study is that near-complete deletion of the IGRP$_{206-214}$-reactive CD8+ T-cell subset was associated with increased responses of islet-derived CD8+ T-cells against subdominant epitopes of IGRP, especially in mice that had become diabetic. This suggests that depletion of the IGRP$_{206-214}$-reactive CD8+ T-cell niche created a "vacuum" that somehow promoted the expansion of diabetogenic subdominant epitope-specific clonotypes. These subdominant epitope-specific (and potentially high avidity) CTLs may be highly effective at destroying their cellular targets because they readily evade mechanisms of tolerance, as proposed recently (Gross et al., 2004). Conceivably, these two opposing phenomena (tolerance of dominant epitope-specific T-cells and recruitment of subdominant epitope-specific T-cells) might account for the ineffectiveness of human trials using full-length protein autoantigens (Weiner, 1993; Trentham et al., 1993; McKown et al., 1999; Pozzalli et al., 2000; Group, D.P.T.-T.D.S., 2002; Kappos et al., 2000; Bielekova et al., 2000).

In sum, our findings suggest that complete elimination of a dominant T-cell subpopulation by using high doses of high affinity APLs is an inefficient way to halt the progression of cellularly complex, polyclonal autoimmune responses. Rather, we argue that effective prevention of such diseases with APLs requires the selective elimination of high avidity clonotypes and the unopposed recruitment of their low avidity, non-pathogenic counterparts. The fact that this outcome occurs only within a narrow range of dose and functional avidity bears an important lesson that may aid in the design of APL- or self antigen-based vaccines as "tolerogens" in autoimmunity. Careful examination of peptide affinity for MHC and TCR and dose are therefore warranted in the design of clinical trials.

Example 4

An Additional T-Cell-Reactive IGRP Peptide

Using procedures described in Example 1, we have cultured T-cells from the islets of 12-week-old female NOD mice. T-cells were assayed for recognition of several different IGRP peptides by interferon-γ ELISpot. Reactivity was found to peptide 152-160 of murine IGRP (having the sequence FLWSVFWLI (SEQ ID NO:4)).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

Mouse and Human IGRP Amino Acid Sequences

SEQ ID NO:1—Mouse IGRP, from NP 067306. The peptide reactive to 8.3-like T cells is bold-underlined; other peptides identified herein are underlined.

1 mdflhrsgvl iihhlqedyr tyygflnfms nvgdprnifs iyfplwfqln qnvgtkmiwv 61 avigdwfnli fkwilfghrp ywwiqeteiy pnhsspcleq fpttcetgpg spsghamgss 121 cvwyvmvtaa lsytisrmee ssvtlhrltw sflwsvfwli qisvcisrvf iathfphqvi 181 lgviggmlva eafehtpgvh maslsvylktnvflflfalg fyll lrlfgidllwsvpiak 241 kwcanpdwih idstpfaglv mlgvlfglg fainsemflr scqgengtkp sfrllcalts 301 lttmqlyrfi kipthaeplf yllsfcksasiplmvvalip ycvhmlmrpg dkktk SEQ ID NO:2—Human IGRP, from NP 066999. The peptide reactive to 8.3-like T cells is bold-underlined.

1 mdflhmgvl iiqhlqkdyr ayytflnfms nvgdprniff iyfplcfqfn qtvgtkmiwv 61 avigdwlnli fkwilfghrp ywwvqetqiy pnhsspcleq fpttcetgpg spsghamgas 121 cvwyvmvtaa lshtvcgmdk fsitlhrltw sflwsvfwli qisvcisrvf iathfphqvi 181 lgviggmlva eafehtpgiq taslgtylktnlflflfavg fylllrvini dllwsvpiak 241 kwcanpdwih idttpfaglv mlgvlfglg fainsemfll scrggnnytl sfrllcalts 301 ltilqlyhfl qiptheehlf yvlsfcksas ipltvvafip ysvhmlmkqs gkksq

What is claimed is:

1. An isolated and purified oligopeptide or polypeptide 8-10 amino acids comprising YLKTN(A/I/L/V)FL (SEQ ID NO:3) and further comprising an MHC class I molecule that is capable of binding the oligopeptide, wherein the MHC class I molecule is mouse H-2K$^d$.

2. The oligopeptide of claim 1, further comprising a cytotoxic molecule.

3. The oligopeptide or polypeptide of claim 1, in a sterile pharmaceutical preparation.

* * * * *